United States Patent
Hunter et al.

(10) Patent No.: US 9,850,319 B2
(45) Date of Patent: Dec. 26, 2017

(54) GENERATION AND USE OF POLYCLONAL AND MONOCLONAL ANTIBODIES SPECIFIC FOR 3-PHOSPHOHISTIDINE

(71) Applicants: Salk Institute for Biological Studies, La Jolla, CA (US); Sanofi, Paris (FR)

(72) Inventors: Tony Hunter, La Jolla, CA (US); Stephen Rush Fuhs, La Jolla, CA (US); Jill Meisenhelder, La Jolla, CA (US); Jacques Mauger, Tucson, AZ (US); Magda Stankova, Tucson, AZ (US); Fahad Al-Obeidi, Tucson, AZ (US); Robert A. Binne, Tucson, AZ (US)

(73) Assignees: Salk Institute for Biological Studies, La Jolla, CA (US); Sanofi, Paris (FR)

(*) Notice: Subject to any disclaimer, the term of this patent is extended or adjusted under 35 U.S.C. 154(b) by 0 days.

(21) Appl. No.: 15/500,491

(22) PCT Filed: Jul. 1, 2015

(86) PCT No.: PCT/US2015/038892
§ 371 (c)(1),
(2) Date: Jan. 30, 2017

(87) PCT Pub. No.: WO2016/018562
PCT Pub. Date: Feb. 4, 2016

(65) Prior Publication Data
US 2017/0210824 A1     Jul. 27, 2017

Related U.S. Application Data

(60) Provisional application No. 62/031,800, filed on Jul. 31, 2014.

(30) Foreign Application Priority Data

Apr. 21, 2015 (EP) ..................... 15305597

(51) Int. Cl.
*C07K 16/00* (2006.01)
*C07K 16/40* (2006.01)
*C07K 16/44* (2006.01)
*G01N 33/68* (2006.01)
*C07K 1/22* (2006.01)

(52) U.S. Cl.
CPC .............. *C07K 16/44* (2013.01); *C07K 1/22* (2013.01); *G01N 33/6803* (2013.01); *C07K 2317/565* (2013.01)

(58) Field of Classification Search
None
See application file for complete search history.

(56) References Cited

U.S. PATENT DOCUMENTS

2004/0185040 A1   9/2004   Garcia-Martinez et al.
2011/0200609 A1   8/2011   Glabe

FOREIGN PATENT DOCUMENTS

WO    WO 2013/138474 A1    9/2013

OTHER PUBLICATIONS

Fuhs et al., "Monoclonal 1- and 3-Phosphohistidine Antibodies: New Tools to Study Histidine Phosphorylation," Cell 162(1): 198-210 (Jul. 2, 2015).
Kee et al., "A Pan-specific Antibody for Direct Detection of Protein Histidine Phosphorylation," Nat Chem Biol. 9(7): 416-421 (Jul. 2013).

*Primary Examiner* — Sharon Wen
(74) *Attorney, Agent, or Firm* — Klarquist Sparkman, LLP

(57) ABSTRACT

Isolated monoclonal antibodies and or antigen binding fragments thereof are disclosed herein that specifically bind polypeptides comprising a histidine phosphorylated at N3 (3-pHis). Nucleic acids encoding these antibodies, vectors including these nucleic acids, and host cells transformed with these vectors and nucleic acids are also disclosed. Methods are also disclosed for using these antibodies, such as for detection of polypeptides comprising a histidine phosphorylated at N3 (3-pHis). In some embodiments, the methods can be used to investigate signal transduction pathways.

22 Claims, 26 Drawing Sheets

R = A or G

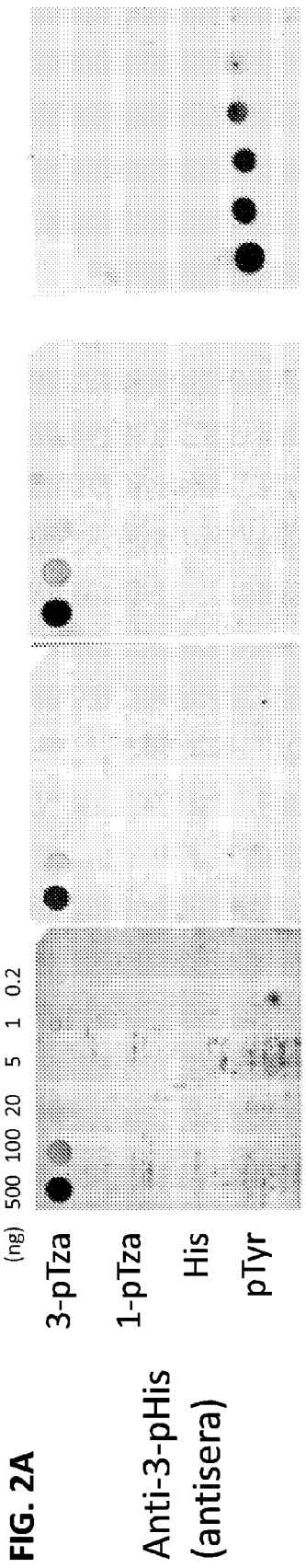
FIG. 2A
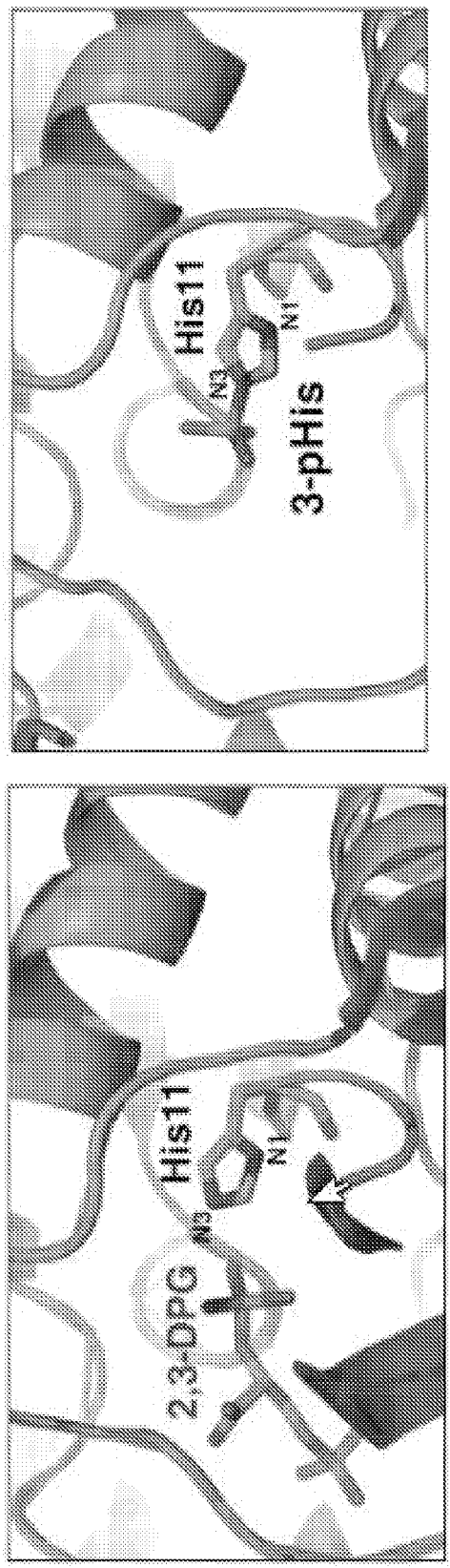
FIG. 2B
FIG. 2C

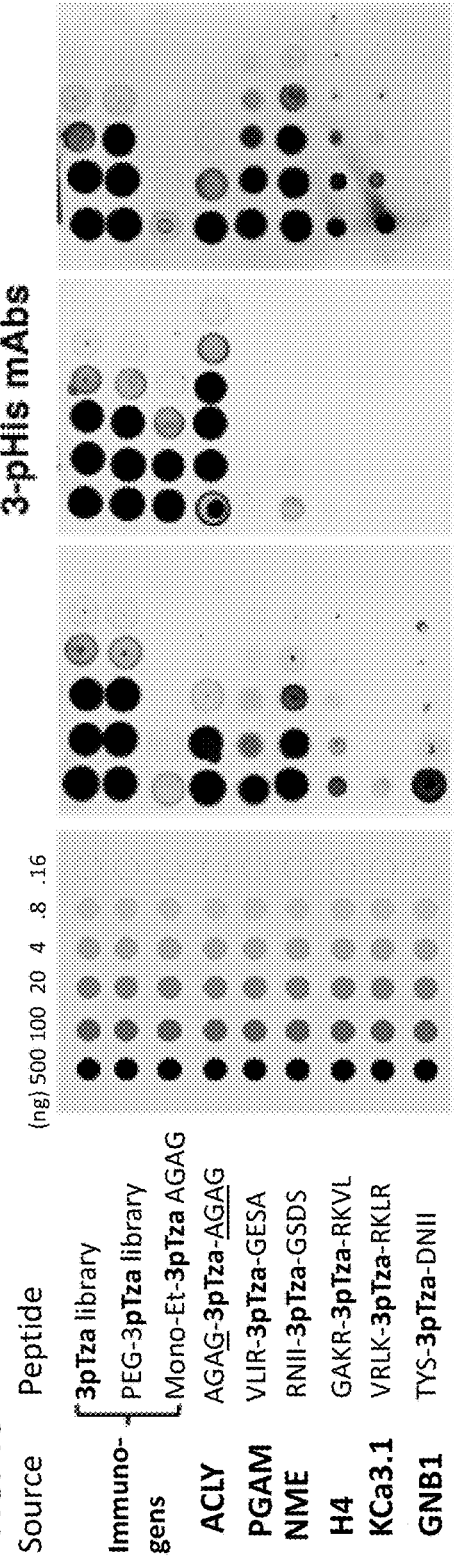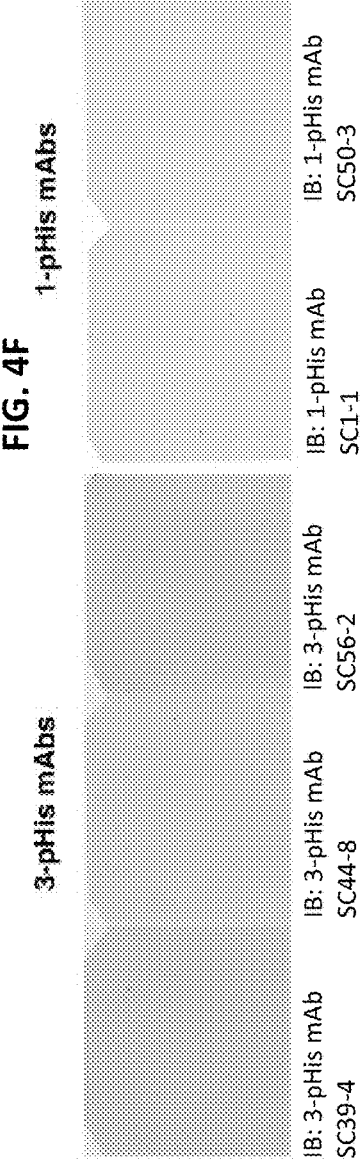
FIG. 4C
FIG. 4D
FIG. 4E
FIG. 4F

FIG. 6D
```
EVQFGHAGACAN  ACLY  H760
GRRMGHAGAIIA  SCS   H299
LVLIRHGESAWN  PGAM  H11
```
FIG. 6E
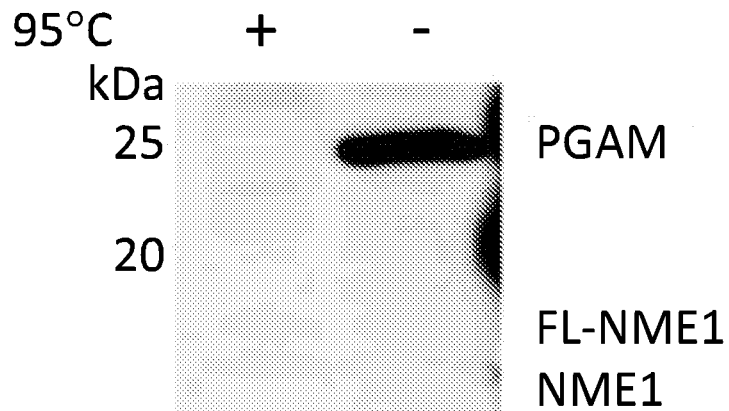
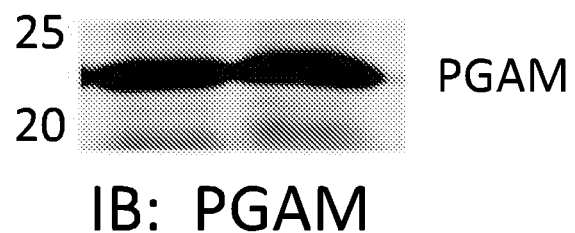

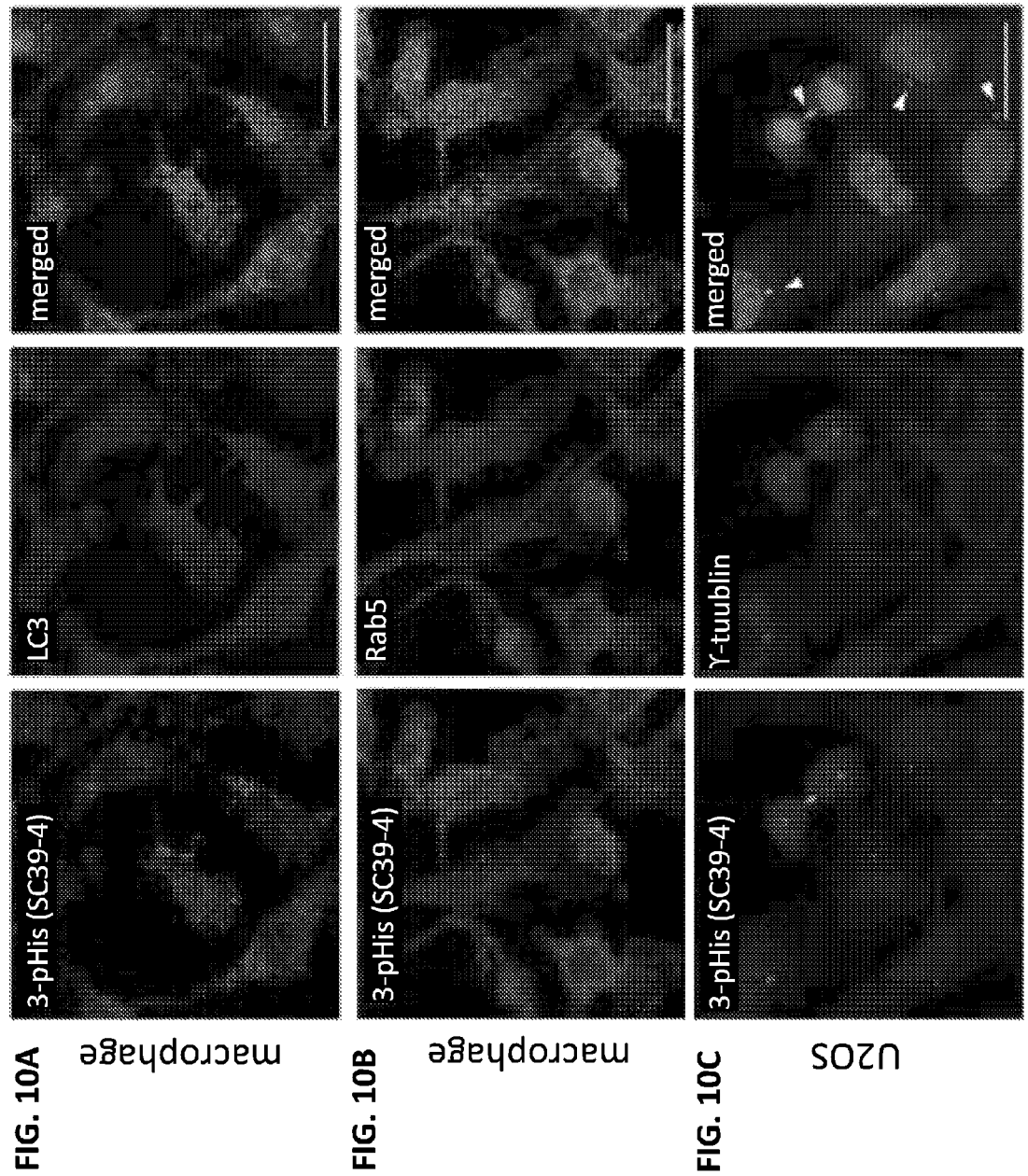

GENERATION AND USE OF POLYCLONAL AND MONOCLONAL ANTIBODIES SPECIFIC FOR 3-PHOSPHOHISTIDINE

CROSS REFERENCE TO RELATED APPLICATIONS

This is a §371 U.S. national stage of International Application No. PCT/US2015/038892, filed Jul. 1, 2015, which was published in English under PCT Article 21(2), which claims the benefit of U.S. Application No. 62/031,800, filed Jul. 31, 2014, which is incorporated by reference herein. International Application No. PCT/US2015/038892, filed Jul. 1, 2015 also claims priority to European Application No. EP 15305597.5, filed Apr. 21, 2015, which is incorporated by reference herein.

ACKNOWLEDGMENT OF GOVERNMENT SUPPORT

This invention was made with government support under grant no. 5 RO1 CA082683-15 awarded by the National Institutes of Health and grant no. 5 T32 CA009370-31 from the National Institutes of Health. The government has certain rights in the invention.

FIELD

This relates to the field of antibodies, specifically to antibodies that specifically bind a polypeptide that includes a histidine phosphorylated at N3 (3-pHis).

BACKGROUND

The majority of intracellular proteins are phosphorylated at any given time, and, while nine of the 20 amino acids can be phosphorylated, the current focus has been on serine (Ser), threonine (Thr), and tyrosine (Tyr) phosphorylation despite pHis having been first identified over 50 years ago (Boyer, *J. Biol. Chem.*, 3306 (1962)). These OH-containing amino acids form acid-stable, phosphoester (P—O) bonds upon phosphorylation (Attwood, et al., *Amino acids* 32, 145 (January 2007)). Histidine (His) forms a heat and acid-labile phosphoramidate (P—N) bond when phosphorylated. Phosphospecific antibodies have enabled the routine study of phosphoester protein phosphorylation, and the use of MS-proteomics has identified over 200,000 non-redundant sites of phosphorylation (Hornbeck et al., *Nucl. acids res* 40, D261 (January 2012)). The lack of specific antibodies to study pHis and the relative instability of the P—N bond under typical conditions used for proteomics have made it impossible to determine the prevalence of pHis, although it has been estimated that up to 6% of phosphorylation in eukaryotes occurs on His (Matthews, *Pharmac. Ther.* 67, 232 (1995)). Thus, it is possible that phosphohistidine (pHis) could be more abundant than phosphotyrosine (pTyr), which, despite its importance, comprises ~1% of all known phosphorylation sites (Hunter and Sefton, *Proc. Natl. Acad. Sci. USA* 77, 1311 (Mar. 1, 1980, 1980); Olsen et al., *Cell* 127, 635 (Nov. 3, 2006)). Since current biochemical and proteomic technologies have been optimized for preservation, enrichment and detection of the phosphoester amino acids (pSer, pThr and pTyr), pHis has remained invisible.

pHis is unique among phosphoamino acids in that two distinct, biologically relevant isomers occur. The imidazole side chain of His contains two nitrogen atoms (N1 and N3) that can both be phosphorylated to generate two biochemically distinct isomers; 1-phosphohistidine (1-pHis) or 3-phosphohistidine (3-pHis) (FIG. 1A) which are also referred to as tele-phosphohistidine (τ-pHis) and pros-phosphohistidine (π-pHis) respectively (Attwood et al., *Amino acids* 32, 145 (January 2007); McAllister et al., *Biochemical Society transactions* 41, 1072 (August 2013)). NME1 and the closely related NME2 catalyze transfer of phosphate from ATP onto NDPs through a 1-pHis enzyme intermediate. The 3-pHis isomer has been shown to be more thermodynamically stable (Attwood et al., *Amino acids* 32, 145 (January 2007)) than 1-pHis and may be more prevalent. 3-pHis is used by bacterial histidine kinases that autophosphorylate to initiate phosphotransfer cascades and it also plays an important role as an enzymatic intermediate for phospholipase D as well as several key metabolic enzymes including; phosphoglycerate mutase (PGAM), succinyl-CoA synthetase (SCS), ATP-citrate lyase (ACLY) (see, for example, Bond et al., *J. Biol. Chem.* 276, 3247 (2001)).

There is a need for the development of specific, monoclonal antibodies (mAbs) for detection of pHis that can be used to detect and functionally evaluate novel sites of protein phosphorylation. These antibodies can be used, for example, to investigate signal transduction pathways.

SUMMARY

Isolated monoclonal antibodies, as well as antigen binding fragments thereof, are disclosed herein that specifically bind polypeptides including a histidine phosphorylated at N3 (3-pHis).

In some embodiments, the antibody includes a heavy chain variable region and a light chain variable region, wherein the heavy chain variable region comprises a H-CDR1, a H-CDR2, and a H-CDR3, wherein the antibody or antigen binding fragment includes one of: a) the H-CDR1, the H-CDR2, and the H-CDR3 of the heavy chain variable region of the amino acid sequence set forth as SEQ ID NO: 1; b) the H-CDR1, the H-CDR2, and the H-CDR3 of the heavy chain variable region of the amino acid sequence set forth as SEQ ID NO: 2; c) the H-CDR1, the H-CDR2, and the H-CDR3 of the heavy chain variable region of the amino acid sequence set forth as SEQ ID NO: 3; or d) the H-CDR1, the H-CDR2, and the H-CDR3 of the heavy chain variable region of the amino acid sequence set forth as SEQ ID NO: 4, wherein the monoclonal antibody specifically binds a polypeptide comprising a histidine phosphorylated at N3 (3-pHis). In additional embodiments, the light chain variable region of the monoclonal antibody or antigen binding fragment includes a L-CDR1, a L-CDR2, and a L-CDR3, wherein the antibody or antigen binding fragment includes one of: a) the L-CDR1, the L-CDR2, and the L-CDR3 of the light chain variable region of the amino acid sequence set forth as SEQ ID NO: 5; b) the L-CDR1, the L-CDR2, and the L-CDR3 of the light chain variable region of the amino acid sequence set forth as SEQ ID NO: 6; c) the L-CDR1, the L-CDR2, and the L-CDR3 of the light chain variable region of the amino acid sequence set forth as SEQ ID NO: 7; or d) the L-CDR1, the L-CDR2, and the L-CDR3 of the light chain variable region of the amino acid sequence set forth as SEQ ID NO: 8.

In some embodiments, the antibodies include a heavy chain variable region and a light chain variable region, wherein the heavy chain variable region comprises a H-CDR1, a H-CDR2, and a H-CDR3, wherein: a) the H-CDR1, the H-CDR2, and the H-CDR3 comprise amino acids 21-28, 45-52, and 88-97 of SEQ ID NO: 1, respectively; b) the H-CDR1, the H-CDR2, and the H-CDR3 comprise amino acids 21-28, 46-52, and 91-101 of SEQ ID NO: 2, respectfully; c) the H-CDR1, the H-CDR2, and the H-CDR3 comprise amino acids 24-31, 49-55, 94-104 of SEQ ID NO: 3, respectfully; or d) the H-CDR1, the H-CDR2, and the H-CDR3 comprise amino acids 24-31, 49-55, 94-104 of SEQ ID NO: 4, respectfully. In additional embodiments, the light chain variable region comprises a L-CDR1, a L-CDR2, and a L-CDR3, wherein: a) the L-CDR1, the L-CDR2, and the L-CDR3 comprise amino acids 28-22, 51-53, and 90-102 of SEQ ID NO: 5, respectively; b) the L-CDR1, the L-CDR2, and the L-CDR3 comprise amino acids 27-34, 52-54, 91-103 of SEQ ID NO: 6, respectively; c) the L-CDR1, the L-CDR2, and the L-CDR3 comprise amino acids 27-34, 52-54, and 91-109 of SEQ ID NO: 7, respectively; or d) the L-CDR1, the L-CDR2, and the L-CDR3 comprise amino acids 27-33, 51-53 and 90-102 of SEQ ID NO: 8, respectively.

In additional embodiments, nucleic acids encoding these antibodies, vectors including these nucleic acids, and host cells transformed with these vectors and nucleic acids are also disclosed.

In further embodiments, methods are disclosed for using the antibodies, such as for detection of a polypeptide including a histidine phosphorylated at N3 (3-pHis).

The foregoing and other features of the disclosure will become more apparent from the following detailed description, which proceeds with reference to the accompanying figures.

BRIEF DESCRIPTION OF THE DRAWINGS

(FIG. 1A) Structure of histidine and the two pHis isomers; 1-phosphohistidine (1-pHis) and 3-phosphohistidine (3-pHis). (FIG. 1B) Structures of the three synthetic peptide libraries used in this study in which either His or a stable pHis mimetic (1-pTza or 3-pTza) is flanked by randomized, neutral amino acids (alanine [A] and glycine [G])]. Each library is composed of $2^8=256$ unique peptides, is acylated at the N-terminus and contains L-cysteine (Cys) for chemical ligation to KLH (Ac-Cys.G/A.G/A.G/A.G/A.X.G/A.G/A.G/A.G/A-CONH2) (SEQ ID NO: 9). (FIG. 1C) MS analysis was performed on all three of the peptide libraries. The results from analysis of the 3-pTza library is shown. (FIG. 1D) The peptide libraries were conjugated to the carrier protein keyhole limpet hemocyanin (KLH). Three rabbits were immunized with the 3-pTza library (7302, 7303 and 7304) and three rabbits were immunized with the 1-pTza library (7305, 7306 and 7307).

FIGS. 2A-2G. Screening of 3-pHis Antisera by PGAM in vitro Phosphorylation Assays. (FIG. 2A) Dot blot screening of 3-pHis antisera from rabbits 7302, 7303 and 7304 was performed as described below. (FIG. 2B) Ribbon representation of PDB entry 4hze shows the relative positions of N1 and N3 in H11 of PGAM and its phosphate donor 2,3-DPG. (FIG. 2C) Structure of PGAM (PDB entry 1e58) highlighting 3-pHis formation on the catalytic His residue H11. (FIG. 2D) GST-PGAM fusion protein was auto-phosphorylated in vitro by addition of increasing concentrations of 2,3-DPG. Reactions were stopped by addition of 5× pH 8.8 sample buffer and treated with or without heating to 95° C. for 10 min. (FIG. 2E) Purified PGAM was auto-phosphorylated in vitro by incubation with 2,3-DPG for 10 min at 30° C. Reactions were stopped by addition of 5× pH 8.8 sample buffer and treated with or without heat. (FIG. 2F) 3-pHis isoform specificity. Recombinant NME1 and PGAM were auto-phosphorylated in vitro by incubation with ATP or 2,3-DPG respectively and blotted with 3-pHis antisera from rabbits 7303 and 7304. (FIG. 2G) Phospho-PGAM spot blots. In vitro phosphorylation of PGAM was performed as in FIG. 2E except reactions were stopped by addition of 2% SDS. Reactions were treated with or without heat, diluted 1:5 and spotted directly on nitrocellulose. A representative immunoblot with 3-pHis mAb SC39-4 is shown.

(FIG. 3B) Fractions from the PEG-1-pTza affinity column including; input (IN), flowthough (FT), washes (W1, W2, W3 and W4), 10 ul column material (col) and the elution fractions (E1 to E12) were analyzed by SDS-PAGE and Coomassie staining. (FIG. 3C) Western blotting of in vitro phosphorylated NME1 (5 or 200 ng) was performed with PEG-1-pTza column elution fractions E3 to E11 at a 1:200 dilution. (FIG. 3D) Fractions from the PEG-3-pTza affinity column were analyzed as described in B. (FIG. 3E) Western blotting of in vitro phosphorylated PGAM (5 or 200 ng) was performed with PEG-3-pTza column elution fractions E3 to E11 at a 1:200 dilution.

FIGS. 4A-4F. 1-pHis and 3-pHis mAbs Detect Isomer-Specific pTza Peptides but not pTyr. Synthetic peptide dot blot arrays consisting of the His, 1-pTza or 3pTza libraries, a pTyr (NCK) peptide and peptides with either His, 1-pTza or 3pTza incorporated into defined sequences (based on the pHis protein substrates; ACLY, NME1/2, histone H4, KCa3.1 and GNB1) were spotted on nitrocellulose and probed with: (FIG. 4A) affinity-purified polyclonal 3-pHis (7303) or 1-pHis (7305) antibodies or (FIG. 4B) 1-pHis mAbs SC1-1, SC50-3 and SC77-11. Peptide layouts, sequences and their sources are shown in the grey, orange and blue boxes respectively. (FIG. 4C) 3-pTza peptide dot blot characterization of 3-pHis mAbs. A partially-deprotected, mono-ethyl ester version of the ACLY-based peptide (AGAG-mono-Et-3-pTza-AGAG) was also included. (FIGS. 4D-4F) Synthetic pTyr peptide dot blots. Peptides based on Nck, Eck and FAK were spotted on nitrocellulose and probed with: (FIG. 4D) pTyr mAb 4G10, (FIG. 4E) 3-pHis mAbs SC39-4, SC44-8 and SC56-2 or (FIG. 4F) 1-pHis mAbs SC1-1 and SC50-3.

(FIG. 5A) Src-transformed and non-transformed fibroblast cell lines (psrc11) and pancreatic stellate cells (PaSCs) were analyzed by immunoblotting with pTyr, 1-pHis or 3-pHis mAbs. Cells were pre-treated with 1 mM sodium orthovanadate for 30 min prior to lysis. (FIGS. 5B-5C) HEK 293 cell lysates were immunoblotted with 3-pHis mAbs SC39-4 and SC44-8. (FIGS. 5D-5E) Pancreatic cancer cell lysates, FLAG-NME1 293, HeLa, C2C12 and NME1 or NME2 over-expressing (OE) melanoma cells were immunoblotted with 1-pHis mAb SC1-1. All lysates (FIGS. 5A-5E) were prepared by scraping cells into 2× pH 8.8 sample buffer and treated with or without heating for 10 min.

FIGS. 6A-6E. 3-pHis Antibody Screening. (FIG. 6A) High throughput, slot blot screening of 3-pHis hybridoma subclones. Cell supernatants containing 3-pHis mAbs were screened as described using lysates from E. coli transformed with GST-PGAM. (FIG. 6B) Representative immunoblots using indicated subclones are shown. E. coli lysates identical to those used in (FIG. 6C) were treated with and without heating to 95° C. for 10 min to determine if the detected bands were heat-sensitive. Bacterial (FIG. 6B) and mammalian SCS (FIG. 6C) is detected by 3-pHis mAb SC44-8. (FIG. 6C) Mammalian cell lysates from HeLa and FLAG-NME1 293 cells were probed with mAb SC44-8. Phospho-SCS and ACLY, but not PGAM, is recognized by this mAb. (FIG. 6D) SCS H299 (SEQ ID NO: 69) is aligned with ACLY H760 (SEQ ID NO: 68) to highlight amino acids the flanking the pHis site are identical and have a G-pH-A-H-A motif that is different from the pHis site on PGAM at H11 (SEQ ID NO:70). (FIG. 6E) Cell lysates from FLAG-NME1 293 cells were treated with or without heat for 10 min. The 3-pHis mAb SC39-4 detects 3-pHis on phospho-PGAM, but not 1-pHis on NME1, in a heat-sensitive manner. Antibodies to PGAM were used to immunoblot an identical membrane to show that detection of unphosphorylated PGAM is unaffected by heat treatment.

(FIG. 7A) 5 ug of purified NME1 was incubated at RT with 1 mM ATP. (FIG. 7B) 5 ug of purified PGAM was incubated at 30 C for 10 min with 1 mM 2,3-DPG.

(FIG. 9B) Macrophages were fed Dextran-AF488 and labeled with LYSOTRACKER® for 60 min prior to fixation with PFA and staining with 1-pHis mAb SC1-1 was detected by Cy5 conjugated secondary antibodies. Bar, 10 μm. (FIG. 9C) Macrophages were incubated with Dextran-AF488 for 60 min and staining with mAb SC1-1 was detected by Cy5-conjugated secondary antibodies. (FIG. 9D) Macrophages were labeled with LYSOTRACKER® for 60 min prior to fixation and mAb SC1-1 staining was detected by AF-488 conjugated secondary antibodies. (FIG. 9E) Co-staining of macrophages with mAb SC1-1 and Phalloidin-TRITC. (FIGS. 9F-9K) HeLa cells were fixed with; PFA (FIGS. 9F-9G), or pre-permeabilized with 0.5% Triton X-100 and fixed with PFA (FIGS. 9I and 9K) or methanol (FIGS. 9H and 9J) and stained with 3-pHis mAb SC39-4 alone (FIGS. 9F-9G) or co-stained with Aurora A (FIG. 9H), γ-tubulin (FIG. 9I) or α-tubulin (FIGS. 9J-9K) antibodies. (FIG. 9F) Metaphase cells are shown in an expanded view in the right panel. (FIG. 9G) From left to right, interphase, an early prophase and anaphase cells. (FIGS. 9H-9K) Cells in metaphase, prometaphase and telophase are shown. White arrows indicate centrosomes and spindle poles. Arrows indicate midbodies in telophase cells. Nuclei were visualized with DAPI. Size Bar, 20 μm.

FIGS. 10A-10S. pHis mAb Immunofluorescence Staining of Macrophages and HeLa Cells with Negative Controls. 3-pHis mAbs Stain Cytoplasmic and Nuclear Structures Distinct from 1-pHis mAbs. Macrophages were fixed with 4% PFA and co-stained with 3-pHis mAb SC39-4 and antibodies to the organelle markers LC3 (autophagosomes [FIG. 10A]) and Rab5 (early endosomes [FIG. 10B]). (FIGS. 10C-10E) U2OS cells were fixed with PFA co-stained with 3-pHis mAb SC39-4 and antibodies to γ-tubulin and α-tubulin. Arrows indicate centrosomes and spindle poles and midbodies in telophase cells. (FIG. 10F) no peptide, (FIG. 10G) His peptide library, (FIG. 10H) 1-pTza peptide library or (FIG. 10I) 3-pTza peptide library. (FIG. 10J) Slides with PFA fixed macrophages were treated with or without boiling in citrate buffer for 10 min prior to staining with mAb SC1-1. (FIG. 10K) no peptide, (FIG. 10L) His peptide library, (FIG. 10M) 1-pTza peptide library or (FIG. 10N) 3-pTza peptide library. (FIG. 10O) Slides with PFA fixed macrophages were treated with or without boiling in citrate buffer for 10 min prior to staining with 3-pHis mAb SC39-4. (FIGS. 10P-10S) pTza blocking peptide negative controls in HeLa cells. HeLa cells were fixed with PFA and stained with mAb SC1-1 (FIGS. 10P-10Q) or mAb SC39-4 (FIGS. 10R-10S) that was pre-incubated with or without the 1-pTza or 3-pTza peptide libraries respectively for 30 min at RT with gentle agitation. Nuclei were visualized with DAPI. Size bars (FIGS. 10A-10O) 10 μm, (FIGS. 10P-10S) 20 μm.

(FIG. 11A) The 1-pHis mAb blot was quantified by densitometry and relative pNME1 signals for the IN, FT and elution fractions (E1-E3) from both the 1-pHis mAb and 3-pHis mAb columns are shown. (FIG. 11B) The 3-pHis mAb blot was quantified by densitometry and relative pPGAM signals for the IN, FT and elution fractions (E1-E3) from both the 1-pHis mAb and 3-pHis mAb columns are shown.

SEQUENCES

Figure 1A:
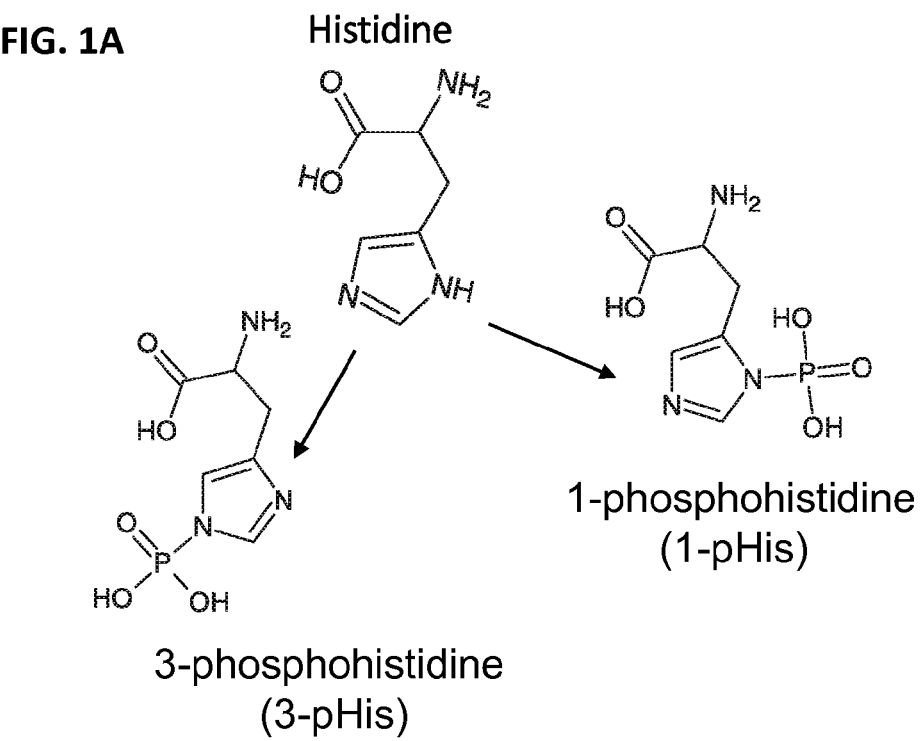
FIGS. 1A-1D. Non-hydrolyzable phosphohistidine analogues and their incorporation into peptide libraries.

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [7158-92834-03 Sequence Listing, Jan. 30, 2017, 29.3 KB], which is incorporated by reference herein.

The amino acid sequences for antibodies are provided below. In the following Fab fragment sequences ($V_H$-$C_H1$ or $V_k$-$C_k1$), the heavy and light chain variable domains ($V_H$ and $V_k$) are underlined with the CDRs highlighted in bold. The heavy and light chain constant domains ($C_H1$ and $C_k1$) are in plain capital letters. Exemplary locations of the CDRs (as identified by IMGT) are listed below each sequence. The program available at www.IMGT.org was used to align the sequences and ID the CDRs.

SEQ ID NO: 1 is the amino acid sequence of the heavy chain of mAb SC39-4.
ESGGRLVTPGGSLTLTCTVSGFSLSRYNMGWVRQAPGKGLEWIGWIPFRGSLKYATW

ATGRFTISRTSTTVDLRMTGLTAADTATYFCVRSSDGFDLWGPGTLVTVSSGQPKAPSV

FPLAPCCGDTPSSTVTLGCLVKGYLPEPVTVTWNSGTLTNGVRTFPSVRQSSGLYSLSSV

VSVTSSSQPVTCNVAHPATNTKVDKTV

CDR 1: 21-28; CDR2 45-52, CDR3 88-97; VH 1-108

SEQ ID NO: 2 is the amino acid sequence of the heavy chain of mAb SC44-8.
ESGRGLVQPGGSLTLTCTASGFSIDSYGFSWVRQAPGKGLEHIGYLTAGGRAFYASWA

KSRSTITRNTNENTVTLKMTSLTAADTATYFCAKLGSGNPVAIWGPGTLVTVSSGQPK

APSVFPLAPCCGDTPSSTVTLGCLVKGYLPEPVTVTWNSGTLTNGVRTFPAVRESSGLY

SLNSVGKVTSSSQPVTCNVAHPATNTKVDKTV

CDR1 21-28; CDR2 46-52; CDR3 91-101; VH 1-112

SEQ ID NO: 3 is the amino acid sequence of the heavy chain of mAb SC56-2.
SVKESEGGLIKPGGILTLTCTASGFSLSSYGFSWVRQAPGKGLEHIGYLHANGRAYYAT

WAKSRSTITRNTNLNTVTLQLTSLTAADTATYFCAKIGSVSDVAIWGPGTLVTVSSGQP

KAPSVFPLAPCCGDTPSSTVTLGCLVKGYLPEPVTVTWNSGTLTNGVRTFPSVRQSSGL

YSLSSVVSVTSSSQPVTCNVAHPATNTKVDKTV

CDR1 24-31; CDR2 49-55; CDR3 94-104, VH 1-115

SEQ ID NO: 4 is the amino acid sequence of the heavy chain of mAb SC60-2.
SVKESEGGLFKPTDTLTLTCTVSGFSLTTYGFSWVRQAPGKGLEWIGYVRSDGRIYYT

SWAKSRSTLTRNTNLNTVTLIMTSLTVADTATYFCAKIGSGTGVAIWGPGTLVTVSSG

QPKAPSVFPLAPCCGDTPSSTVTLGCLVKGYLPEPVTVTWNSGTLTNGVRTFPSVRQSS

GLYSLSSVVSVTSSSQPVTCNVAHPATNTKVDKTV

CDR1 24-31; CDR2 49-55; CDR3 94-104; VH 1-115

SEQ ID NO: 5 is the amino acid sequence of the light chain of mAb SC39-4.
AQFVMTQTPASVEAVVGGTVTIKCQASRDTGDGLIWYQQKPGQPPKRLIYKASTVASG

VPSRFKGRGSGTDFTLTISDLECADAATYYCHSNFYNRWTYGNAFGGGTEVVYKGDP

VAPTVLIFPPAADQVATGTVTIVCVANKYFPDVTVTWEVDGTTQTTGIENSKTPQNSAD

CTYNLSSTLTLTSTQYNSHKEYTCKVTQGTTSVVQSFNRGDC

CDR1 28-33; CDR2 51-53; CDR3 90-102, VH 1-113

SEQ ID NO: 6 is the amino acid sequence of the light chain of mAb SC44-8.
DPVMTPTPSFTSAAVGGTVTINCQSSQSVWRNKNLAWYQQKPGQPPKRLIYAIATLDS

GVPSRFSGSGSGTQFTLTISDVQCDDAATYYCVGHYGSENDAYYAFGGGTEVVVKGD

PVAPTVLIFPPSADLVATGTVTIVCVANKYFPDVTVTWEVDGTTQTTGIENSKTPQNSA

DCTYNLSSTLTLTSTQYNSHKEYTCKVTQGTTSVVQSFNRGDC

CDR1 27-34; CDR2 52-54; CDR3 91-103; VH 1-114

SEQ ID NO: 7 is the amino acid sequence of the light chain of mAb SC56-2.
DPVMTQTPSSTAAVGGTVTINCQSSESIYNNKNLAWYQQKPGQSPRRLIYSISTLASGV

SSRFKGSGSGTQFTLTISDVQCDDAATYYCVGYYYSGGYYYSGSAAYYAFGGGTEVV

VKGDPVAPTVLIFPPSADLVATGTVTIVCVANKYFPDVTVTWEVDGTTQTTGIENSKTP

QNSADCTYNLSSTLTLTSTQYNSHKEYTCKVTQGTTSVVQSFNRGDC

CDR1 27-34; CDR2 52-54: CDR3 91-109; VH 1-120

SEQ ID NO: 8 is the amino acid sequence of the light chain of mAb SC60-2.
DGVMTPTPASASAGVGGTVTINCQSSQSIYKKYIAWYQQKPGQPPKRLIYSTSTLASGV

SSRFKGSGSGTQFTLTISDVQCDDVATYYCVGYYIITNDAYYSFGGGTEVVVKGDPVAP

-continued

TVLIFPPSADLVATGTVTIVCVANKYFPDVTVTWEVDGTTQTTGIENSKTPQNSADCTY

NLSSTLTLTSTQYNSHKEYTCKVTQGTTSVVQSFNRGDC

CDR1 27-33; CDR2 51-53; CDR3 90-102; VH 1-113

SEQ ID NOs: 9-33 are amino acid sequences of synthetic polypeptides.

SEQ ID NOs: 34-61 are nucleic acid sequences of primers.

SEQ ID NOs: 62-70 are amino acid sequences of synthetic polypeptides

DETAILED DESCRIPTION

Stable pHis mimetics were incorporated into degenerate peptide libraries to immunize rabbits and develop the anti-3-pHis mAbs that constitute defined reagents with infinite supply. Several novel screening assays were developed to characterize these mAbs and it was demonstrated that they lack pTyr cross-reactivity and appear to detect pHis in a sequence-independent manner. Multiple rabbit hybridoma cell lines have been established for each pHis isomer and sequencing of the IgG heavy and light chain variable regions ($V_H$ and $V_L$) revealed the distinct complementarity determining regions (CDRs). Antibodies were isolated that specifically bind polypeptides including a histidine phosphorylated at N3 (3-pHis). Nucleic acids encoding these antibodies, vectors including these nucleic acids, host cells transformed with these vectors are disclosed herein.

These antibodies are of use in detecting phosphorylation of polypeptides. In specific, non-limiting examples, the antibodies can be used to detect polypeptides phosphorylated in a signal transduction pathway.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject.

Agent: Any substance or any combination of substances that is useful for achieving an end or result; for example, a substance or combination of substances useful for inhibiting phosphorylation or for identifying the role of phosphorylation in a biological process. Agents include, and are not limited to, proteins, nucleic acid molecules, compounds, small molecules, organic compounds, inorganic compounds, or other molecules of interest. In some embodiments, the agent is a polypeptide agent (such as an antibody), or a pharmaceutical compound. The skilled artisan will understand that particular agents may be useful to achieve more than one result.

Amino acid substitution: The replacement of one amino acid in peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as one or more phosphorylated polypeptides, such as one or more polypeptides that includes a phosphorylated histidine, for example a histidine phosphorylated at N3. Immunoglobulin genes include the kappa, lambda, alpha, gamma, delta, epsilon and mu constant region genes, as well as the myriad immunoglobulin variable region genes.

Antibodies exist, for example, as intact immunoglobulins and as a number of well characterized fragments produced by digestion with various peptidases. Fabs, Fvs, scFvs that specifically bind to a phosphorylated polypeptide, such as a polypeptide that includes a phosphorylated histidine, for example a histidine phosphorylated at N3, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook*, 1994-1995 (Pierce Chemical Co., Rockford, Ill.); Kuby, *Immunology*, 3$^{rd}$ Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest, U.S. Department of Health and Human Services,* 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for antigen binding. The extent of the framework region and CDRs have been defined (see, Kabat et al., *Sequences of Proteins of Immunological Interest*, U.S. Department of Health and Human Services, 1991, which is hereby incorporated by reference in its entirety). The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus "CDR-H1", as used herein, comprises residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system. Lefranc, et al. ("IMGT unique numbering for immunoglobulin and T cell receptor variable domains and Ig superfamily V-like domains," Dev. Comp. Immunol., 27:55-77, 2003) discloses the "IMGT" numbering scheme for CDRs. The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs of each chain are typically referred to as CDR1, CDR2, and CDR3 (from the N-terminus to C-terminus), and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found. Light chain CDRs are sometimes referred to as CDR L1, CDR L2, and CDR L3 or L-CDR1, L-CDR2 and L-CDRs. Heavy chain CDRs are sometimes referred to as CDR H1, CDR H2, and CDR H3 or H-CDR1, H-CDR2 and H-CDR3.

References to "V$_H$" or "VH" refer to the variable region of an immunoglobulin heavy chain, including that of an antibody fragment, such as Fv, scFv, dsFv or Fab. References to "V$_L$" or "VL" refer to the variable region (also called the "variable domain") of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or by a single cloned immunoglobulin. Monoclonal antibodies are produced by methods known to those of skill in the art, for instance by making hybrid antibody-forming cells from a fusion of myeloma cells with immune spleen cells. These fused cells and their progeny are termed "hybridomas." In some embodiments, monoclonal antibodies can be humanized monoclonal antibodies. In some embodiments, monoclonal antibodies can be chimeric antibodies. In some examples monoclonal antibodies are isolated from a subject. The amino acid sequences of such isolated monoclonal antibodies can be determined.

A "humanized" antibody is an antibody including a human framework region and one or more CDRs from a non-human (such as a chimpanzee, mouse, rat, or synthetic) immunoglobulin. The non-human antibody providing the CDRs is termed a "donor," and the human antibody providing the framework is termed an "acceptor." In one embodiment, all the CDRs are from the donor antibody in a humanized antibody. Constant regions need not be present, but if they are, they must be substantially identical to human antibody constant regions, such as at least about 85-90%, such as about 95% or more identical. Hence, all parts of a humanized antibody, except possibly the CDRs, are substantially identical to corresponding parts of natural human antibody sequences. A "humanized antibody" can include a humanized light chain and a humanized heavy chain. A humanized antibody binds to the same antigen as the donor antibody that provides the CDRs. The acceptor framework of a humanized antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

A "chimeric" antibody is an antibody which includes sequences from two different antibodies, which typically are of different species. In some examples, a chimeric antibody includes one or more CDRs and/or framework regions from one chimpanzee antibody and CDRs and/or framework regions from another chimpanzee antibody. In some embodiments, a chimeric antibody comprises heavy and light chain variable regions derived from a first species and heavy and light chain constant regions derived from a second species. In some embodiments, the variable and constant regions of the light chain are derived from a first species while the variable region of the heavy chain is derived from the first species and the constant region of the heavy chain is derived from a second species. In some embodiments, the first species is non-human and includes, but is not limited to, a rabbit. In additional embodiments, the second species includes, but is not limited to, humans, non-human primate, mouse or rat.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. An epitope can be phosphorylated. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest or a cell type of interest, such as a tumor cell. Exemplary pathogens include bacteria, fungi, viruses and parasites. In some embodiments, an antigen is a phosphorylated polypeptide.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody. In some embodiments, the target epitope includes a phosphorylated histidine.

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Computer readable media: Any medium or media, which can be read and accessed directly by a computer, so that the media is suitable for use in a computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Conjugate: A complex of two molecules linked together, for example, linked together by a covalent bond. In one embodiment, an antibody is linked to an effector molecule; for example, an antibody that specifically binds to a phosphorylated polypeptide, such as a polypeptide that includes a phosphorylated histidine, for example a histidine phosphorylated at N3, covalently linked to an effector molecule or to a label. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule or label is further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a sample obtained from a healthy patient. In other embodiments, the control is a tissue sample obtained from a patient diagnosed with a disease of interest, such as cancer, that serves as a positive control. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

Detecting: To identify the existence, presence, or fact of something. General methods of detecting are known to the skilled artisan (see, for example, U.S. Pat. No. 7,635,476) and may be supplemented with the protocols and reagents disclosed herein. For example, included herein are methods of detecting a cell that expresses a phosphorylated polypeptide, such as a polypeptide that includes a phosphorylated histidine, for example a histidine phosphorylated at N3.

Diagnostic: Identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition. In some examples prognostic is the probability that a subject will respond favorably to a treatment agent.

Effector molecule: The portion of a chimeric molecule that is intended to have a desired effect on a cell to which the chimeric molecule is targeted. Effector molecule is also known as an effector moiety, therapeutic agent, or diagnostic agent, or similar terms.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index as in Kabat. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the methods and for attachment to antibodies are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyro sine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Immunoadhesin: A molecular fusion of a protein with the Fc region of an immunoglobulin, wherein the immunoglobulin retains specific properties, such as Fc receptor binding and increased half-life. An Fc fusion combines the Fc region of an immunoglobulin with a fusion partner, which in general can be any protein, polypeptide, peptide, or small molecule. In one example, an immunoadhesin includes the hinge, $CH_2$, and $CH_3$ domains of the immunoglobulin gamma 1 heavy chain constant region. In another example, the immunoadhesin includes the $CH_2$, and $CH_3$ domains of an IgG.

Immunoassay: A biochemical test that measures the presence or concentration of a substance in a sample, such as a biological sample, for example a serum sample obtained from a subject, using the reaction of an antibody to its cognate antigen, for example the specific binding of an antibody to a as a polypeptide that includes a phosphorylated histidine, for example a histidine phosphorylated at N3. The presence of antigen and/or the amount of antigen present can be measured. The phosphorylation state of the antigen can also be measured. In some examples, the amount of a polypeptide that includes a phosphorylated histidine, for example a histidine phosphorylated at N3 is measured.

Measuring the quantity of antigen (such as a phosphorylated polypeptide) can be achieved by a variety of methods. One of the most common is to label either the antigen or antibody with a detectable label. In some examples an antibody that specifically binds a polypeptide that includes a phosphorylated histidine, for example a histidine phosphorylated at N3 is labeled. Methods for labeling and guidance in the choice of labels appropriate for various purposes are discussed for example in Sambrook et al. (Molecular Cloning: *A Laboratory Manual*, Cold Spring Harbor, New York, 1989) Ausubel et al. (In Current Protocols in Molecular Biology, John Wiley & Sons, New York, 1998), and Harlow & Lane, (Antibodies, *A Laboratory Manual*, Cold Spring Harbor Publications, New York, 1988).

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids and polypeptides which have been "isolated" thus include nucleic acids and proteins purified by standard purification methods. The term also embraces nucleic acids and polypeptides prepared by recombinant expression in a host cell as well as chemically synthesized nucleic acids. In some examples an antibody, such as an antibody that specifically binds phosphorylated polypeptide, such as a polypeptide that includes a phosphorylated histidine, for example a histidine phosphorylated at N3 can be isolated.

$K_d$: The dissociation constant for a given interaction, such as a polypeptide ligand interaction or an antibody antigen interaction. For example, for the bimolecular interaction of an antibody (such as any of the antibodies disclosed herein) and an antigen (such as phosphorylated polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody is labeled.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., *Bioinformatics* 2007 23(21): 2947-2948.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Phosphorylation: The addition of a phosphate ($PO_4^{3-}$) group to a polypeptide or other organic molecule. Phosphorylation of proteins plays a significant role in a number of biological processes. The reversible phosphorylation of proteins is an important regulatory mechanism that occurs in both prokaryotic and eukaryotic organisms. In vivo, serine phosphorylation is the most common type of phosphorylation, followed by threonine phosphorylation. Tyrosine, aspartate and histidine are also phosphorylated. Phosphorylation of polypeptides can be detected by antibodies, electrophoresis, such as SDS-PAGE, and mass spectrometry.

Polypeptide: Any chain of amino acids, regardless of length or post-translational modification (e.g., glycosylation or phosphorylation). In one embodiment, the polypeptide includes a phosphorylated histidine, for example a histidine phosphorylated at N3. In one embodiment, the polypeptide is a disclosed antibody or a fragment thereof.

A "residue" refers to an amino acid or amino acid mimetic incorporated in a polypeptide by an amide bond or amide bond mimetic. A polypeptide has an amino terminal (N-terminal) end and a carboxy terminal end. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A "polypeptide including a histidine phosphorylated" at N3 has one or more histidine residues phosphorylated at N3 in its amino acid sequence. The polypeptide can also have histidine residues phosphorylated at N1 and/or unphosphorylated histidines in its amino acid sequence, provided the polypeptide has at least one histidine phosphorylated at N3 is present in the amino acid sequence of the polypeptide. In some embodiments, a polypeptide including a histidine phosphorylated at N3, can have 1, 2, 3, 4, 5, 6, 7, 8, 9, 10 or more histidines phosphorylated at N3 in its amino acid sequence.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50%, 60%, 70%, 80%, 90%, 95%, 96%, 97%, 98%, or 99% of the total peptide or protein content of the preparation.

Quantitating: Determining or measuring a quantity (such as a relative quantity) of a molecule or the activity of a molecule, such as the quantity of a polypeptide that includes phosphorylated histidine, for example a histidine phosphorylated at N3 present in a sample.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sample: A biological sample obtained from a subject, such as a human or other primate or mammal, which contains for example nucleic acids and/or proteins. As used herein, biological samples include all clinical samples that include polypeptides, such as those obtained from subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In particular embodiments, the biological sample is obtained from a subject, such as in the form of a blood sample, such as serum sample.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided. Thus, in some examples a heavy chain of an antibody or antigen binding fragment thereof has at least 90%, at least 91%, at least 92%, at least 93%, at least 94%, at least 95%, at least 96%, at least 97%, at least 98% or at least 99% sequence identity to any of SEQ ID NOS: 1, 2, 3, or 4, wherein the variant specifically binds a polypeptide phosphorylated at a histidine, specifically a histidine phosphorylated at N3. In some examples a light chain of an antibody or antigen binding fragment thereof has at least 90%, at least 91%, at least 92%, at least 93%, at least 94%, at least 95%, at least 96%, at least 97%, at least 98% or at least 99% sequence identity to any of SEQ ID NOS: 5, 6, 7 or 8, wherein the variant specifically binds a polypeptide phosphorylated at a histidine, specifically a histidine phosphorylated at N3.

Nucleic acids that "selectively hybridize" or "selectively bind" do so under moderately or highly stringent conditions that excludes non-related nucleotide sequences. In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Signal Transduction: A process that occurs when an extracellular molecule activates a receptor on the surface of a cell. The receptor triggers biochemical events inside the cells, leading to a biological response. These biological responses can be, for example, changes in cell metabolism, phenotype, differentiation, proliferation, and/or gene expression. Signal transduction can involve phosphorylation of the receptor or polypeptides within the cell.

Specifically bind: When referring to an antibody, refers to a binding reaction which determines the presence of a target protein, peptide, or phosphorylated polypeptide in the presence of a heterogeneous population of proteins and other biologics. Thus, under designated conditions, an antibody binds preferentially to a particular target protein or peptide (such as phosphorylated form of the polypeptide, such as a polypeptide that includes a phosphorylated histidine, for example a histidine phosphorylated at N3) and do not bind in a significant amount to (1) other polypeptides or proteins present in the sample, does not bind the unphosphorylated form of the polypeptide, and/or does not bind the polypeptide including a different phosphorylated amino acid and/or does not bind the polypeptide include a histidine phosphorylated at N1/N2. In a specific example, an antibody that specifically binds a polypeptide including a histidine phosphorylated at N3 does not bind in a significant amount to other polypeptides or proteins present in the sample, the unphosphorylated form of the polypeptide, the polypeptide including a different phosphorylated amino acid and the polypeptide include a histidine phosphorylated at N1/N2. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$ Molar, or even less than about $10^{-10}$ Molar.

Therapeutic agent: Used in a generic sense, it includes treating agents, prophylactic agents, and replacement agents.

Therapeutically effective amount or effective amount: A quantity of a specific substance, such as an antibody, sufficient to achieve a desired effect in a subject being treated. In several embodiments, a therapeutically effective amount is the amount necessary to reduce a sign or symptom of a disorder. When administered to a subject, a dosage will generally be used that will achieve target tissue concentrations that has been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Specifically Bind Phosphorylated Histidine

Isolated monoclonal antibodies (mAb) and antigen binding fragments thereof are disclosed herein that specifically bind a polypeptide phosphorylated at a histidine, specifically a histidine phosphorylated at N3. In some embodiments, the monoclonal antibodies specifically bind a polypeptide including a histidine phosphorylated at N3 (3-pHis) with an equilibrium constant ($K_d$) of 1 nM or less. In several embodiments, the monoclonal antibodies and antigen binding fragments bind a polypeptide including a histidine phosphorylated at N3, with a binding affinity of $1\times10^{-9}$ M, at least about $1.5\times10^{-9}$ M, at least about $2\times10^{-9}$ M, at least about $3\times10^{-9}$ M, at least about $4\times10^{-9}$ M, at least about $5\times10^{-9}$ M, at least about $6\times10^{-9}$ M, at least about $7\times10^{-9}$ M, at least about $8\times10^{-9}$ M, at least about $9\times10^{-9}$ M, or at least about $1\times10^{-10}$ M.

The structure of histidine is shown below (arrow shows the N3 position):

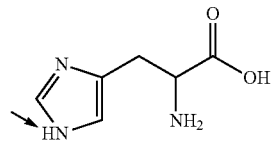

The monoclonal antibodies disclosed herein bind to a polypeptide including a histidine phosphorylated at N3 regardless of the amino acid sequence of the polypeptide. In some embodiments, the monoclonal antibodies disclosed herein can specifically bind to a polypeptide that includes a histidine phosphorylated at N3 that is present in any amino acid sequence. Thus, any amino acid sequence can be specifically bound by the mAb, provided the amino acid sequence includes histidine phosphorylated at N3.

In some embodiments, the monoclonal antibody can bind more than one polypeptide including a histidine phosphorylated at N3, wherein the amino acid sequences of the polypeptide differ. However, all the polypeptides must include a histidine phosphorylated at N3. Thus, the antibody specifically binds to these polypeptides. In specific examples, the amino acid sequence of the polypeptide is not critical for binding of the monoclonal antibody. In additional embodiments, the antibody specifically binds one or more polypeptides including a histidine phosphorylated at N3, but does not bind the polypeptides when histidine is not phosphorylated at N3.

In further embodiments, the monoclonal antibody can bind a polypeptide with a specified amino acid sequence ("X") including a histidine phosphorylated at N3, but does not bind the polypeptide with the specified amino acid sequence ("X") when the polypeptide does not include a histidine phosphorylated at N3. The monoclonal antibody can also bind a polypeptide with a different amino acid sequence ("Y") including a histidine phosphorylated at N3, but does not bind the polypeptide with the specified amino acid sequence ("Y") when the polypeptide does not include a histidine phosphorylated at N3.

The monoclonal antibody can be of any isotype. The monoclonal antibody can be, for example, an IgM or an IgG antibody, such as $IgG_1$ or an $IgG_2$. The class of an antibody that specifically binds a polypeptide phosphorylated at a histidine, specifically a histidine phosphorylated at N1 or N3, can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds a polypeptide phosphorylated at a histidine, specifically a histidine phosphorylated at N1 or N3 that was originally IgM may be class switched to an IgG. Class switching can be used to convert one IgG subclass to another, such as from $IgG_1$ to $IgG_2$.

The monoclonal antibodies disclosed herein can be rabbit antibodies and can include a rabbit framework region. In some embodiments, the monoclonal antibodies are humanized, and thus include one or more human framework regions. Exemplary framework regions are disclosed, for example, in PCT Publication No. WO 2011/038290 and U.S. Patent Application No. 2012/0244166A1, which are incorporated by reference herein. In some embodiments, the monoclonal antibodies disclosed herein are chimeric antibodies. In some embodiments, the monoclonal antibodies include rabbit and human regions.

In some embodiments, the monoclonal antibody includes both a heavy chain variable domain and a light chain variable domain. Naturally-occurring antibodies are immunoglobulin molecules comprised of four polypeptide chains, two heavy (H) chains and two light (L) chains inter-connected by disulfide bonds. Each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, called complementarity determining regions (CDR), interspersed with regions that are more conserved, called framework regions (FWR). Each VH and VL is composed of three CDRs and four FWRs, arranged from amino-terminus to carboxy-terminus in the following order: FWR1, CDR1, FWR2, CDR2, FWR3, CDR3, FWR4.

In several embodiments, the monoclonal antibodies include a heavy chain comprising a heavy chain complementarity determining region (H-CDR)1, a H-CDR2 and an H-CDR3, and a light chain comprising a light chain complementarity determining region (L-CDR) 1, L-CDR2 and L-CDR3. In some embodiments, the antibodies include a variable heavy $(V_H)$ and a variable light $(V_L)$ chain. In several embodiments, the antibody or antigen binding fragment thereof includes heavy and light chain variable regions including the H-CDR1, H-CDR2, and H-CDR3, and L-CDR1, L-CDR2, and L-CDR3, respectively, of one of the SC39-4, SC44-8, SC56-2, or SC60-2 antibodies.

The discussion of monoclonal antibodies below refers to isolated monoclonal antibodies that include heavy and light chain variable domains including at least one complementarity determining region (CDR), such as a CDR1, CDR2 and CDR3. The person of ordinary skill in the art will understand that various CDR numbering schemes (such as the Kabat, Chothia or IMGT numbering schemes) can be used to determine CDR positions. The amino acid sequence and the CDR positions of the heavy and light chain of the SC39-4, SC44-8, SC56-2 and SC60-2 monoclonal antibodies according to the IMGT are provided herein. The person of skill in the art will readily understand use of various CDR numbering schemes when referencing particular amino acids of the antibodies disclosed herein.

In some embodiments, disclosed is an isolated monoclonal antibody or antigen binding fragment thereof, including a heavy chain variable region and a light chain variable region, wherein the heavy chain variable region includes a H-CDR1, a H-CDR2, and a H-CDR3, wherein the antibody or antigen binding fragment includes: a) the H-CDR1, the H-CDR2, and the H-CDR3 of the heavy chain variable domain of the amino acid sequence set forth as SEQ ID NO: 1; b) the H-CDR1, the H-CDR2, and the H-CDR3 of the heavy chain variable domain of the amino acid sequence set forth as SEQ ID NO: 2; c) the H-CDR1, the H-CDR2, and the H-CDR3 of the heavy chain variable domain of the amino acid sequence set forth as SEQ ID NO: 3; or d) the H-CDR1, the H-CDR2, and the H-CDR3 of the heavy chain variable domain of the amino acid sequence set forth as SEQ ID NO: 4, wherein the monoclonal antibody specifically binds a polypeptide including a histidine phosphorylated at N3 (3-pHis). In additional embodiments, disclosed is an isolated monoclonal antibody or antigen binding fragment of claim 1, wherein the light chain variable domain includes a L-CDR1, a L-CDR2, and a L-CDR3, wherein the antibody or antigen binding fragment includes: a) the L-CDR1, the L-CDR2, and the L-CDR3 of the light chain variable domain of the amino acid sequence set forth as SEQ ID NO: 5; b) the L-CDR1, the L-CDR2, and the L-CDR3 of the light chain variable domain of the amino acid sequence set forth as SEQ ID NO: 6; c) the L-CDR1, the L-CDR2, and the L-CDR3 of the light chain variable domain of the amino acid sequence set forth as SEQ ID NO: 7; or d) the L-CDR1, the L-CDR2, and the L-CDR3 of the light chain variable domain of the amino acid sequence set forth as SEQ ID NO: 8. In additional embodiments, disclosed is an isolated monoclonal antibody or antigen binding fragment, including a) the H-CDR1, H-CDR2, and H-CDR3 of the amino acid sequence set forth as SEQ ID NO: 1, and the L-CDR1, L-CDR2, and L-CDR3 of the amino acid sequence set forth as SEQ ID NO: 5; b) the H-CDR1, H-CDR2, and H-CDR3 of the amino acid sequence set forth as SEQ ID NO: 2 and the L-CDR1, L-CDR2, and L-CDR3 of the amino acid sequence set forth as SEQ ID NO: 6; c) the H-CDR1, H-CDR2, and H-CDR3 of the amino acid sequence set forth as SEQ ID NO: 3 and the L-CDR1, L-CDR2, and L-CDR2 of the amino acid sequence set forth as SEQ ID NO: 7; or d) the H-CDR1, H-CDR2, and H-CDR3 of the amino acid sequence set forth as SEQ ID NO: 4, and the L-CDR1, L-CDR2, and L-CDR3 of the amino acid sequence set forth as SEQ ID NO: 8.

For example, in some embodiments, the antibody includes a heavy chain variable region including a H-CDR1, H-CDR2, and/or H-CDR3 including amino acids 21-28, 45-52, and 88-97 of SEQ ID NO: 1, respectively. In further embodiments, the antibody includes a heavy chain variable region including a H-CDR1, H-CDR2, and/or H-CDR3 including amino acids 21-28, 46-52, and 91-101 of SEQ ID NO: 2, respectively. In additional embodiments, the antibody includes a heavy chain variable region including a H-CDR1, H-CDR2, and/or H-CDR3 including amino acids 24-31, 49-55, 94-104 of SEQ ID NO: 3, respectively. In more embodiments, the antibody includes a heavy chain variable region including a H-CDR1, H-CDR2, and/or H-CDR3 including amino acids 24-31, 49-55, 94-104 of SEQ ID NO: 4, respectively. The antibody specifically binds polypeptide including a histidine phosphorylated at N3.

In some embodiments, the antibody includes a light chain variable region including a L-CDR1, L-CDR2, and/or L-CDR3 including amino acids 28-22, 51-53, and 90-102 of SEQ ID NO: 5, respectively. In further embodiments, the antibody includes a light chain variable region including a L-CDR1, L-CDR2, and/or L-CDR3 including amino acids 27-34, 52-54, 91-103 of SEQ ID NO: 6, respectively. In additional embodiments, the antibody includes a light chain variable region including a L-CDR1, L-CDR2, and/or L-CDR3 including amino acids 27-34, 52-54, and 91-109 of SEQ ID NO: 7, respectively. In more embodiments, the antibody includes a light chain variable region including a L-CDR1, L-CDR2, and/or L-CDR3 including amino acids 27-33, 51-53 and 90-102 of SEQ ID NO: 8, respectively. The antibody specifically binds a polypeptide including a histidine phosphorylated at N3.

In some embodiments, the antibody includes a heavy chain variable region including a H-CDR1, H-CDR2, and H-CDR3 including amino acids 28, 45-52, and 88-97 of SEQ ID NO: 1, respectively, and a light chain variable region including a L-CDR1, L-CDR2, and L-CDR3 including amino acids 28-22, 51-53, and 90-102 of SEQ ID NO: 5 respectively. In additional embodiments, the antibody includes a heavy chain variable region including a H-CDR1, H-CDR2, and H-CDR3 including amino acids 21-28, 46-52, and 91-101 of SEQ ID NO: 2, respectively, and a light chain variable region including a L-CDR1, L-CDR2, and L-CDR3 including amino acids 27-34, 52-54, 91-103 of SEQ ID NO: 6, respectively. In further embodiments, the antibody includes a heavy chain variable region including a H-CDR1, H-CDR2, and H-CDR3 including amino 24-31, 49-55, 94-104 of SEQ ID NO: 3, respectively, and a light chain variable region including a L-CDR1, L-CDR2, and L-CDR3 including amino acids 27-34, 52-54, and 91-109 of SEQ ID NO: 7, respectively. In more embodiments, the antibody includes a heavy chain variable region including a H-CDR1, H-CDR2, and H-CDR3 including amino acids 24-31, 49-55, 94-104 of SEQ ID NO: 4, respectively, and a light chain variable region including a L-CDR1, L-CDR2, and L-CDR3 including amino acids 27-33, 51-53 and 90-102 of SEQ ID NO: 8, respectively.

In further embodiments, the antibody includes a heavy chain variable region including an amino acid sequence at least 95%, 96%, 97%, 98%, or 99% identical to the amino acid sequence set forth as one of a) amino acids 1-108 of SEQ ID NO: 1; b) amino acids 1-112 of SEQ ID NO: 2; c) amino acid 1-115 of SEQ ID NO: 3, or d) amino acids 1-115 of SEQ ID NO: 4. In more embodiments, the antibody includes a light chain variable region including an amino acid sequence at least 95%, 96%, 97%, 98%, or 99% identical to the amino acid sequence set forth as one of a) amino acids 1-113 of SEQ ID NO: 5; b) amino acids 1-114 of SEQ ID NO: 6; c) amino acid 1-120 of SEQ ID NO: 7; or d) amino acids 1-113 of SEQ ID NO: 8. Thus, the antibody can include a) a heavy chain variable region including an amino acid sequence at least 95%, 96%, 97%, 98%, or 99% identical to the amino acid sequence set forth as amino acids 1-108 of SEQ ID NO: 1 and a light chain variable region including an amino acid sequence at least 95%, 96%, 97%, 98%, or 99% identical to the amino acid sequence set forth as amino acids amino acids 1-113 of SEQ ID NO: 5; b) a heavy chain variable region including an amino acid sequence at least 95%, 96%, 97%, 98%, or 99% identical to the amino acid sequence set forth as amino acids 1-112 of SEQ ID NO: 2 and a light chain variable region including an amino acid sequence at least 95%, 96%, 97%, 98%, or 99% identical to the amino acid sequence set forth as amino acids amino acids 1-114 of SEQ ID NO: 6; c) a heavy chain variable region including an amino acid sequence at least 95%, 96%, 97%, 98%, or 99% identical to the amino acid sequence set forth as amino acids 1-115 of SEQ ID NO: 3 and a light chain variable region including an amino acid sequence at least 95%, 96%, 97%, 98%, or 99% identical to the amino acid sequence set forth as amino acids amino acids 1-120 of SEQ ID NO: 7; or d) a heavy chain variable region including an amino acid sequence at least 95%, 96%, 97%, 98%, or 99% identical to the amino acid sequence set forth as amino acids 1-115 of SEQ ID NO: 4 and a light chain variable region including an amino acid sequence at least 95%, 96%, 97%, 98%, or 99% identical to the amino acid sequence set forth as amino acids amino acids 1-113 of SEQ ID NO: 8. The antibody specifically binds a polypeptide including a histidine phosphorylated at N3.

In additional embodiments, the antibody includes a heavy chain variable region that includes a) amino acids 1-108 of SEQ ID NO: 1; b) amino acids 1-112 of SEQ ID NO: 2; c) amino acid 1-115 of SEQ ID NO: 3, or d) amino acids 1-115 of SEQ ID NO: 4. In specific non-limiting examples, the heavy chain variable region can be paired with any light chain variable region, provided the antibody specifically binds a polypeptide including a histidine phosphorylated at N3.

In some embodiments, the antibody includes a light chain variable region that includes a) amino acids 1-113 of SEQ ID NO: 5; b) amino acids 1-114 of SEQ ID NO: 6; c) amino acid 1-120 of SEQ ID NO: 7; or d) amino acids 1-113 of SEQ ID NO: 8. In specific non-limiting examples, the light chain variable region can be paired with any heavy chain variable region, provided the antibody specifically binds a polypeptide including a histidine phosphorylated at N3.

Thus, in specific non-limiting examples, the monoclonal antibody includes a) a heavy chain variable region including amino acids 1-108 of SEQ ID NO: 1 and a light chain variable region including amino acids 1-113 of SEQ ID NO: 5; b) a heavy chain variable region including amino acids 1-112 of SEQ ID NO: 2 and a light chain variable region including amino acids 1-114 of SEQ ID NO: 6; c) a heavy chain variable region including amino acids 1-115 of SEQ ID NO: 3 and a light chain variable region including amino acids 1-120 of SEQ ID NO: 7, or d) a heavy chain variable region including amino acids 1-115 of SEQ ID NO: 4 and light chain variable region including amino acids 1-113 of SEQ ID NO: 8.

In some embodiments, an antibody that specifically binds a polypeptide including a histidine phosphorylated at N3, as disclosed herein, includes up to 10 amino acid substitutions (such as up to 1, 2, 3, 4, 5, 6, 7, 8, or up to 9 amino acid substitutions) in the framework regions of the heavy chain of the antibody, or the light chain of the antibody, or the heavy and light chains of the antibody. The antibody specifically binds a polypeptide including a histidine phosphorylated at N3.

In several embodiments, the constant region of the antibody includes one or more amino acid substitutions to optimize half-life of the antibody. The half-life of IgG Abs is in serum regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The antibody can also be an immunoadhesin.

One of skill will realize that conservative variants of the antibodies can be produced. Such conservative variants employed in antigen binding fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ or the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. Thus, in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity.

Chimeric antibodies are also provided. The antibodies can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibodies or antigen binding fragments disclosed herein can be derivatized or linked to another molecule (such as another peptide or protein). In general, the antibodies or portion thereof is derivatized such that the binding to polypeptides including a histidine phosphorylated at N3 is not affected adversely by the derivatization or labeling. For example, the antibody can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific or multispecific antibodies). Suitable crosslinkers include those that are heterobifunctional, having two distinctly reactive groups separated by an appropriate spacer (such as m-maleimido-benzoyl-N-hydroxysuccinimide ester) or homobifunctional (such as disuccinimidyl suberate). Such linkers are available from Pierce Chemical Company, Rockford, Ill. Thus, bivalent and multivalent antibodies can be produced, such as including more than one monoclonal antibody or antigen binding from of antibody that specifically bind polypeptides including a histidine phosphorylated at N3. In some examples, the disclosed antibodies are oligomers of antibodies, such as dimers, trimers, tetramers, pentamers, hexamers, septamers, octomers and so on. In some examples, the antibodies are dimers or pentamers.

The monoclonal antibodies disclosed herein can be of any isotype. The monoclonal antibody can be, for example, an IgM or an IgG antibody, such as $IgG_1$, $IgG_2$, $IgG_3$ or an $IgG_4$. The class of an antibody that specifically binds a polypeptide including a histidine phosphorylated at N3 can be switched with another (for example, IgG can be switched to IgM), according to well-known procedures. For example, a nucleic acid molecule encoding the $V_L$ or $V_H$ of a disclosed antibody can be operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds a polypeptide including a histidine phosphorylated at N3, that was originally IgG, may be class switched to an IgM. Class switching can be used to convert one IgG subclass to another, such as from $IgG_1$ to $IgG_2$, $IgG_3$, or $IgG_4$.

Antigen binding fragments of the antibodies that specifically bind to polypeptides including a histidine phosphorylated at N3 are also encompassed by the present disclosure, such as single-domain antibodies (for example, VH domain antibodies), Fab, F(ab')$_2$, and Fv. These antigen binding fragments retain the ability to specifically bind polypeptides including a histidine phosphorylated at N3. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFV (also known as a "mini-antibody"); and (7) VH single-domain antibody, an antigen binding fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some embodiments, the antigen binding fragments are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional examples, the Fv fragments include $V_H$ and $V_L$ chains connected by a peptide linker. These single-chain antigen binding proteins (scFv) are prepared by constructing a structural gene including DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody ($scFV_2$), are also contemplated.

Antigen binding fragments can be prepared by proteolytic hydrolysis of the antibody or by expression in *E. coli* of DNA encoding the fragment. Antigen binding fragments can be obtained by pepsin or papain digestion of whole antibodies by conventional methods. For example, antigen binding fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

In some cases, antigen binding fragments can be prepared by proteolytic hydrolysis of the antibody or by expression in a host cell (such as *E. coli*) of DNA encoding the fragment. Antigen binding fragments can be obtained by pepsin or papain digestion of whole antibodies by conventional methods. For example, antigen binding fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Conjugates

Monoclonal antibodies, or antigen binding fragments thereof, that specifically bind polypeptides including a histidine phosphorylated at N3, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds a polypeptide including a histidine phosphorylated at N3. One of skill in the art will appreciate that various effector molecules and detectable markers can be used, including (but not limited to) radioactive agents such as $^{125}I$, $^{32}P$, $^{3}H$ and $^{35}S$ and other detectable labels, enzymes, target moieties, drugs and ligands, etc.

Effector molecules and detectable markers can be linked to an antibody or antigen binding fragment of interest using any number of means known to those of skill in the art. Both covalent and noncovalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to the antibody (or antigen binding fragment) and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

A monoclonal antibody that specifically binds a polypeptide including a histidine phosphorylated at N3 (or antigen binding fragment thereof) can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP).

An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody or antigen binding fragment may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

An antibody or antigen binding fragment can be conjugated with a radiolabeled amino acid. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody or antigen binding fragment can also be derivatized with a chemical group such as polyethylene glycol (PEG), a methyl or ethyl group, or a carbohydrate group. These groups may be useful to improve the biological characteristics of the antibody or antigen binding fragment, such as to increase serum half-life or to increase tissue binding.

The average number of effector molecule or detectable marker moieties per antibody or antigen binding fragment in a conjugate can range, for example, from 1 to 20 moieties per antibody or antigen binding fragment. For some conjugates, the average number of effector molecule or detectable marker moieties per antibody or antigen binding fragment may be limited by the number of attachment sites on the antibody or antigen binding fragment. For example, where the attachment is a cysteine thiol, an antibody or antigen binding fragment may have only one or several cysteine thiol groups, or may have only one or several sufficiently reactive thiol groups through which a linker may be attached. In certain embodiments, the average number of effector molecule or detectable marker moieties per antibody or antigen binding fragment in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298, incorporated by reference herein in its entirety. The average number of effector molecule or detectable marker moieties per antibody or antigen binding fragment in preparations of conjugates may be characterized by conventional means such as mass spectroscopy and, ELISA assay.

The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/03448, incorporated by reference herein in its entirety.

Nucleotides, Expression Vectors and Host Cells

Nucleic acids encoding the amino acid sequences of antibodies that specifically bind polypeptides including a histidine phosphorylated at N3 are provided. Nucleic acid molecules encoding these antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule, detectable marker or antibody or antigen binding fragment sequence.

Nucleic acid sequences encoding the antibodies that specifically bind polypeptides including a histidine phosphorylated at N3 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding an antibody that specifically binds a polypeptide including a histidine phosphorylated at N3 (or antigen binding fragment thereof) can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody or antigen binding fragment of use is prepared by inserting the cDNA which encodes a variable region from an antibody into a vector which includes the cDNA encoding an effector molecule or detectable marker, such as an enzyme or label. The insertion is made so that the variable region and the effector molecule or detectable marker are read in frame so that one continuous polypeptide is produced. Thus, the encoded polypeptide contains a functional Fv region and a functional effector molecule or detectable marker region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody or antigen binding fragment, so that the enzyme or polypeptide marker is located at the carboxyl terminus of the heavy chain variable region. The heavy chain-variable region can subsequently be ligated to a light chain variable region of the antibody or antigen binding fragment using disulfide bonds. In a yet another example, cDNA encoding an enzyme or a polypeptide marker is ligated to a light chain variable region of an antibody or antigen binding fragment, so that the enzyme or polypeptide marker is located at the carboxyl terminus of the light chain variable region. The light chain-variable region can subsequently be ligated to a heavy chain variable region of the antibody or antigen binding fragment using disulfide bonds.

Once the nucleic acids encoding the conjugate, antibody, or fragment thereof, are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or antigen binding fragment or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa, 293 and myeloma cell lines.

Isolation and purification of recombinantly expressed polypeptide can be carried out by conventional means including preparative chromatography and immunological separations. Once expressed, the conjugate, antibody, or antigen binding fragment thereof, can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein. Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry*, 9: 5015-5021, 1970, incorporated by reference herein, and especially as described by Buchner et al., supra. Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, antigen binding fragments and conjugates thereof can be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Methods of Detection

Methods are provided for detecting the presence of a polypeptide including a histidine phosphorylated at N3 in a subject. In some embodiments, the methods include contacting a cell from a subject with one or more of the antibodies disclosed herein to form an immune complex. The presence (or absence) of the immune complex is then detected. The presence of the immune complex indicates the presence of a histidine phosphorylated at N3 in the polypeptide. The detection methods can involve in vitro detection of the immune complex. In some embodiments, the detection methods distinguish the presence of histidine phosphorylated at N3 in the polypeptide from histidine phosphorylated at N1. In additional embodiments, the detection method distinguish the presence of a histidine phosphorylated at N3 in the polypeptide from an unphosphorylated polypeptide. In additional embodiments, the methods are used to detect phosphorylated proteins in a signal transduction pathway. In yet other embodiments, the methods can be used to quantitate the amount of a polypeptide phosphorylated at N3 in a sample.

In one embodiment, a biological sample is obtained, and the presence of a polypeptide including a histidine phosphorylated at N3 is assessed in vitro. For example, such methods include contacting a biological sample with one or more of the conjugates, antibodies, or antigen binding fragments provided herein that specifically bind polypeptide including a histidine phosphorylated at N3 to form an immune complex. The presence (or absence) of the immune complex is then detected. The presence of the immune complex indicates the presence of the polypeptide including a histidine phosphorylated at N3. For example, an increase in the presence of the immune complex in the sample as compared to formation of the immune complex in a control sample indicates the presence of the polypeptide including a histidine phosphorylated at N3. The amount of the immune complex can be quantitated.

A biological sample can be obtained from a mammalian subject of interest, such as human. The sample can be any sample, including, but not limited to, tissue from biopsies, autopsies and pathology specimens. Biological samples also include sections of tissues, for example, frozen sections taken for histological purposes. In some embodiments, the mammalian subject is treated with a therapeutic agent of interest. The biological sample can also be an extract of cells cultured in vitro. In some embodiments, cells are treated with an agent of interest to determine the effect of the agent on phosphorylation of histidine.

When using a control sample along with the test sample, a complex is detected in both samples and any statistically significant difference in the formation of complexes between the samples is indicative of the presence of polypeptide including histidine phosphorylated at N3 in the test sample.

In some examples of the disclosed methods, the antibody or antigen binding fragment that specifically binds a polypeptide including a histidine phosphorylated at N3 is conjugated to a detectable marker. In additional examples, the methods further include contacting a second antibody that specifically binds the antibody (or antigen binding fragment) that specifically binds a polypeptide including a histidine phosphorylated at N3 for a sufficient amount of time to form an immune complex and detecting this immune complex. In some examples, the second antibody is conjugated to a detectable marker. An increase in the presence of this immune complex in a biological sample compared to the presence of the immune complex in a control sample or other standard detects the presence of a polypeptide including a histidine phosphorylated at N3 in the biological sample.

Suitable detectable markers for the antibody or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

The antibodies can be used in immunohistochemical assays. These assays are well known to one of skill in the art (see Harlow & Lane, *Antibodies, A Laboratory Manual*, Cold Spring Harbor Publications, New York (1988), for a description of immunoassay formats. The assays can be, for example, immunohistochemistry (IHC), immunofluorescence (IF), immunoblotting (IB) and variations thereof including protein or peptide spot blots and slot blots, enzyme linked immuosorbant assay ELISA), radioimmunoassay (RIA), Immune Radioimmunometric Assay (IRMA), Enzyme ImmunoAssay (EIA), and CLIA (Chemioluminescent Immune Assay).

In one embodiment, the antibody or antigen binding fragment that specifically binds to a polypeptide including a histidine phosphorylated at N3 is used to detect one or more phosphorylated polypeptides in a sample from a subject. The antibody or antigen binding fragment can be directly labeled. In some embodiments, a biological sample from a subject is contacted with the antibody or antigen binding fragment and the presence of an immune complex is detected.

In further embodiments, an additional sample is obtained from the subject, such as following treatment with a therapeutic agent. After a sufficient amount of time has elapsed, another sample is obtained. The antibody or antigen binding fragment that specifically binds to a polypeptide including a histidine phosphorylated at N3 is used to detect one or more phosphorylated polypeptides in the second sample. In some embodiments, a biological sample from a subject is contacted with the antibody or antigen binding fragment and the presence of an immune complex is detected. In some examples, an increase in the amount of the immune complex compared to a control, such as in a sample taken prior to the treatment, indicates that the treatment is not effective. In other examples, a decrease in the immune complex compared to a control, such as in a sample taken prior to the treatment, indicates that the treatment is effective.

The antibodies can also be used in screening assays, wherein cells, optionally in a high through-put format, are contacted with one or more agents of interest. After a sufficient amount of time has elapsed, a sample of the cells is obtained. Extracts of the cells can be produced. The antibody or antigen binding fragment that specifically binds to polypeptides including a histidine phosphorylated at N3 is used to detect phosphorylated polypeptides in the sample. An alteration in the binding of the antibody to the sample, as compared to a control sample (such as cells not contacted with the agent) or a standard value, indicates that the agent affects phosphorylation. The assay can be used to identify therapeutic agents. The assay can also be used to identify proteins that are phosphorylated in a signal transduction pathway.

Kits

Kits are also provided. The kits will typically include an antibody or antigen binding fragment that specifically binds a polypeptide including a histidine phosphorylated at N3, and/or a conjugate thereof.

More than one of the conjugates or antibodies or antigen binding fragments that specifically bind a polypeptide including a histidine phosphorylated at N3 can be included in the kit. Thus, the kit can include two or more antibodies that specifically bind a polypeptide including a histidine phosphorylated at N3, or a multivalent or bivalent antibody or antigen binding fragment that specifically binds a polypeptide including a histidine phosphorylated at N3 and a conjugate thereof, or a combination thereof, wherein in some examples each antibody is in a separate container forming the kit. In some embodiments, an antigen binding fragment or conjugate including an antigen binding fragment, such as an Fv fragment, is included in the kit. In one example, such as for in vivo uses, the antibody can be a scFv fragment.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, or conjugates. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies or fragments thereof, or conjugates thereof, for example, in a detection method. The package insert typically includes instructions customarily included in commercial packages of diagnostic products that contain information about the usage of the antibodies, such as in particular types of assays. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art. Kits may include recombinant proteins for use as a positive control. For example recombinantly expressed and purified PGAM can be included along with 2,3-DPG and instructions for performing in vitro phosphorylation reactions and analysis by a modified SDS-PAGE method that has been optimized for the preservation and detection of a histidine phosphorylated at N3.

The following examples are provided to illustrate particular features of certain embodiments, but the scope of the claims should not be limited to those features exemplified.

EXAMPLES

Phospho-specific, monoclonal antibodies (mAbs) for phosphoester-forming (P—O) amino acids (phosphoserine, phosphothreonine and phosphotyrosine) can be used in the study of protein phosphorylation in cellular signaling. Histidine (His) phosphorylation is well studied in bacterial signal transduction; however, its role in mammalian signaling remains largely unexplored due to the lack of pHis mAbs and lability of the phosphoramidate (P—N) bond. Both nitrogen atoms (N1 and N3) in histidine's imidazole side chain can be phosphorylated to give rise to one of two pHis isomers; 1-phosphohistidine (1-pHis) and 3-phosphohistidine (3-pHis).

Disclosed herein are mAbs that bind specifically to pHis and can distinguish between both pHis isomers. Antibodies were raised in rabbits by immunization with stable pHis analogues incorporated into degenerate peptide libraries. Two novel screening assays were developed based on the isomer specific auto-phosphorylation of NME1 (Nm23-HUNDPK) and phosphoglycerate mutase (PGAM), which generate either 1-pHis or 3-pHis respectively. These assays, in combination with immunoblotting bacterial and mammalian cell lysates and sequencing mAb IgG variable domains, were used to characterize anti-1-pHis and anti-3-pHis antibodies and select hybridoma clones for establishment of monoclonal cell lines. The sequence independence of these mAbs was determined by peptide dot blot arrays. The pHis mAbs disclosed herein lack sequence specificity (for antigen binding) and do not cross-react with phosphotyrosine or the other pHis isomer. Thus, they can be used for identification and study of pHis substrates in any species using a variety of immunological, proteomic and biological assays.

Example 1

Figure 1B:
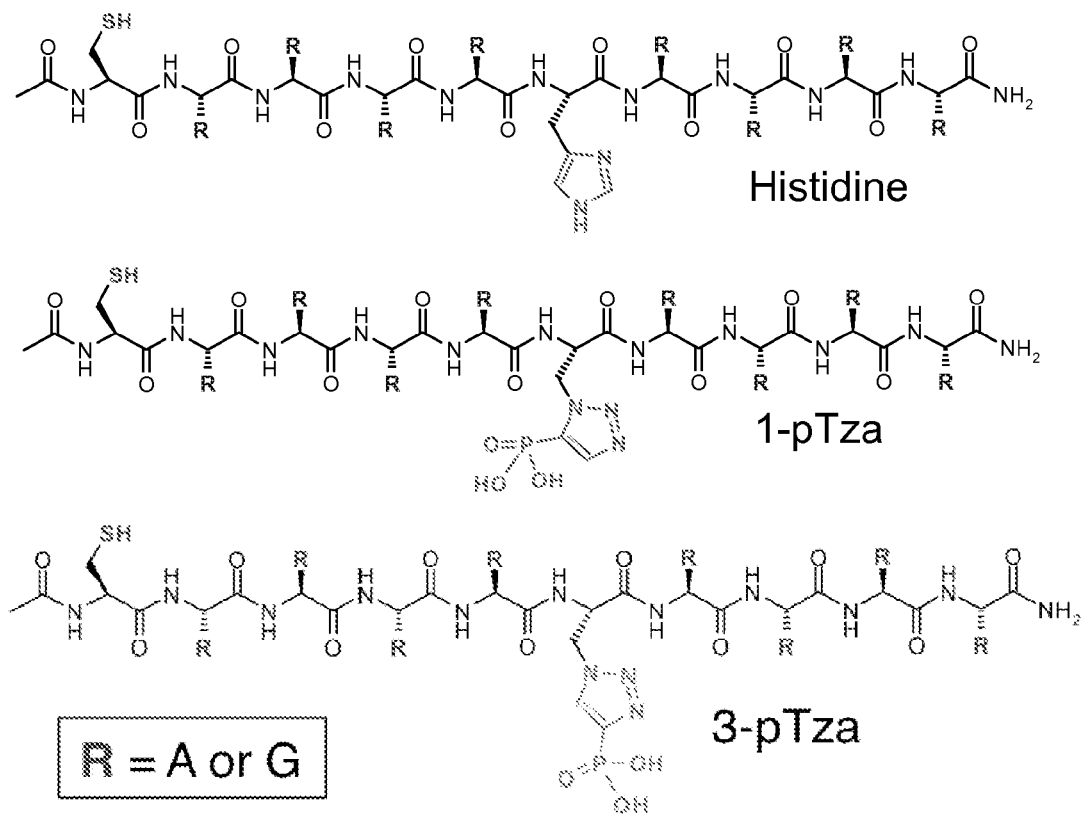
Figure 1C:
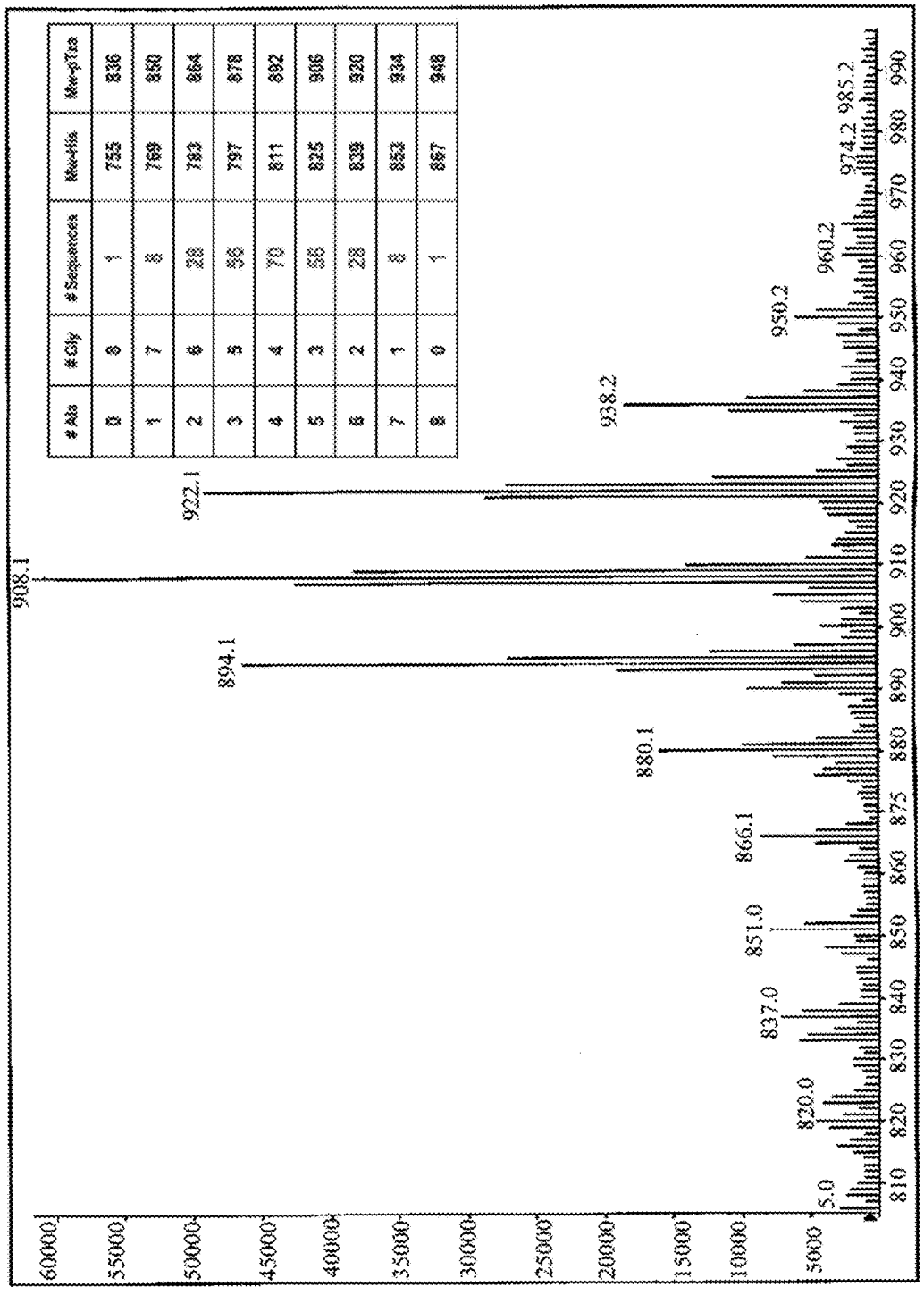
Figure 1D:
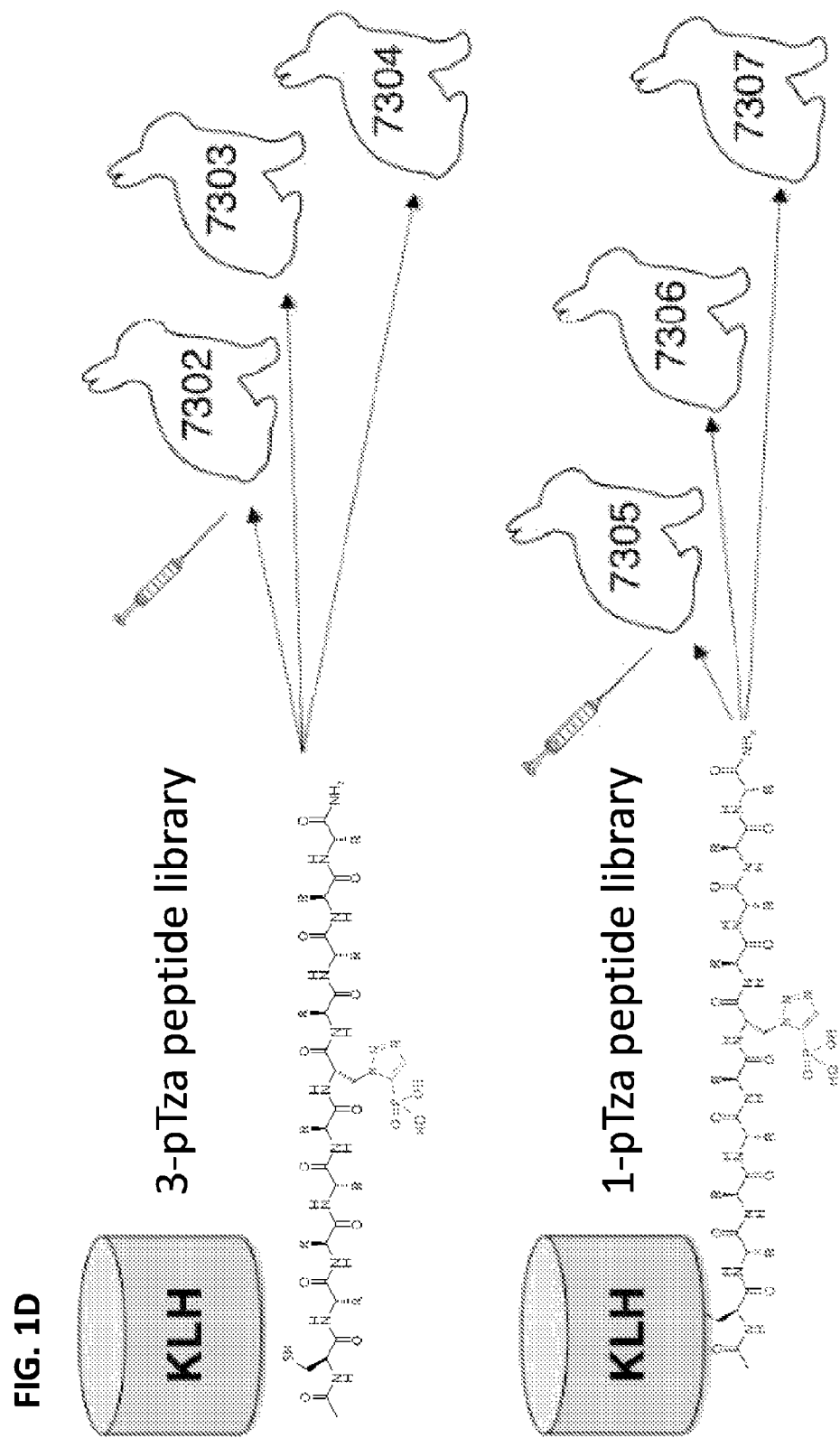

Incorporation of Non-Hydrolyzable pHis Analogues into Degenerate Peptide Libraries Previous attempts to make pHis antibodies using pHis itself as the antigen have been unsuccessful, presumably because the labile phosphoramidate (P-N) bond is hydrolyzed too rapidly after immunization to elicit an immune response (McAllister et al., Biochemical Society transactions 41, 1072 (August 2013)). Until recently, the difficulties in creating stable pHis peptides have precluded generation of pHis-specific monoclonal antibodies (mAbs). The development of non-hydrolyzable pHis analogues (Kee et al., Journal of the American Chemical Society, 132, 14327 (October 2010)) has allowed us to develop a novel strategy for generation of both 1-pHis- and 3-pHis-specific mAbs. Phosphonate (P—C) analogues of both isomers (1-phosphoryltriazolylalanine [1-pTza] and (3-phosphoryltriazolylalanine [3-pTza]) can be synthesized by combining the same starting materials (an azidoalanine derivative and an alkyne) in a click-chemistry reaction using different catalysts. Two peptide libraries were synthesized consisting of 1-pTza or 3-pTza flanked by randomized, neutral, small side chain amino acids (alanine [A] and glycine [G)]) to serve as immunogens to promote generation of sequence-independent anti-pHis antibodies (FIG. 1B). An unphosphorylated version of the peptide libraries (with His in place of the pHis analog (FIG. 1B) was also synthesized as a negative control. MS analysis of the peptide libraries confirmed that incorporation of Ala and Gly occurred randomly and fit with the expected distribution of calculated molecular weights for nine groups of peptides sharing the same composition of 0-8 Ala and/or Gly residues (FIG. 1C). The N-terminal Cys was used to ligate the pTza libraries to the carrier protein Keyhole limpet hemocyanin (KLH) and three rabbits were immunized for each pHis isomer to increase the chance of obtaining antibodies with the desired characteristics (FIG. 1D). Rabbits were immunized due to recent advances in rabbit hybridoma and monoclonal antibody (RabMAb) technology and unique advantages of the rabbit immune system including; strong immune response to small epitopes, ability to recognize posttranslational modifications with high specificity and pM affinity (Dei Tos et al., Amer. J. Clin. Path. 124, 295 (2005)).

Example 2

Figure 2D:
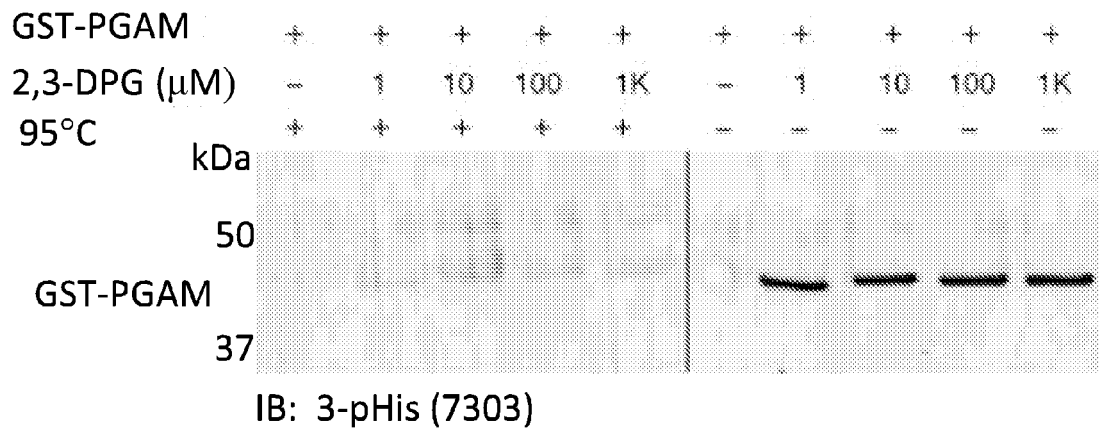
Figure 2E:
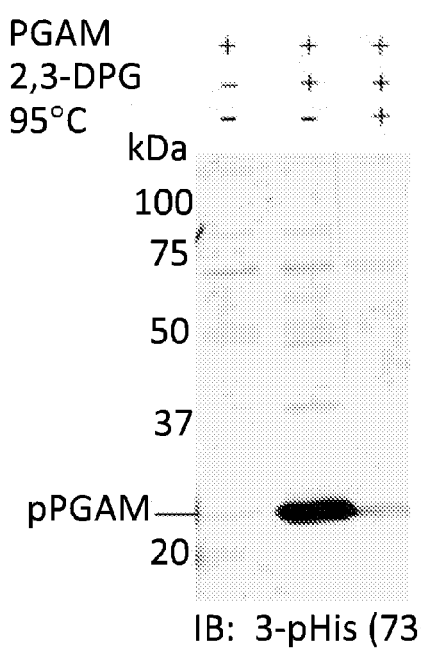

Generation of 3-pHis Antibodies and Development of PGAM in Vitro Screening Assay Bleeds from 3-pTza-immunized rabbits (7302, 7303 and 7304) were screened by dot blot (as described for 1-pTza antisera) and only the 3-pTza immunizing library was detected (FIG. 2A). PGAM is a glycolytic enzyme that converts 3-phosphoglycerate to 2-phosphoglycerate through a 3-pHis phosphoenzyme intermediate (Vander Heiden et al., 2010, Science 329, 1492-1499). Available crystal structures of pPGAM and PGAM co-crystallized with its phosphate donor (2,3-diphosphoglycerate [2,3-DPG]) show that only N3 of H11 is positioned to accept the phosphate from 2,3-DPG (PDB entries 1e58 and 2h4z, FIGS. 2B-2C). To determine if PGAM could be phosphorylated in vitro, GST-PGAM was incubated with 2,3-DPG [1 µM to 1 mM] (FIG. 2D). Identical samples were heated at 95° C. for 10 min and immunoblotting with 3-pHis antisera revealed a heat-sensitive, 45 kDa band that was absent when 2,3-DPG was omitted. PGAM was subsequently cloned into a bacterial expression vector that allowed cleavage of the GST for analysis of untagged protein. PGAM was purified from E. coli and incubated with or without 2,3-DPG. Autophosphorylation on H11 was confirmed by LC-MS/MS and immunoblotting with 3-pHis antisera revealed a heat-sensitive band at 25 kDa (FIG. 2E) that was abolished by mutagenesis of H11.

Figure 2F:
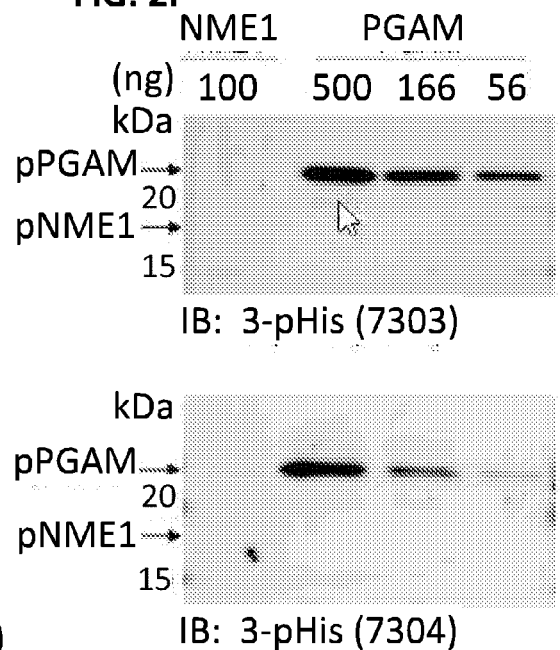
Figure 2G:
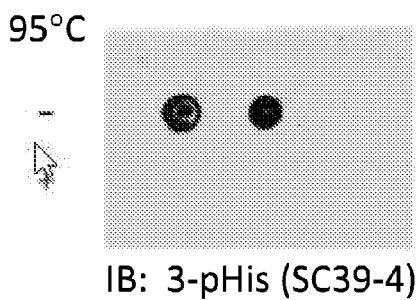

To confirm that 3-pHis antisera did not cross-react with 1-pHis, pNME1 was analyzed alongside pPGAM and no 1-pHis signal was detected (FIG. 2F). As observed for 1-pHis antisera, not all 3-pHis antisera that recognized the pTza analogues could bind pHis. Antisera from rabbits 7303 and 7304 (FIG. 2F), but not 7302 detected pPGAM. For this reason splenocytes were used from rabbits 7303 and 7304 to generate hybridomas expressing 3-pHis mAbs in collaboration with Epitomics (Burlingame, Calif.). To determine 3-pHis mAb sensitivity, in vitro phosphorylated PGAM was spotted directly on nitrocellulose. A representative immunoblot with 3-pHis mAb SC39-4 showed phospho-PGAM was detected down to ~10 ng in a heat-sensitive manner (FIG. 2G).

Example 3

Affinity Purification of Polyclonal Anti-1-pHis and Anti-3-pHis Antibodies

Figure 3A:
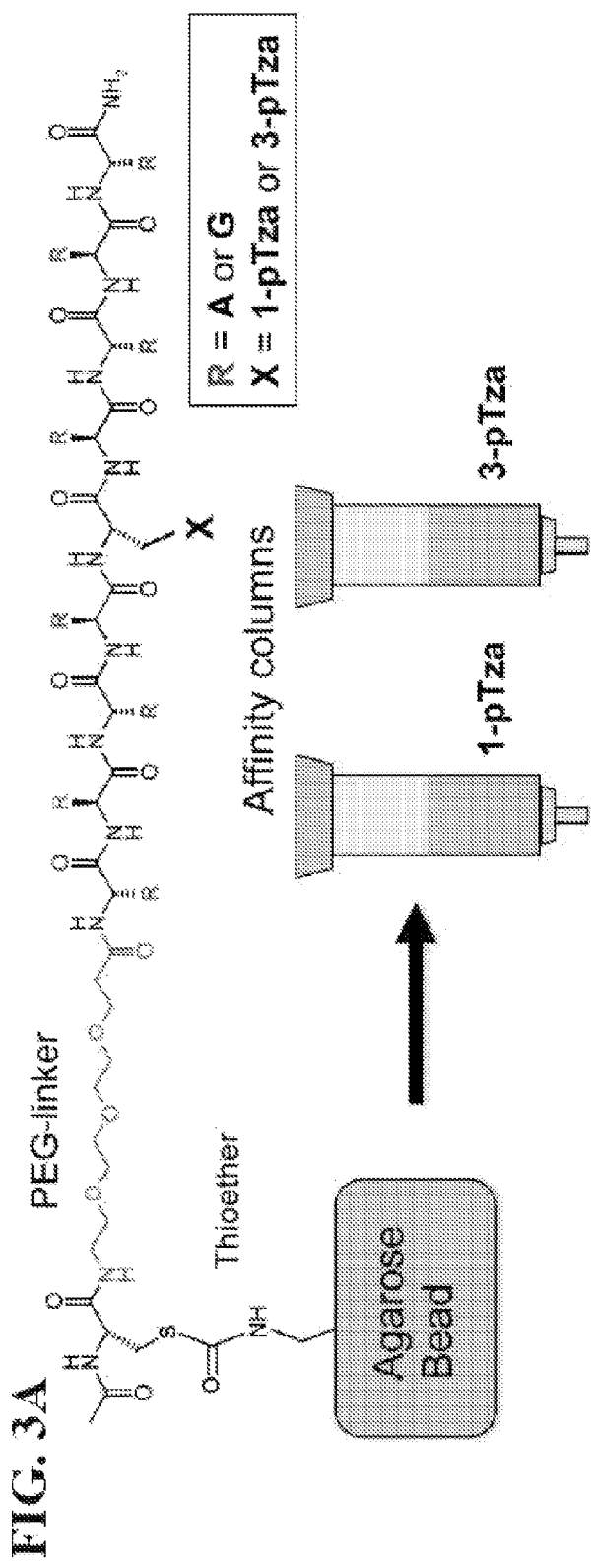
FIGS. 3A-3E. Affinity purification of anti-1-pHis and anti-3-pHis antibodies (FIG. 3A) Structures of the PEG-linker pTza peptide libraries used for affinity purification are shown covalently linked to agarose beads (Sulfolink coupling resin, Pierce) via a thioether bond with an N-terminal Cys residue. The agarose-linked pTza libraries were used in affinity columns to purifiy pHis antibodies from rabbit serum.
Figure 3B:
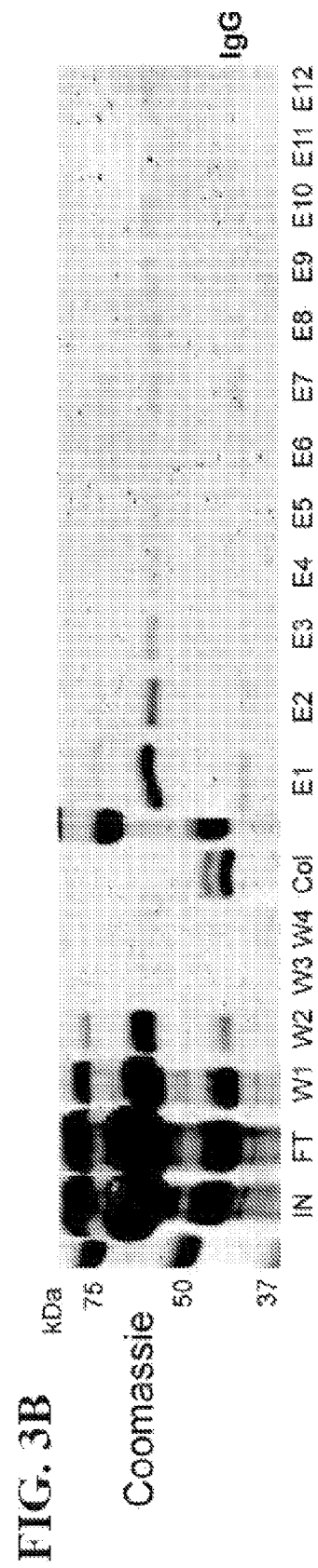
Figure 3C:
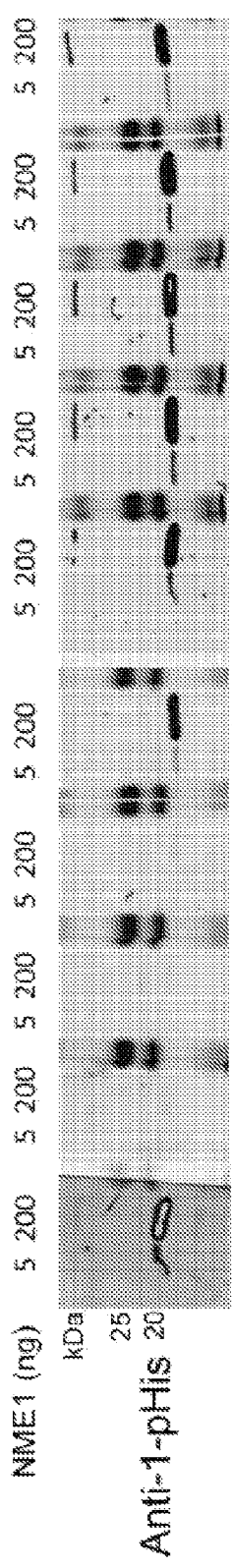
Figure 3D:
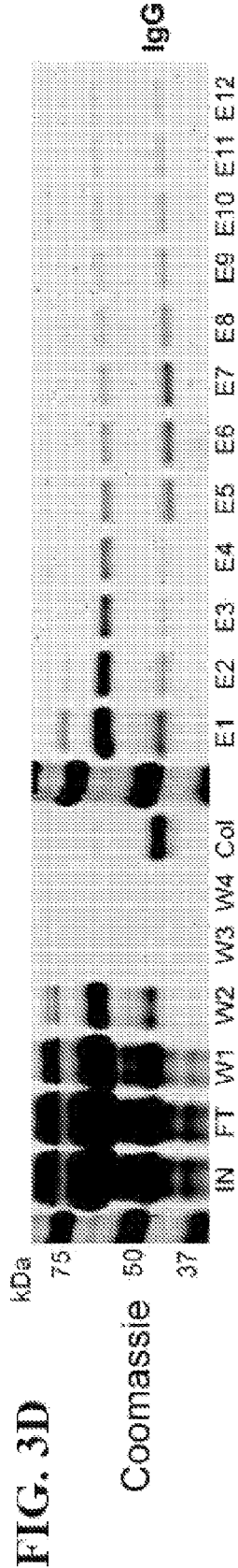
Figure 3E:
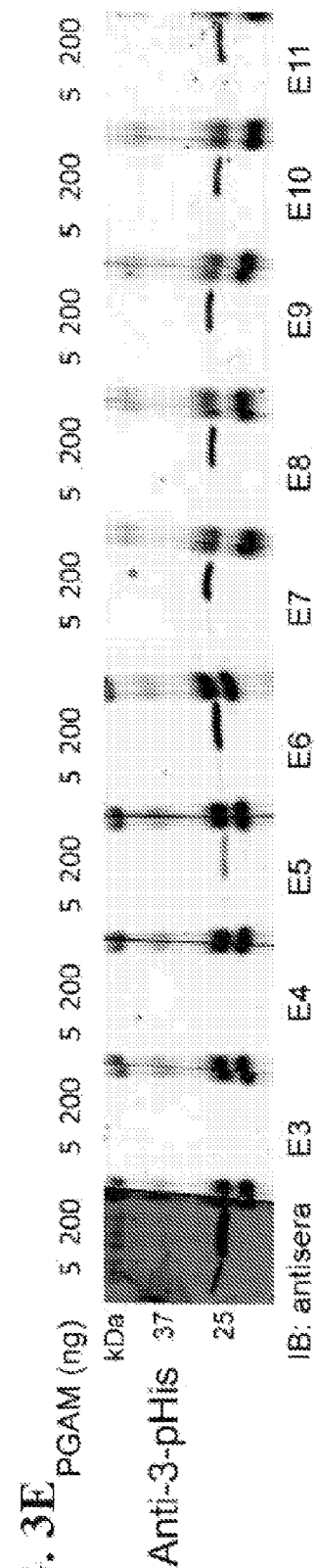

A second version of the 1-pTza and 3-pTza peptide libraries (FIG. 1B) was synthesized with a PEG-linker (polyethylene glycol) inserted between the N-terminal Cys residue and the Ala/Gly/pTza peptide (FIG. 3A). The PEG-linker libraries were immobilized on agarose beads and used to affinity-purify polyclonal pHis antibodies from rabbit antisera. By providing a greater distance between the agarose resin and the pTza analogue, the PEG-linker minimizes steric interference to improve binding of pHis antibodies. Fractions from the purification were analyzed by SDS-PAGE followed by Coomassie staining (FIGS. 3B and 3D) to determine which fractions contained IgG. Elution fractions (E3 to E11) were analyzed by immunoblotting of in vitro phosphorylated NME1 and PGAM for anti-1-pHis (rabbit 7305) and anti-3-pHis (rabbit 7303) antibodies respectively (FIGS. 3C and 3E). Fractions E6 to E11 (and beyond) contained anti-pHis antibodies that could detect as little as 5 ng phospho-NME1 or phospho-PGAM. Identical membranes were probed with crude antisera as a positive control.

Example 4 pTza Peptide Dot Blot Screening and Characterization of Anti-1-pHis and Anti-3-pHis Antibodies Synthetic peptide dot blot arrays were used to further demonstrate the pHis isoform specificity of the antibodies and determine if they have any amino acid sequence specificity. Peptides of defined sequence were chosen based on the best-characterized mammalian pHis proteins; ACLY, NME1, PGAM, histone H4, KCa3.1 and GNB1. Peptides were synthesized with either His, 1-pTza or 3-pTza flanked by 4 amino acids on either side. Serial dilutions of each peptide (500 ng to 160 pg) and the immunizing pTza and control His peptide libraries were spotted onto nitrocellulose and blotted with affinity-purified, polyclonal anti-1-pHis or 3-pHis antibodies (FIGS. 4A-4F).

Figure 4A:
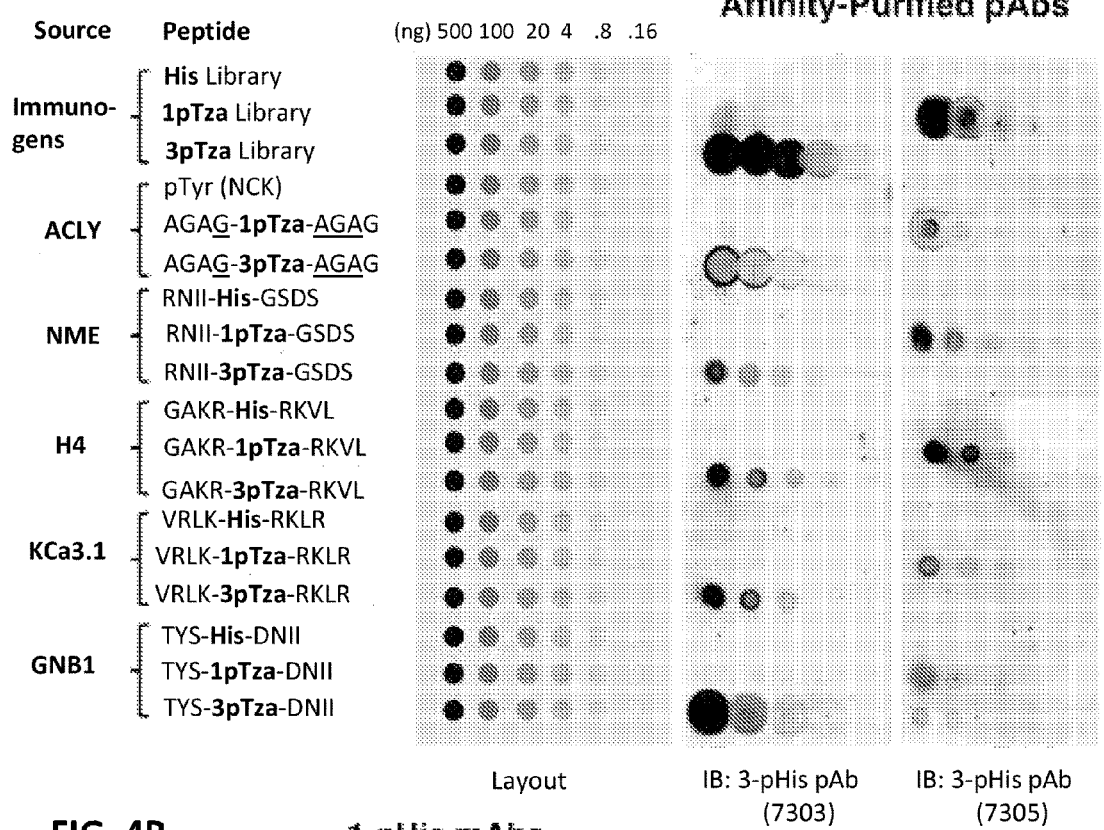
Figure 4B:
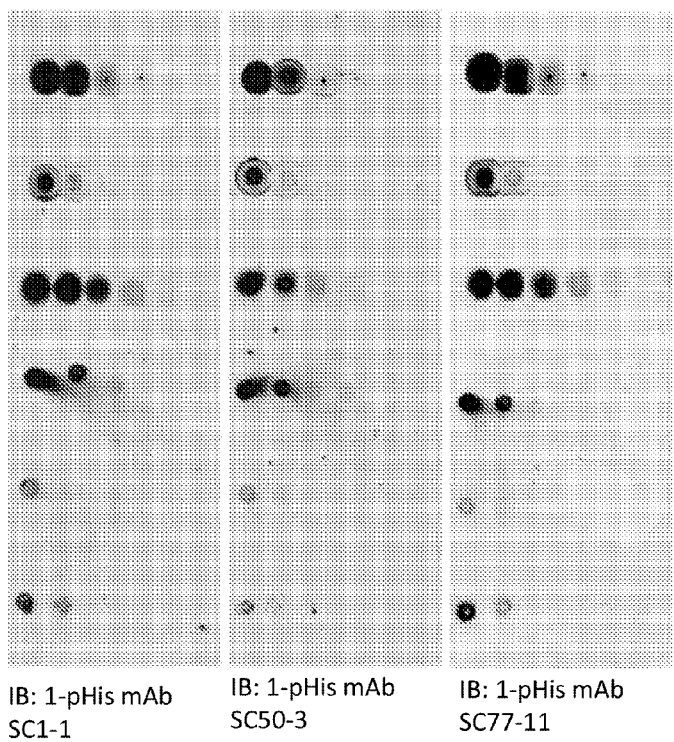

Synthetic 1-pTza and 3-pTza peptide dot blot arrays were used to confirm the pHis isoform specificity of the pHis mAbs and determine if they have any local amino acid sequence specificity. Peptides of defined sequence were synthesized based on the best-characterized mammalian pHis proteins; ACLY, NME1, PGAM, histone H4, KCa3.1 and GNB1. Peptides corresponding to the pHis sites in these proteins were synthesized with either His, 1-pTza or 3-pTza flanked by 4 amino acids on either side (see the table below). Serial dilutions of each peptide and the immunizing pTza and control His peptide libraries were spotted onto nitrocellulose and blotted with affinity-purified, polyclonal 1-pHis or 3-pHis antibodies. The 3-pHis antibodies bound only the 3-pTza peptides and the 1-pHis antibodies bound only the 1-pTza peptides, regardless of sequence (FIG. 4A). Identical membranes were probed with 1-pHis mAbs as part of our screening process to select mAbs with the broadest sequence recognition (FIG. 4B). The 1-pHis mAbs displayed similar binding profiles and detected as little as 1 ng of the NME1/2 H118 peptide. Each of the 1-pTza peptides tested was detected, suggesting these mAbs will be useful for detecting 1-pHis in a broad range of sequence contexts. Since 3-pHis mAbs did not cross-react with either 1-pTza or His peptides (FIG. 4A), peptide arrays consisting of just 3-pTza peptides were probed, including a PGAM peptide, to determine their sequence specificity (FIG. 4C). In contrast to the 1-pHis mAbs, the 3-His mAbs displayed some variation in binding profiles. 3-pHis mAb SC39-4 was able to detect all 3-pTza peptides down to 800 pg; however, binding to the KCa3.1 peptide was relatively poor (100 ng). 3-pHis mAb SC56-2 showed similar binding characteristics; however, it was better at detecting the KCa3.1 peptide (4 ng) while worse at binding the GNB1 peptide. SC44 detected the A/G motif peptide (based on ACLY) and the immunizing peptide library down to 160 pg and 800 pg respectively, confirming its sequence bias.

Example 5 pTyr Peptide Dot Blots and Immunoblotting Reveal No Cross-Reactivity of pHis mAbs and pHis mAbs Detect pHis Proteins in Mammalian Cell Lysates Since some of the first described pTyr mAbs cross-reacted with pHis (Frackelton et al., 1983, Mol Cell Biol 3, 1343-1352) and recently reported polyclonal pHis antibodies displayed only a 10-fold higher selectivity for pHis over pTyr (Kee et al., 2013, Nat Chem Biol 9, 416-421), the pHis mAbs were tested for cross-reactivity using synthetic pTyr peptides. Serial dilutions of pTyr peptides (Nck, and the Eck/EphA2 and FAK tyrosine kinases) were spotted on nitrocellulose along with their unphosphorylated counterparts. The pTyr mAb 4G10 detected only the pTyr peptides (FIG. 4D), whereas none of the peptides were detected by 3-pHis (FIG. 4E) or 1-pHis mAbs (FIG. 4F).

Figure 5A:
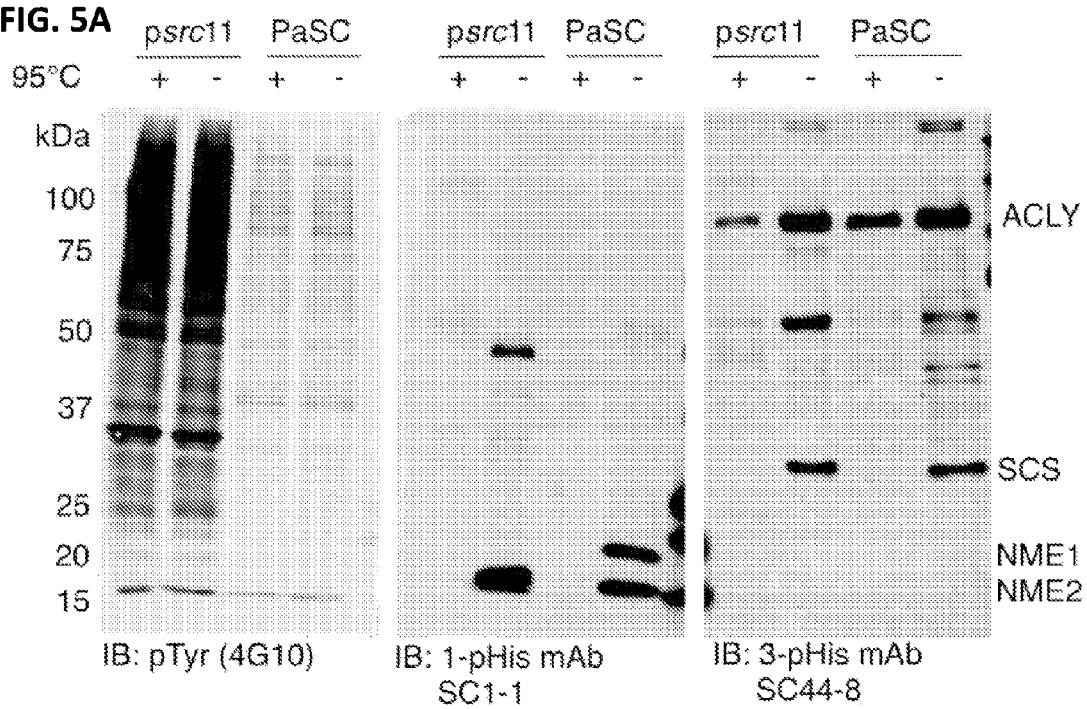
FIGS. 5A-5E. pHis Proteins, but not pTyr, are Detected in Mammalian Cells.

To test for pTyr cross-reactivity of the pHis mAbs on cell lysates, cultures of v-Src-transformed NIH/3T3 fibroblasts (psrc11 (Johnson et al., 1985, Mol. Cell. Biol. 5, 1073-1083)) were pre-incubated with 1 mM orthovanadate for 30 min to enhance pTyr signals. Non-transformed fibroblasts (pancreatic stellate cells PaSC) were tested in parallel as a negative control. To preserve pHis in cell lysates for analysis by immunoblotting, we adopted a modified SDS-PAGE method to maintain the sample pH above 8 to stabilize pHis. pTyr mAb 4G10 detected an elevated signal in the psrc11 cells but not in the PaSC negative control cells, but neither the 1-pHis nor 3-pHis mAbs detected the elevated pTyr signal in psrc11 cells (FIG. 5A).

Figure 5B:
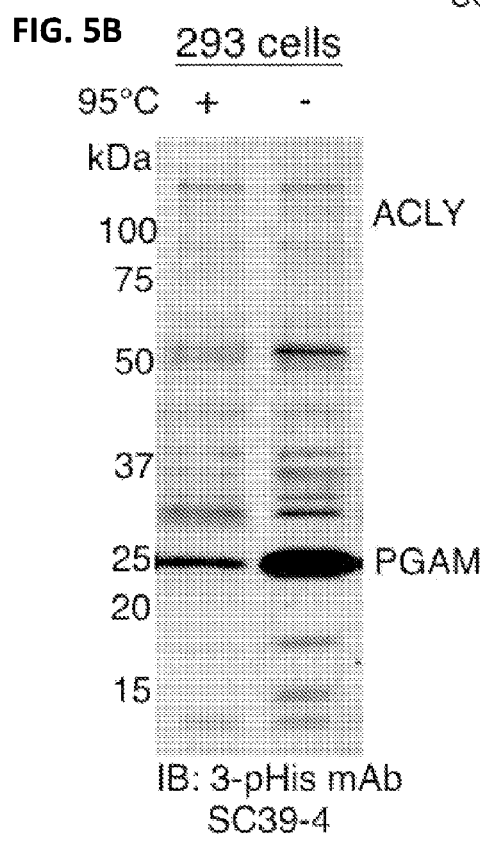
Figure 5C:
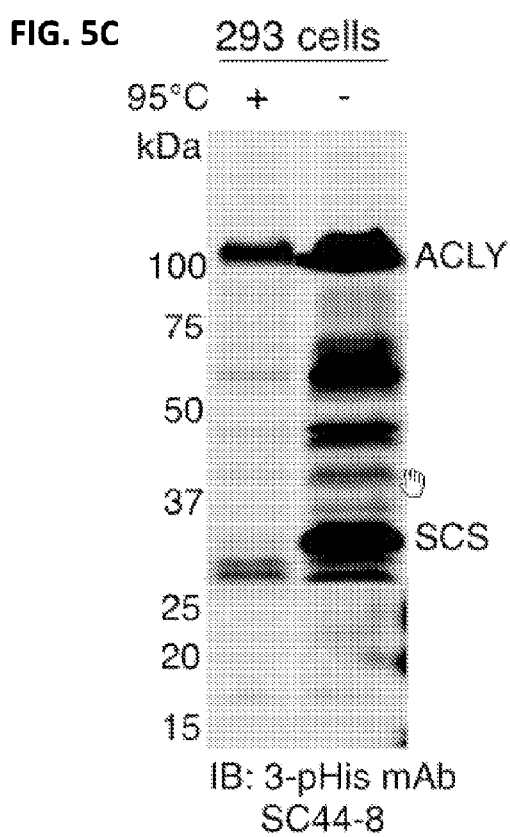
Figure 5D:
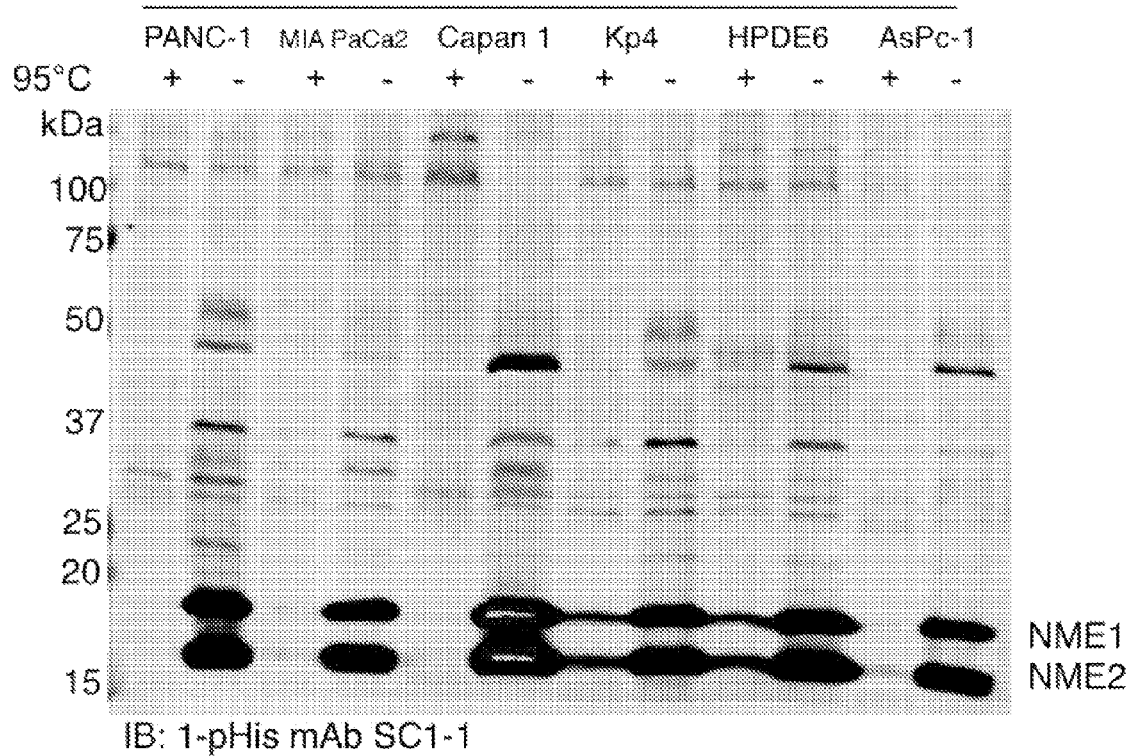
Figure 5E:
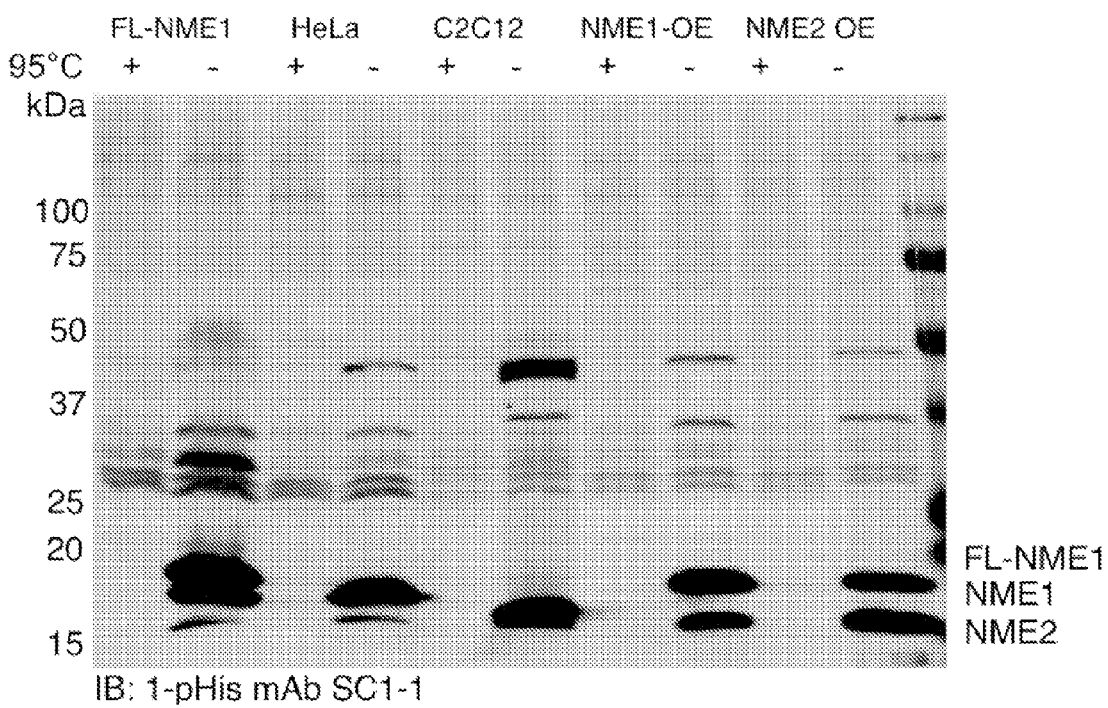

A number of heat-sensitive bands were detected in the psrc11 and PaSC lysates by 1- and 3-pHis mAbs. Lysates were immunoblotted from a variety of other mammalian cell lines to characterize the levels of pHis in different cell types. 3-pHis mAbs SC39-4 (FIG. 5B) and SC44-8 (FIG. 5C) were used to blot lysates from 293 cells, and 1-pHis mAb SC1-1 was used to blot lysates from several pancreatic cancer (PC) cell lines and HPDE6, a normal pancreatic epithelial cell line (FIG. 5D). Common patterns of heat-sensitive bands were observed indicating many proteins in these cancer cell lines are similarly regulated by 1-pHis modification. Lysates from FLAG-NME1 293, HeLa, C2C12, NME1 and NME2 over-expressing (OE) melanoma cell lines (Hamby et al., 2000, International J. Cancer 88, 547-553) were also blotted with 1-pHis mAb SC1-1 (FIG. 5E). 1-pHis was detected on NME family members in mouse, human and bacterial cells including; NME1, NME2, NME4, NME5 and NME7, despite differing sequences flanking the pHis residue, as well as the E. coli NME1 homolog NDK. While the major pHis proteins detected appear to be known enzymes (i.e., NME1/2 [1-pHis], PGAM, SCS and ACLY [3-pHis]), the detection of many unidentified, heat-sensitive bands, particularly by the 3-pHis mAbs, indicates they will be useful for identification of many pHis substrates.

Example 6

Screening of Anti-3-pHis Hybridomas

Figure 6A:
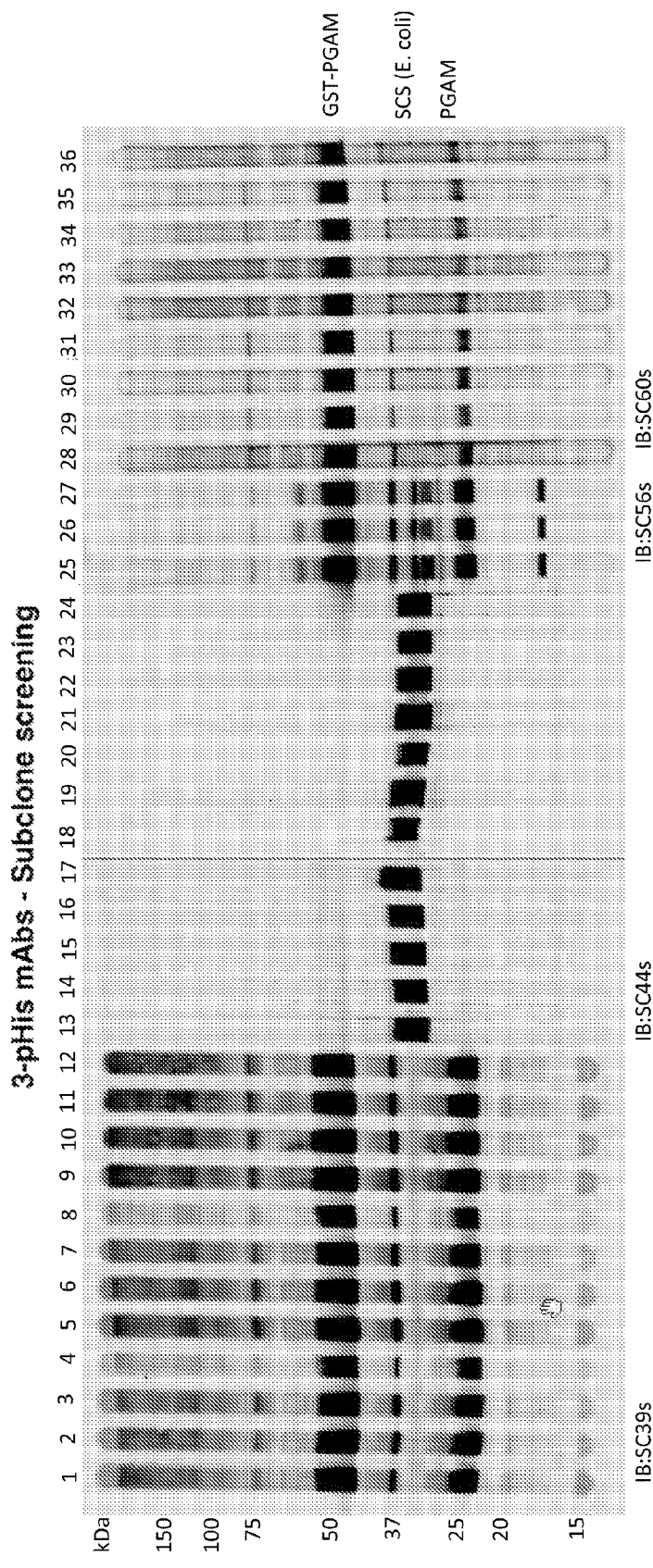

Anti-3-pHis hybridomas were generated from splenocytes harvested from rabbits 7303 and 7304 since antisera from both of these rabbits was able to specifically bind 3-pHis. Hybridomas generated from combined splenocytes from rabbits 7303 and 7304 were screened by ELISA using the 3-pTza peptide library. 30 ELISA-positive multiclonal cell lines were selected for secondary screening using 3-pHis-specific assays including pPGAM as described above. The four best 3-pHis mAb cell lines (MC39, MC44, MC56 and MC60) were subcloned resulting in up to 12 ELISA-positive subclones from each parental multiclone. E. coli transformed with a pGEX-PGAM plasmid were induced and crude lysates were supplemented with 2,3-DPG, spiked with purified, untagged PGAM and loaded on preparative minigels. High throughput, slot blotting was performed as described for 1-pHis mAb hybridomas (FIG. 6A).

Figure 6B:
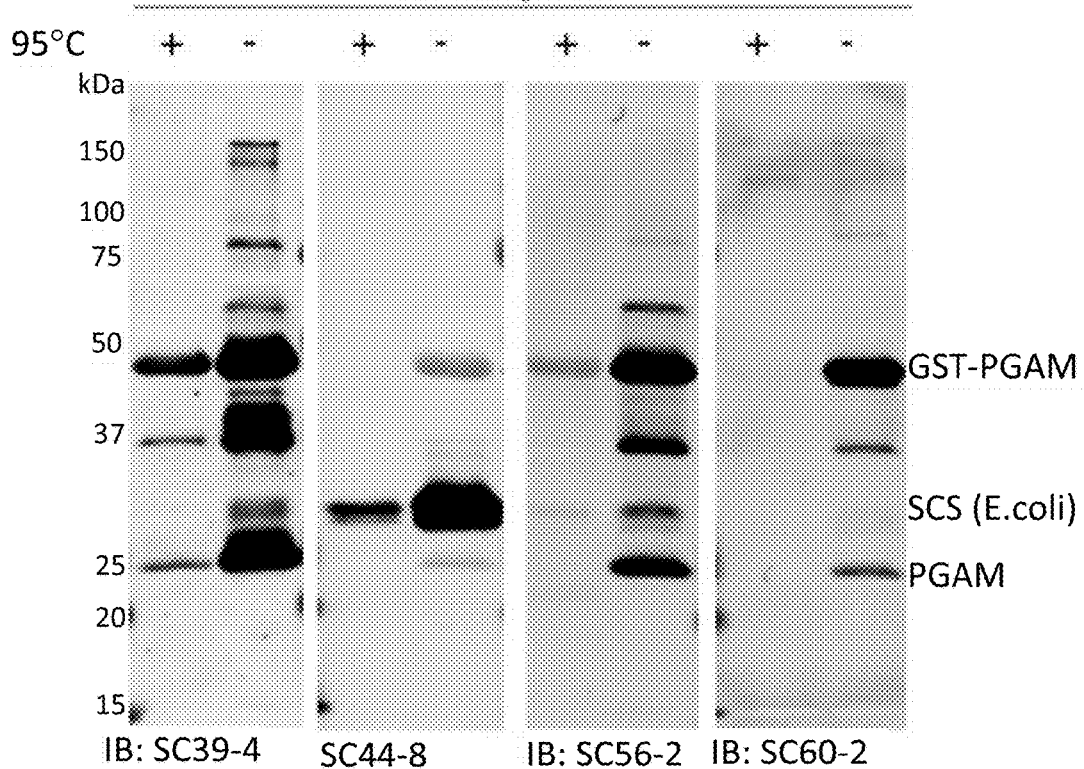
Figure 6C:
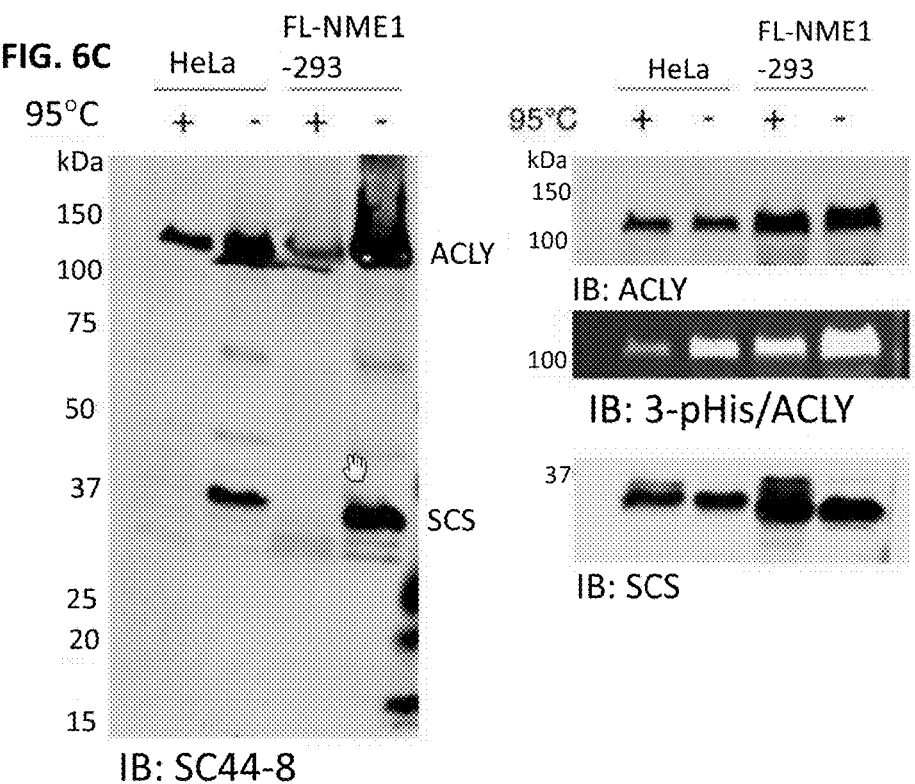
Figure 7A:
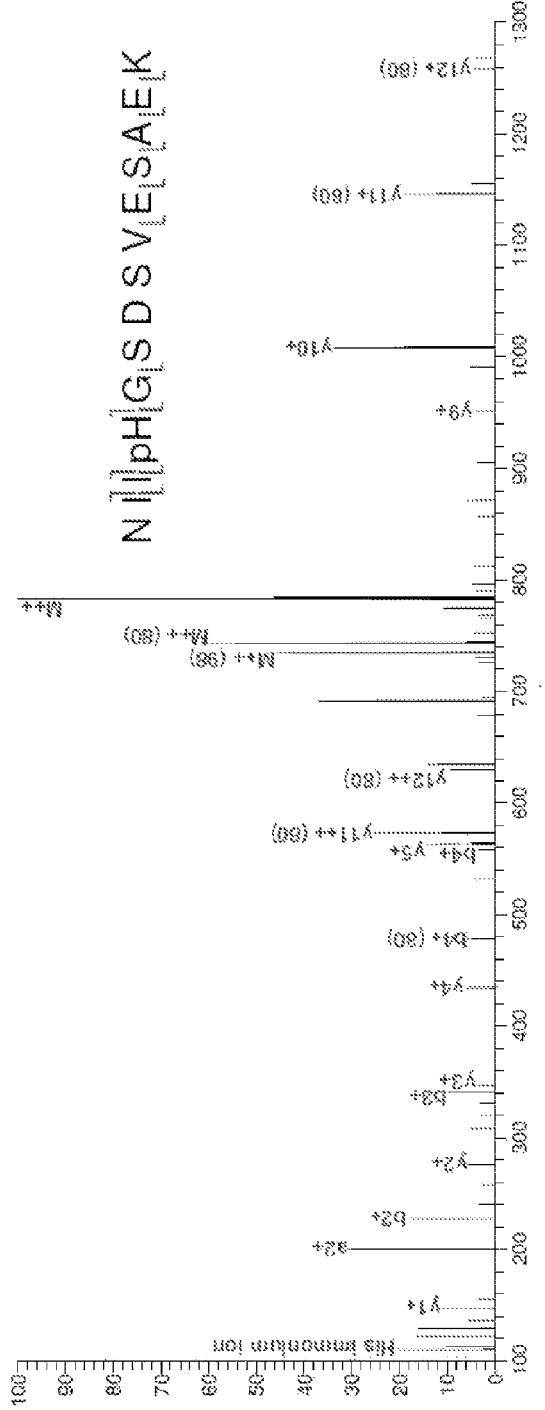
FIGS. 7A-7B. Mass spectra and phosphorylation site assignment of in vitro phosphorylated NME1 and PGAM.
Figure 7B:
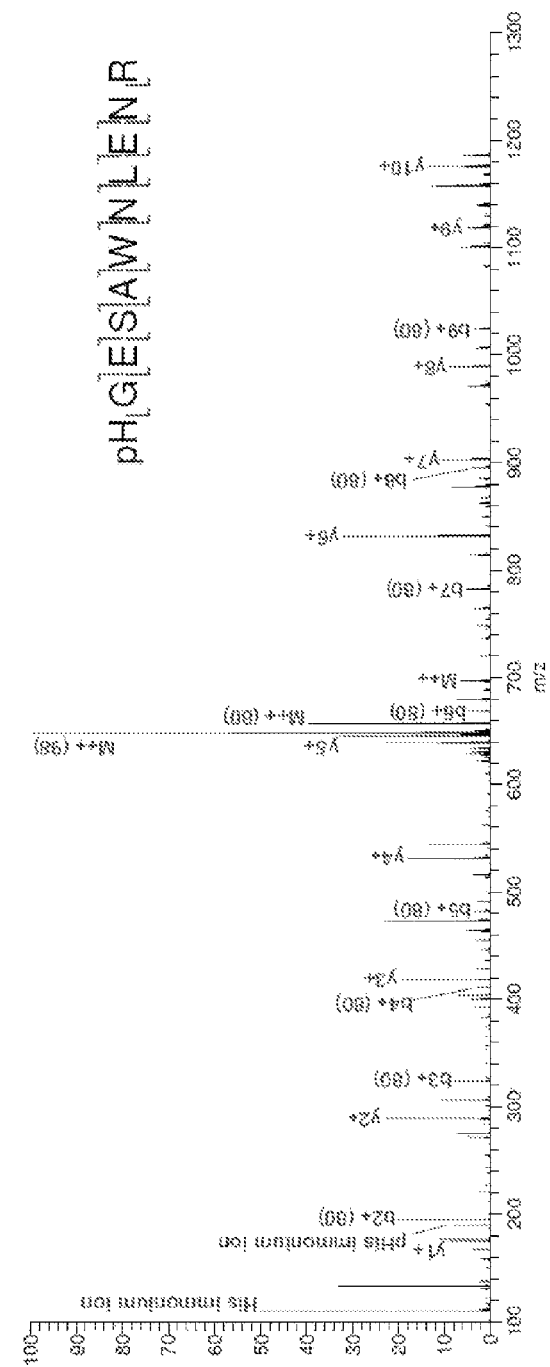

A small-scale screen was performed in parallel using identical E. coli lysates treated with and without heat (FIG. 6B). All of the detected bands were heat-sensitive, indicating the mAbs are 3-pHis-specific. Strong signals for the positive control proteins, GST-PGAM and PGAM (untagged) as well as many other heat-sensitive bands were detected by SC39s, SC56s and SC60s, suggesting that these mAbs lack strong sequence specificity, but do not produce an identical pattern of bands. In contrast, SC44s primarily detected a strong band corresponding to bacterial SCS (FIGS. 6A-6B). SCS also uses a 3-pHis phospho-enzyme intermediate (Fraser et al., 2000, J Mol Biol 299, 1325-1339), and SC44s detected both bacterial SCS and mammalian SCS and ACLY (FIG. 6C), which share the sequence motif; G-H-A-G-A (SEQ ID NO: 33) (FIG. 6D). Cell lysates prepared from a stably transfected HEK293 cell line expressing FLAG-NME1 were blotted with 3-pHis mAb SC39-4 and 3-pHis on endogenous pPGAM was detected, but not 1-pHis on FLAG-NME1, indicating the 3-pHis mAbs do not cross-react with 1-pHis generated in vivo (FIG. 6E). Sequence analysis of 3-pHis mAb $V_H$ and $V_L$ domains permitted the identification of SC39-4, SC56-2 and SC60-2 as unique, sequence-independent 3-pHis mAbs, as well as a distinct sequence-dependent mAb SC44-8 that has bias towards the A/G motif present in SCS and ACLY.

Example 7

Immunofluorescence of pHis Proteins Using Anti-3-pHis mAbs

Figures 8A, 8B:
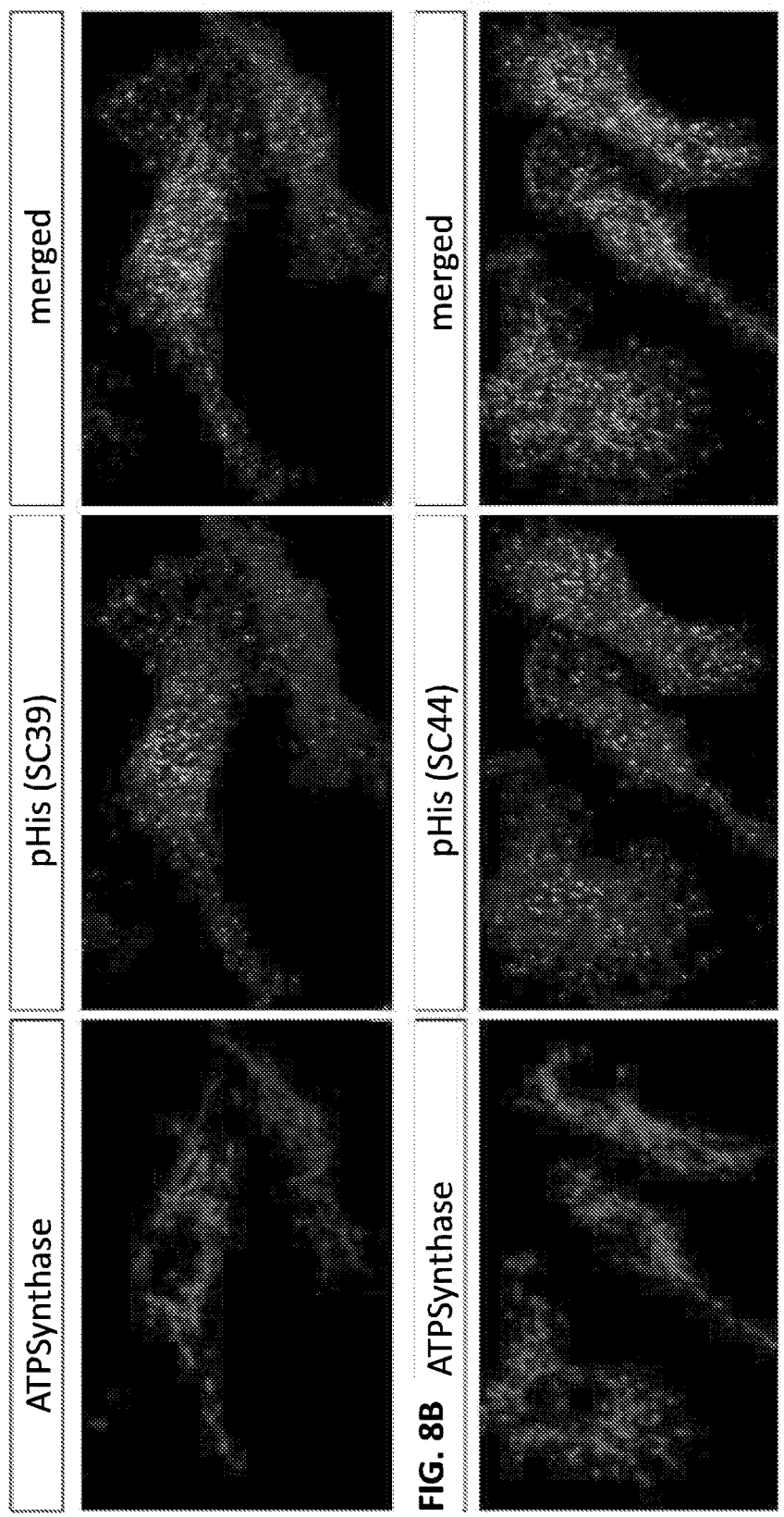
FIGS. 8A-8B. Primary murine macrophages were isolated from bone marrow and fixed with paraformaldehyde. Macrophages were co-stained with the anti-3-pHis mAb SC39-4 (FIG. 8A) or anti-3-pHis mAb SC44-8 (FIG. 8B) and anti-ATP synthase antibodies (a mitochondrial enzyme) to check for co-localization with mitochondria.

In addition to validating the anti-3pHis mAbs for immunoblotting, they were tested in other applications, including and immunofluorescence (IF). Primary murine macrophages were stained with our anti-3-pHis mAbs (FIGS. 8A and 8B). A staining pattern distinct from that obtained with anti-1-pHis mAb staining was observed, indicating that different sets of proteins are regulated by 1-pHis and 3-pHis in an isoform-specific manner. In contrast to the anti-1-pHis staining, punctate structures were observed throughout the cytosol, and especially pronounced puncta were visible in the nuclei of these cells. This indicates that some unknown, but specific compartments or organelles have increased 3-pHis signals compared with other regions of the cell. As a negative control, slides were boiled for 10 min in acetic acid and this treatment successfully abolished the observed anti-1-pHis staining.

Example 8

Figure 9A:
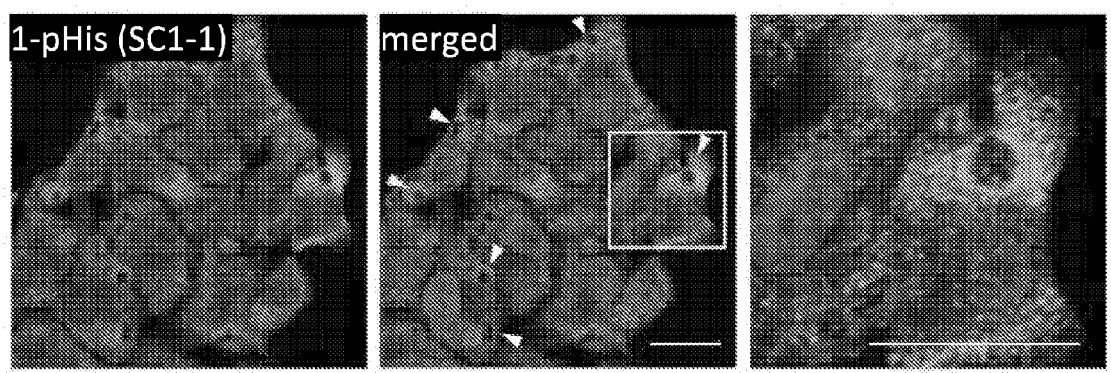
FIGS. 9A-9K. 1-pHis mAbs Negatively Stain Macrophage Phagosomes and 3-pHis mAbs Stain Centrosomes and Spindle Poles in HeLa Cells (FIG. 9A) HeLa cells were fixed with PFA and stained with 1-pHis mAb SC1-1. White arrows indicate acidic compartments.
Figure 9B:
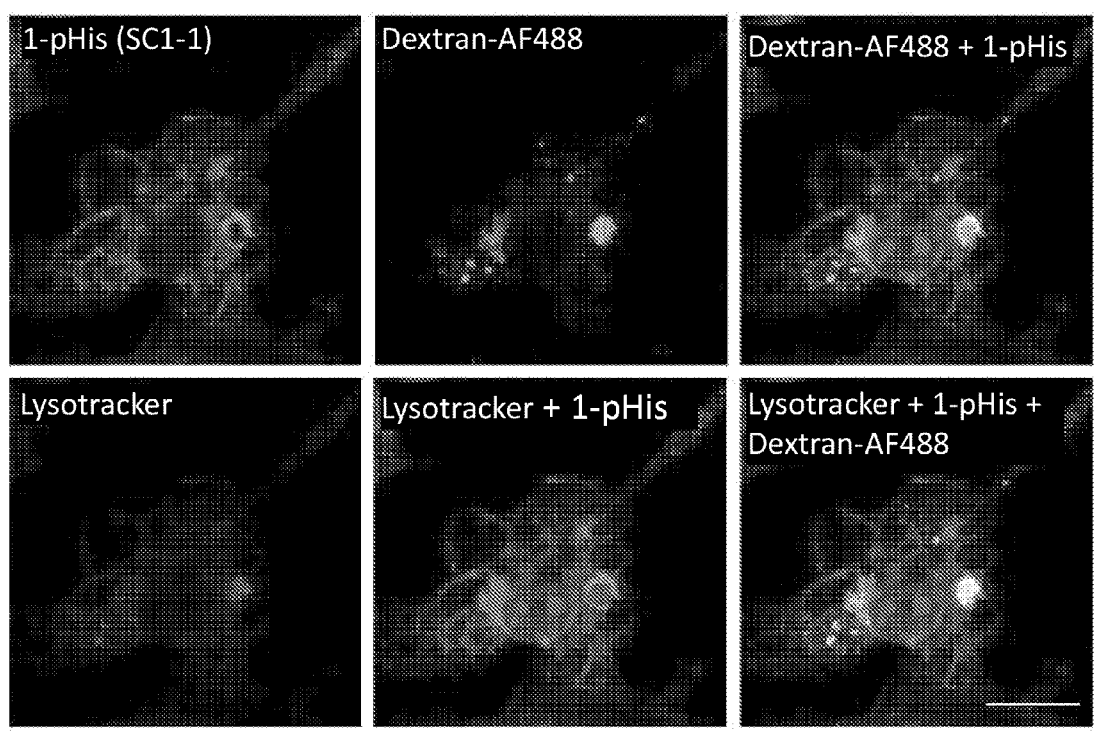
Figure 9C:
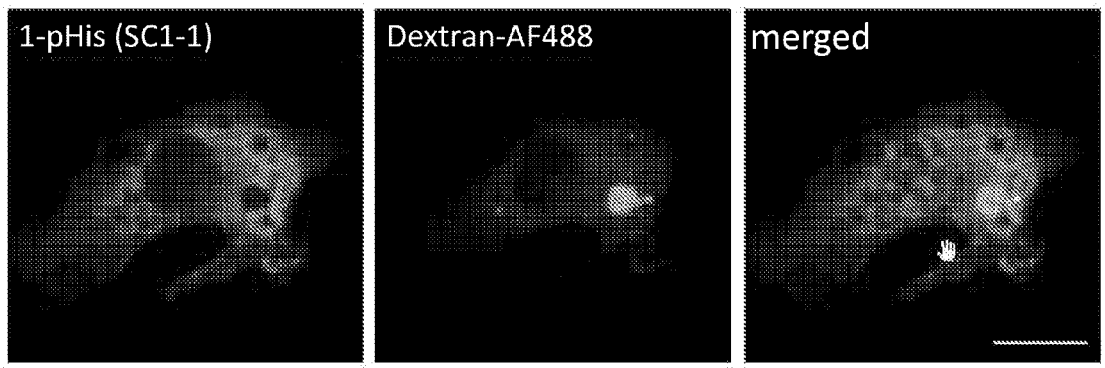
Figure 9D:
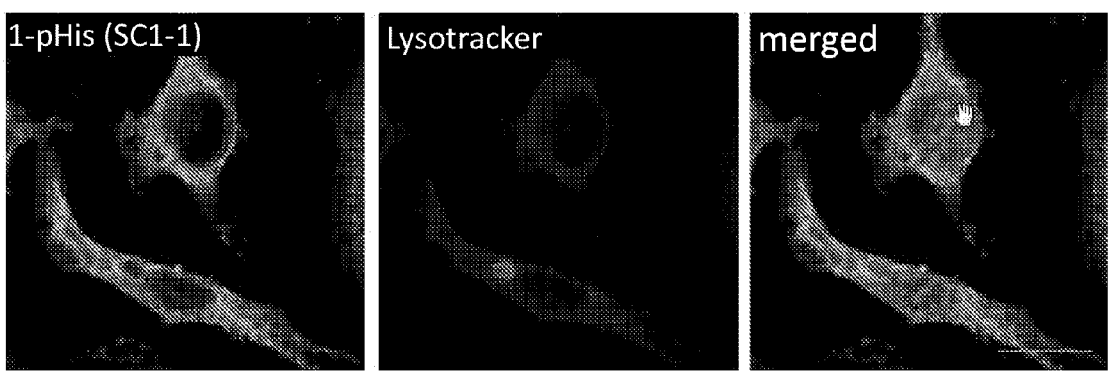
Figure 9E:
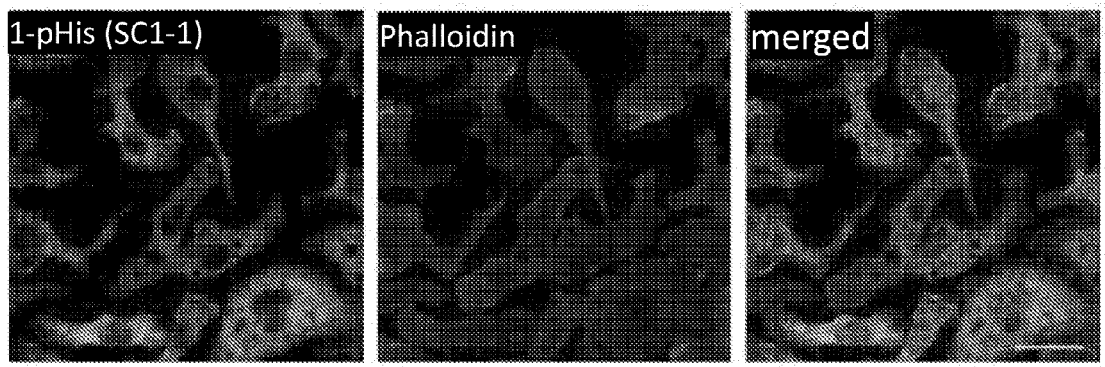
Figure 9F:
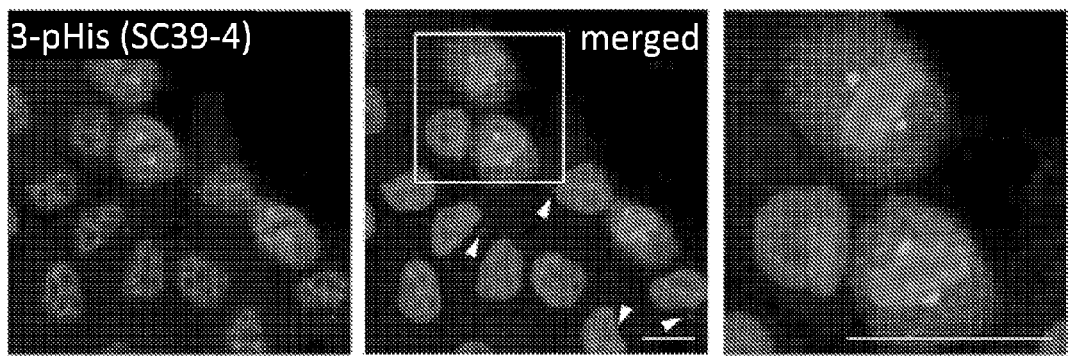

Immunofluorescence Staining Reveals Association of 1-pHis with Outer Membrane of Phagosomes To test the ability of these mAbs to detect pHis proteins by immunofluorescence staining, HeLa cells were stained with the 1-pHis mAb SC1-1. A distinct staining pattern in which most cells had a large (1-2 μm) compartment that stained strongly in the surrounding region but lacked interior pHis staining was observed (FIG. 9A). These might be acidic compartments such as phagosomes or autophagosomes, and this hypothesis was tested by using primary murine macrophages to look for specific staining of phagosomes. Macrophages isolated from bone marrow were incubated with fluorescently-labeled dextrans to track internalization into phagosomes. Cells were also incubated with LYSOTRACKER® prior to fixation to label acidic compartments. 1-pHis staining was absent in nuclei as well as the interior of phagosomes in macrophages co-labeled with the internalized dextrans and LYSOTRACKER®, but staining was pronounced in the regions surrounding these compartments (FIGS. 9B-9D). Remodeling of the actin cytoskeleton supports the extension of pseudopodia at sites of particle engulfment and F-actin assembles around nascent phagosomes. Co-staining with mAb SC1-1 and phalloidin-TRITC revealed a lack of co-localization of 1-pHis with actin filaments (FIG. 9E).

Example 9

Figure 9G:
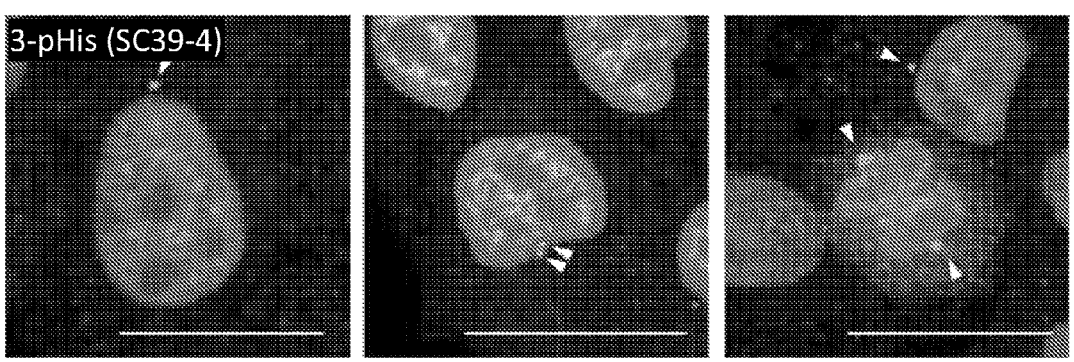
Figure 9H:
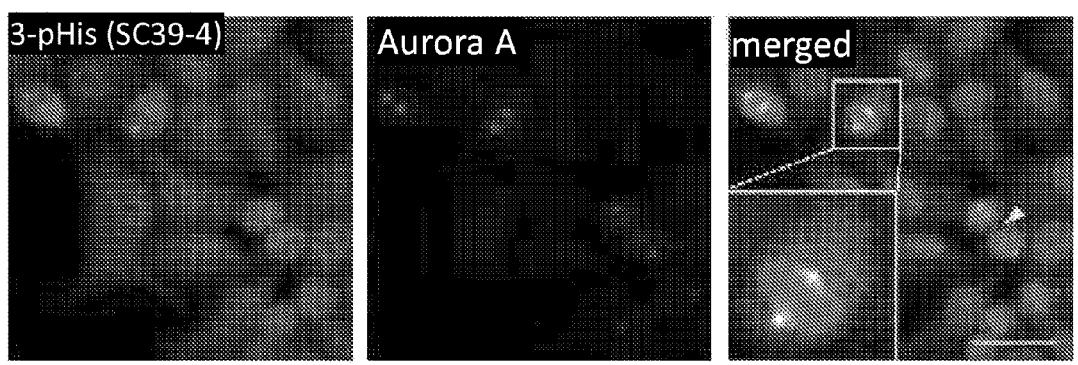
Figure 9I:
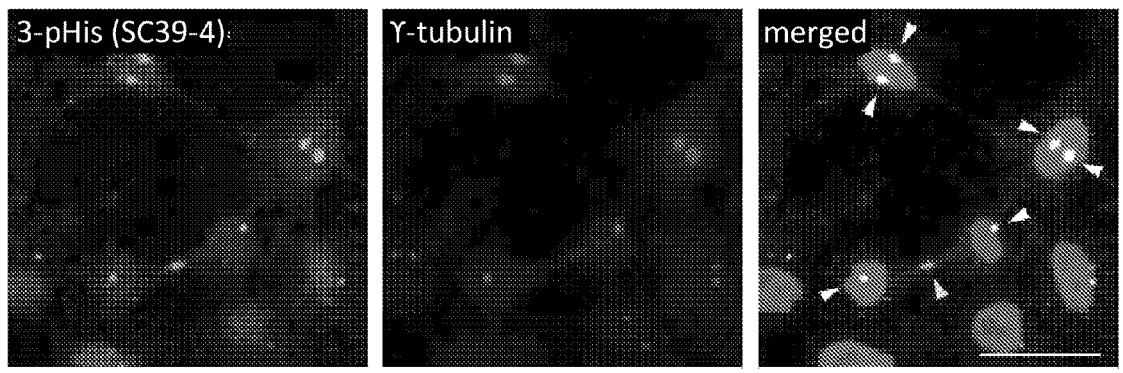
Figure 9J:
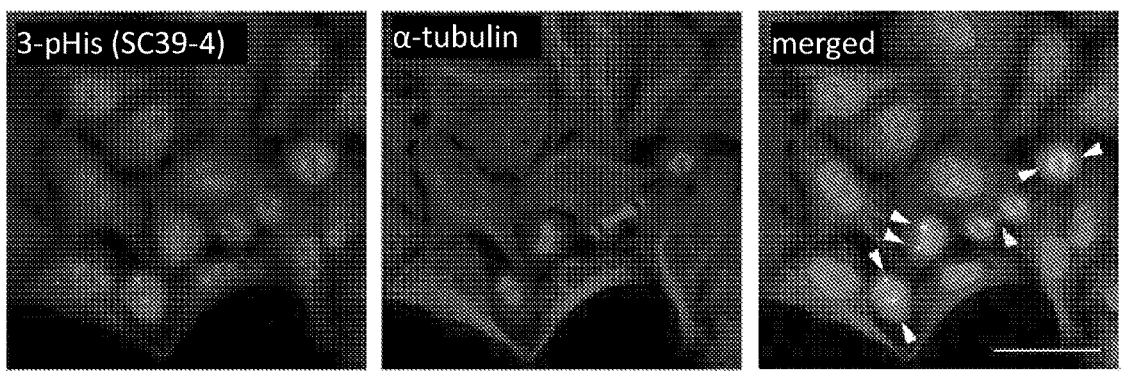
Figure 9K:
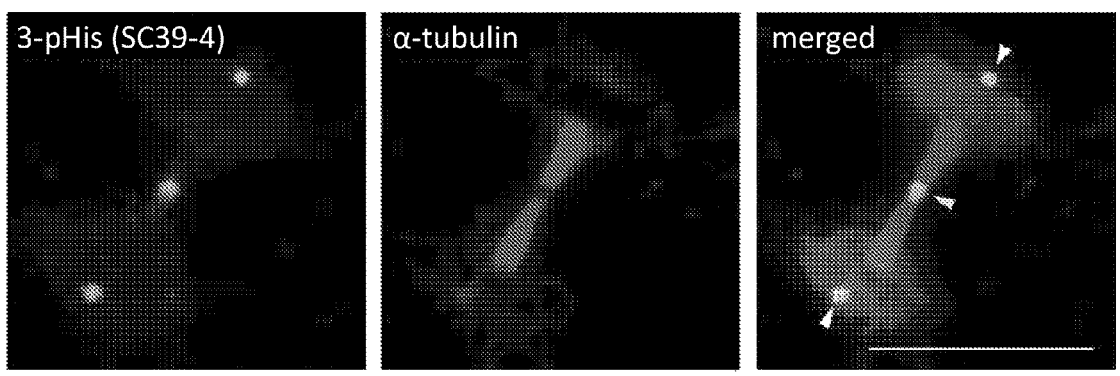
Figure 10D:
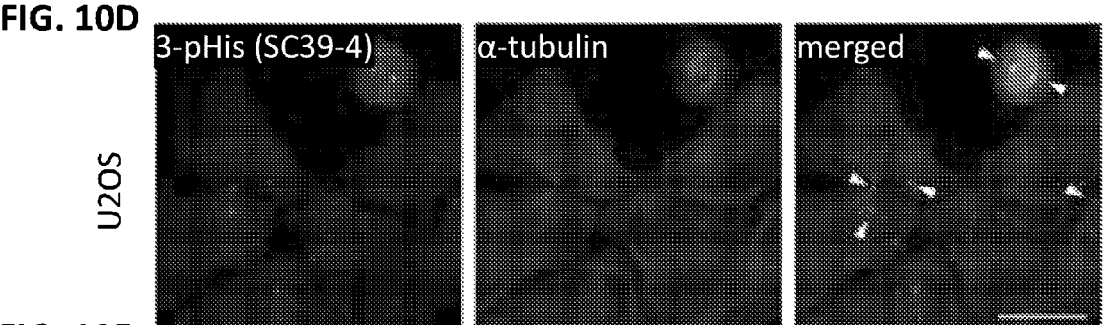
Figure 10E:
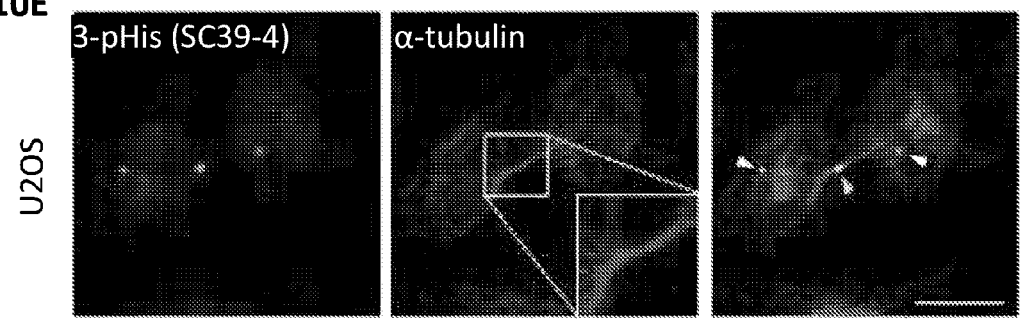
Figure 10F:
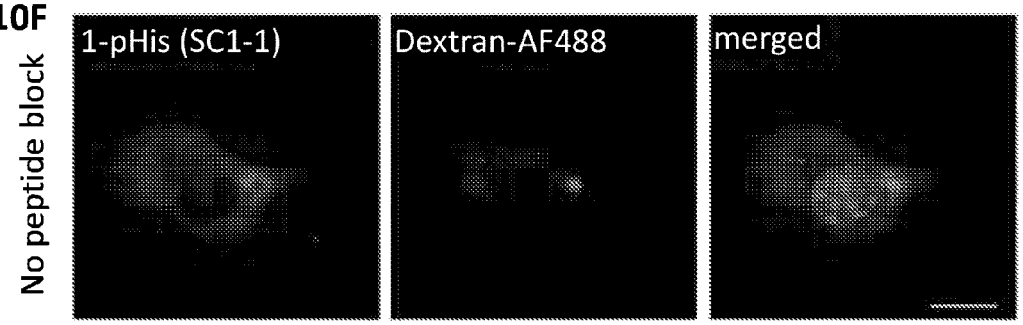
(FIGS. 10F-10J) 1-pHis mAb SC1-1 negative controls. Macrophages were stained with mAb SC1-1 that was pre-incubated with or without the immunizing peptide libraries for 30 min at RT with gentle agitation.
Figure 10G:
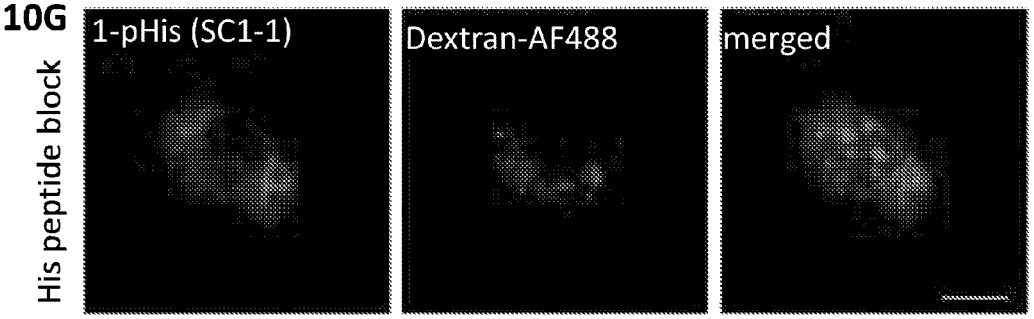
Figure 10H:
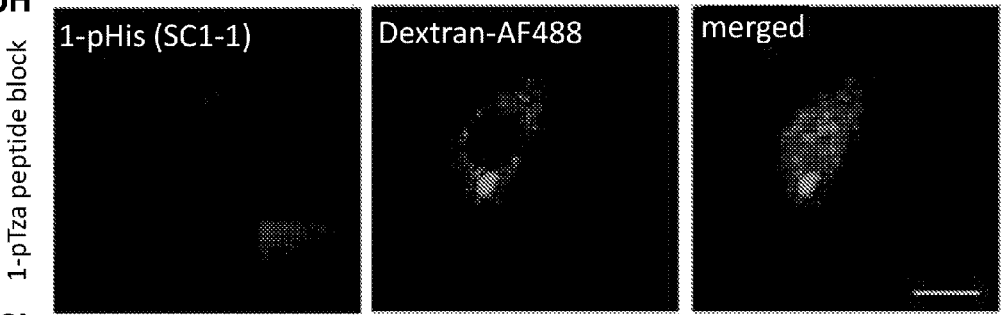
Figure 10I:
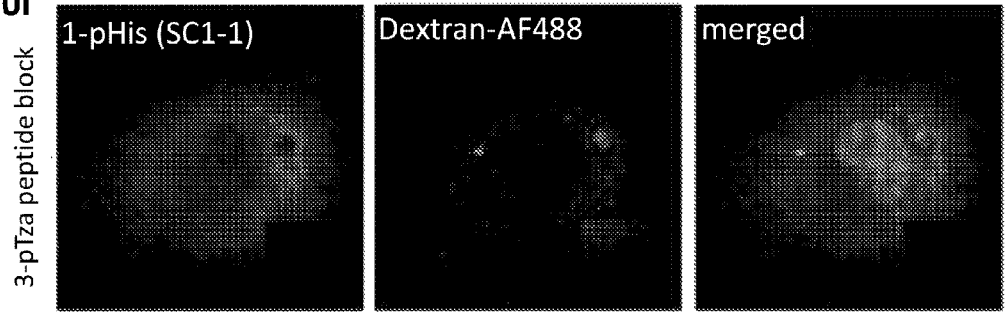
Figure 10J:
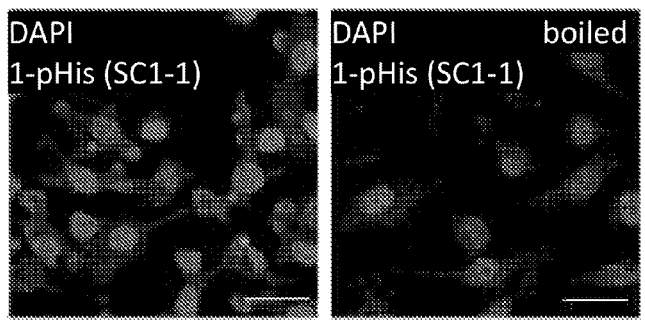
Figure 10K:
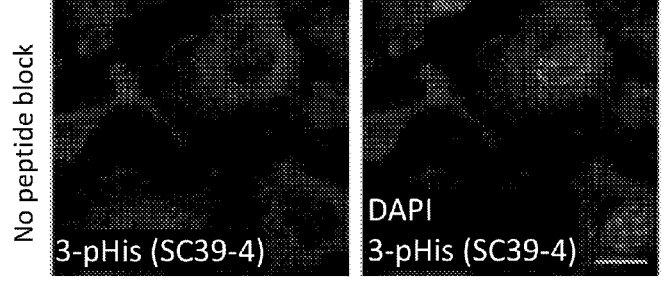
(FIGS. 10K-10O) 3-pHis mAb SC39-4 negative controls. Macrophages were stained with mAb SC39-4 that was pre-incubated with or without the immunizing peptide libraries.
Figure 10L:
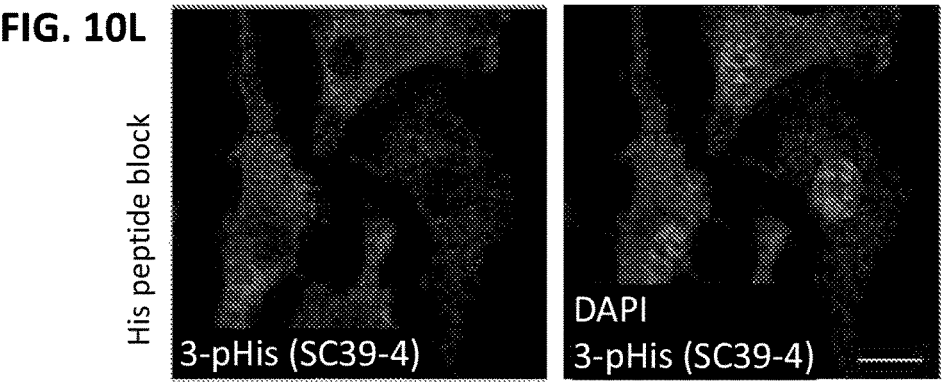
Figure 10M:
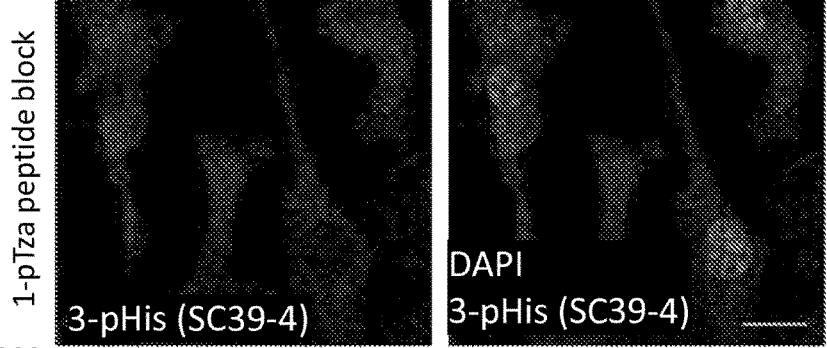
Figure 10N:
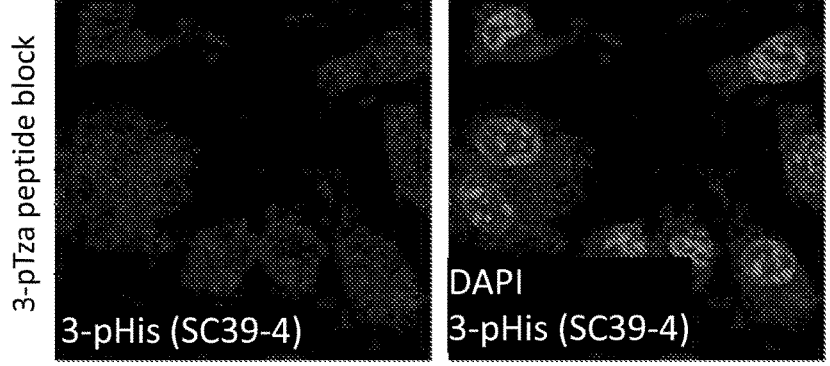
Figure 10O:
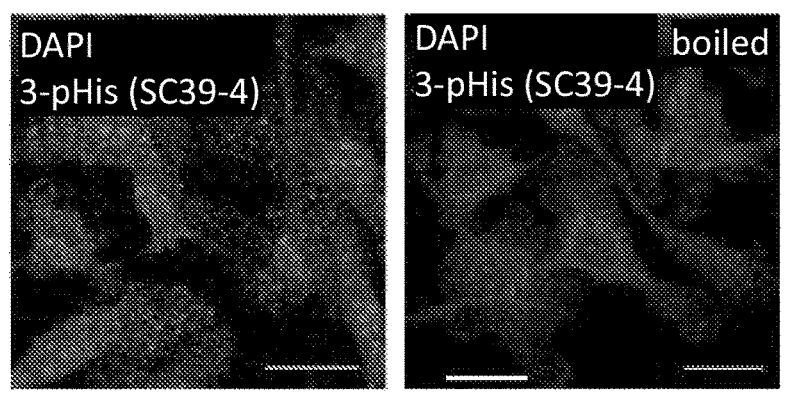
Figure 10P:
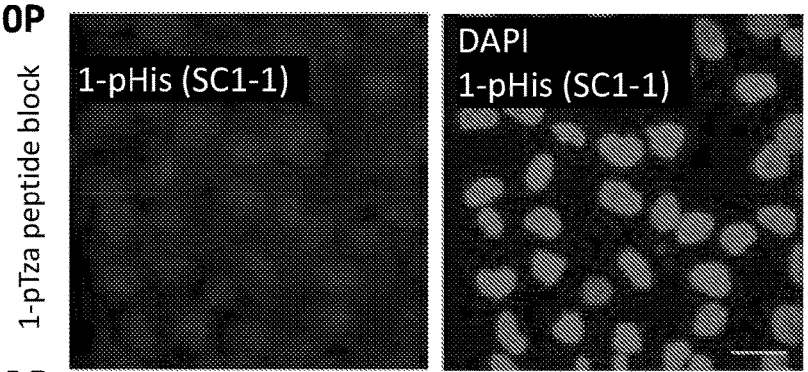
Figure 10Q:
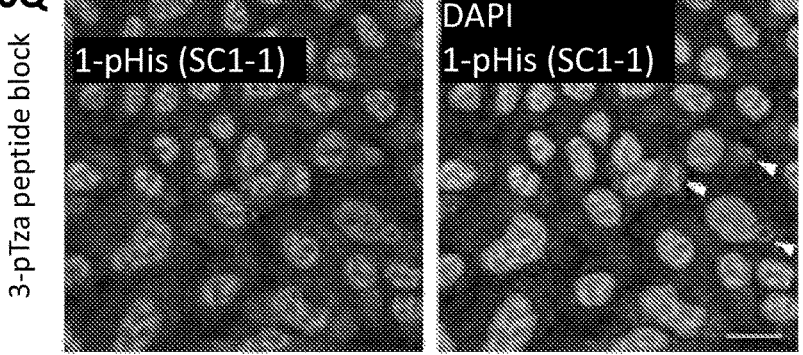
Figure 10R:
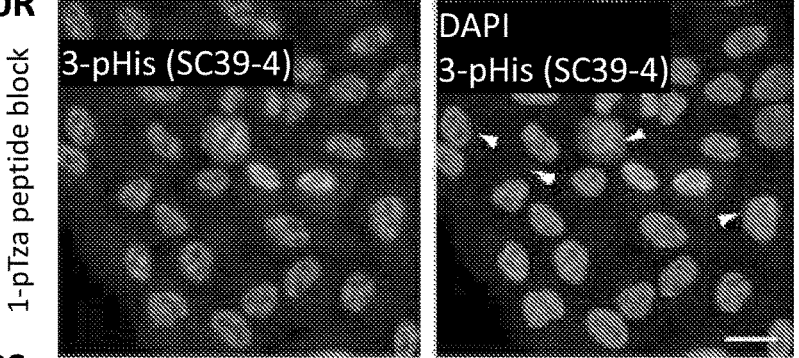
Figure 10S:
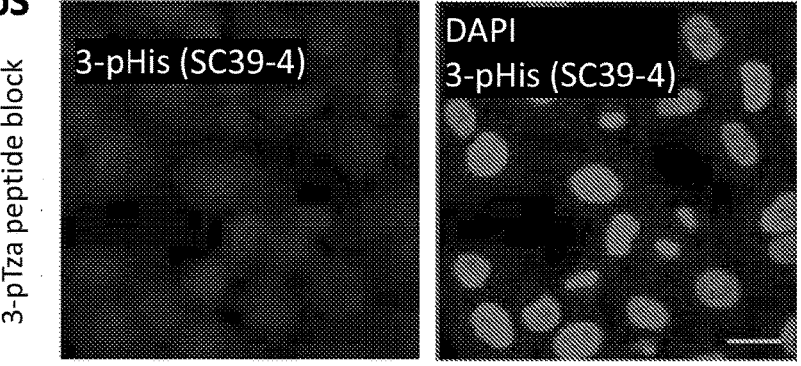

3-pHis mAb Immunofluorescence Reveals Staining of Centrosomes, Spindle Poles and Midbodies Macrophages stained with 3-pHis mAbs displayed a pattern distinct from 1-pHis staining. Punctate structures were observed throughout the cytosol; however, no co-localization was observed when antibodies specific for organelle markers (e.g., ATP Synthase, LC3, Rab5, α-tubulin and LAMP1) (FIGS. 10A-10B), were tested for co-staining. In contrast to macrophages, staining of HeLa cells with 3-pHis mAbs was primarily nuclear (though curiously absent from nucleoli) and distinctive cell cycle-dependent patterns were observed. Cells in prometaphase through telophase displayed remarkable 3-pHis staining of spindle poles (FIGS. 9F-9K). Interphase cells displayed staining of centrosomes and cells in prophase were observed with duplicated centrosomes (FIG. 9G). An apparent burst of 3-pHis signals was observed in dividing cells and this seemed to last from prometaphase through anaphase. To confirm this observation, HeLa cells were co-stained with 3-pHis mAbs and spindle pole markers Aurora-A and γ-tubulin (FIGS. 9H-9I). To demonstrate that 3-pHis mAbs stained primarily spindle poles and not spindles, cells were co-stained with α-tubulin (FIG. 9J). 3-pHis mAbs also stained structures devoid of Aurora-A, γ-tubulin and α-tubulin in both HeLa and U2Os cells and these appeared to be the midbody of cells in late telophase. (FIGS. 9H-9K and 10C-10E). A series of negative controls using the immunizing pTza peptide libraries were performed. Only the 1-pTza peptides could block 1-pHis staining (FIGS. 10F-10I, 10P-10Q) while only the 3-pTza peptides could block 3-pHis staining (FIGS. 10K-10N, 10R-10S). Additionally, boiling slides for 10 min in citrate buffer reduced both 1-pHis and 3-pHis staining (FIGS. 10J and 10O).

Example 10

Figure 11B:
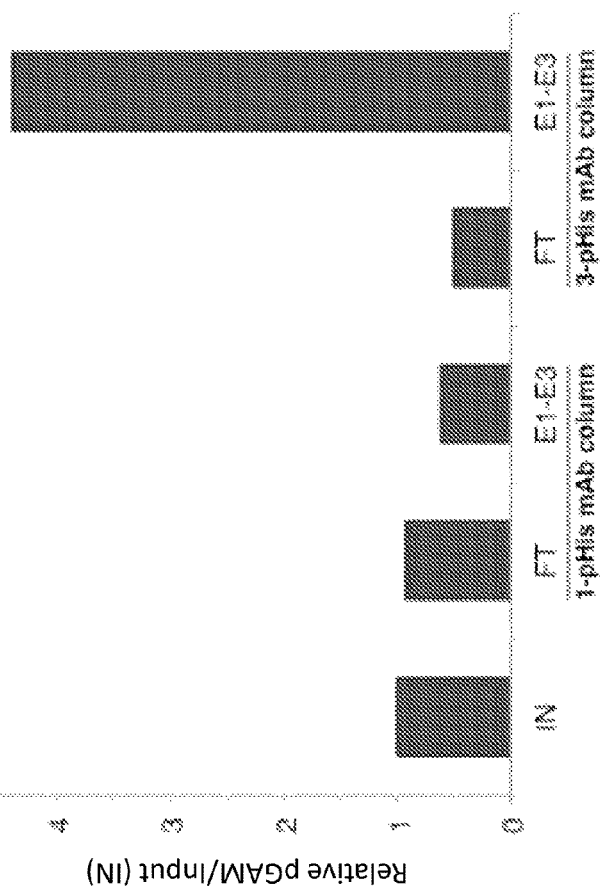
FIGS. 11A-11B. pHis mAb Immunoaffinity Purification of pNME1 and pPGAM Demonstrates pHis Isoform Selectivity and Enrichment of Cell Cycle Proteins. 1-pHis and 3-pHis mAb resins were and packed in chromatography columns. pPGAM and pNME1 were prepared separately by incubation with 1 mM 2,3-DPG or ATP respectively. Denatured pNME1 and pPGAM proteins (6 M urea, pH 10) were mixed together and diluted (1 M urea, pH 8) prior to incubation with the pHis mAb resins. The column input (IN), flow through (FT), last wash (LW) and elution fractions (E1, E2 and E3) were analyzed by immoblotting with 1-pHis mAb SC1-1 and NME1 antibodies or 3-pHis mAb SC39-4 and PGAM antibodies.
Figure 11A:
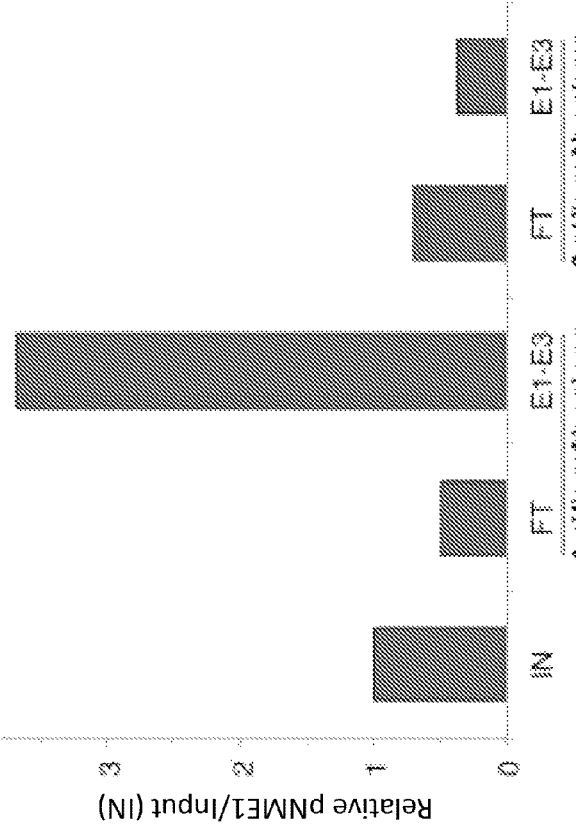

Enrichment and Identification of Proteins by pHis mAb Immunoaffinity Purification and SILAC LC-MS/MS Traditional immunoprecipitation methods are not amenable to pHis preservation and detection. A method for immunoaffinity purification of pHis substrates using immobilized pHis mAbs was developed. Reusable pHis mAb resins were packed in chromatography columns and used to enrich pHis phosphoproteins from cell lysates prior to analysis by LC-MS/MS. pNME1 and pPGAM were used to test the pHis isomer selectivity of the high density mAb columns. NME1 and PGAM were phosphorylated in vitro, denatured (6 M urea, pH 10), mixed together and incubated with either a 1-pHis or 3-pHis mAb column. Purification fractions were immunoblotted with 1- and 3-pHis mAbs as well as NME1 and PGAM antibodies and quantification demonstrates that pNME1 was enriched in elution fractions from the 1-pHis mAb column while pPGAM was enriched in elutions from the 3-pHis mAb column (FIGS. 11A-11B).

Example 11

Materials and Methods

Materials and Chemicals:

Reagents and their sources were as follows: FLAG-NME1/Nm23-H1 mammalian expression vector was from Addgene (Cat. 25000), GST-PGAM1 (Cat. H00005223-P01) was from Novus Biological, pGEX-6P-1 GST-fusion vector (Cat. 28-9546-48) and PreScission Protease (27-0843-01) were from GE Life Sciences, Rosetta𝑣 2 (DE3) competent cells (Cat. 71397), the pTyr mAb clone 4G10 (Cat. 05-321) was from EMD Millipore, 2,3-diphospho-D-glyceric acid pentasodium salt (Cat. SC-213964) and NME1 mAb (Cat. SC-136141) were from Santa Cruz, Alexa Fluor® 680 goat anti-rabbit IgG secondary antibody (Cat. A-21109), GST mAb (Cat. 13-6700), Oregon Green-Dextran®488 and LysoTracker Red DND-99 (Cat. L-7528) were from Life Technologies, goat anti-mouse IgG (H+L) secondary antibody, DyLight 800 conjugate (Cat. 35521) was from Pierce and Casein Blocking Buffer was from BioRad. Amicon Ultrafree 0.5-5K MWCO centrifugal filters (Cat. UFC500396), Immobilon-FL PVDF membranes (Cat. IPFL00010), the Mini-PROTEAN II Multiscreen Apparatus (Cat. 170-4017) and Casein blocking solution (Cat. 161-0783) was from BioRad. Glutathione resin (Cat. L00206) was from Genscript, Ampicillin, chloramphenicol, Adenosine 5'-triphosphate disodium salt (Cat. A2383), SDS, Trizma base, glycine, Isopropyl β-D-1-thiogalactopyranoside (Cat. 16758), Anti-FLAG M2 mAb (Cat. F1804), Anti-α-tubulin (Cat. T5168), Anti-γ-tubulin (T6557), Freund's Complete Adjuvant (Cat. F5881), Freund's Incomplete Adjuvant (Cat. F5506), iodoacetamide and octyl-β-D-glucopyranosideside (Cat. O8001) were from Sigma-Aldrich. Anti-Aurora A mAb was from Abcam (Ab13824). The SulfoLink Coupling Resin (Cat. 44999), the chemical crosslinkers DSS (Cat. 21555) and BS3 (Cat. 21580) and SILAC reagents (Cat. 89983 and 89990) were from Pierce/Thermo Scientific. All protein electrophoresis equipment including; Four Gel Caster (Cat. SE275), Mighty Small II Mini Deluxe Vertical Unit (Cat. SE260-10A-.75), Mighty Small Mini Transfer Tank (Cat. TE22) were from Hoefer, RPMI 1640 and 1% Glutamax (Cat. 35050-061) were from Gibco/Life technologies (Cat. 11875-119), Rabbit Hybridoma Supplement A was from Epitomics/AbCam (Cat. EP-401), cell culture grade 55 mM 2-Mercaptoethanol was from Invitrogen (Cat. 2198-023), IS-MAB-CD Serum-free medium was from Irvine Scientific (Cat. 91104) and 1% antibiotic/antimycotic solution was from Cellgro (Cat. 30-0004-CI). Tris(2-carboxyethyl)phosphine hydrochloride (TCEP) was from Roche Applied Science. Paraformaldehyde (PFA) was from Electron Microscopy Sciences (Cat. 15710).

Immunization of Rabbits

New Zealand White rabbits (three per antigen) were immunized using a standard prime-boost regimen and pre-immune serum was collected from each rabbit prior to immunization. The pTza peptide libraries were coupled to KLH, diluted to 1 mg/ml and stored in 1.5 ml aliquots at −20° C. For the primary immunization, Freund's Complete Adjuvant (0.5 ml per rabbit) was emulsified with antigen (0.5 ml per rabbit) using 5 ml syringes. Antigens were administered via intradermal injection of 50 µl at 20 sites on the back. Every three weeks, subsequent boosts were administered intradermally in Incomplete Freund's Adjuvant. Bleeds were collected in 10 ml tubes from the central ear artery ten days after each boost. Rabbit antisera was collected after spinning down blood (2,400×g for 10 min at 4° C.) that was allowed to clot for 24-48 hr. Antisera was frozen at −20° C. for long term storage.

Synthetic Peptide Synthesis:

Sequences of synthetic peptides and pTyr phosphopeptides used in this study are as follows; Nck pY105 (CGER-LpYDLNMPAYVK, SEQ ID NO: 10), Nck Y105 (CGER-LYDLNMPAYVK, SEQ ID NO: 11), Eck (Ephrin A2) pY588 (CLKPLKTpYVD, SEQ ID NO: 12), Eck (Ephrin A2) Y588 (CLKPLKTYVD, SEQ ID ON: 14) and FAK pY397 (AVSVSETDDpYAEIIDEEDTYT, SEQ ID NO: 14). Peptides were synthesized using Fmoc solid phase synthesis.

1-pTza and 3-pTza peptides are shown below. All pTza peptide and peptide intermediates were prepared according to previously published procedures (McAllister and Webb, 2012, Org Biomol Chem 10, 4043-4049). Chemical structures of peptide intermediate 1a and Peptide 3B are provided below. Chemical structures of peptide intermediates (peptide 1b and 1c) and Peptide-3C are also provided below. The peptides used in dot blots screening of pHis antibodies, related to FIG. 4A are shown below.

| Peptide | Sequence | Method | SEQ ID NO: | Protein Name-pHis site |
|---|---|---|---|---|
| Peptide-1A | H$_2$N-Ala-Gly-Ala-Gly-His-Ala-Gly-Ala-Gly-NH$_2$ | A | 15 | ACLY-like H760 |
| Peptide-1B | H$_2$N-Ala-Gly-Ala-Gly-1-pTza-Ala-Gly-Ala-Gly-NH$_2$ | B | 16 | ACLY-like H760 |
| Peptide-1C | H$_2$N-Ala-Gly-Ala-Gly-3-pTza-Ala-Gly-Ala-Gly-NH$_2$ | B | 17 | ACLY-like H760 |

-continued

| Peptide | Sequence | Method | SEQ ID NO: | Protein Name-pHis site |
|---|---|---|---|---|
| Peptide-2A | H₂N-Val-Leu-Ile-Arg-His-Gly-Glu-Ser-Ala-NH₂ | A | 18 | PGAM H11 |
| Peptide-2B | H₂N-Val-Leu-Ile-Arg-1-pTza-GlLy-Glu-Ser-Ala-NH₂ | C | 19 | PGAM H11 |
| Peptide-2C | H₂N-Val-Leu-Ile-Arg-3-pTza-Gly-Glu-Ser-Ala-NH₂ | C | 20 | PGAM H11 |
| Peptide-3A | H₂N-Arg-Asn-Ile-Ile-His-Gly-Ser-Asp-Ser-NH₂ | C | 21 | NME1 H118 |
| Peptide-3B | H₂N-Arg-Asn-Ile-Ile-1-pTza-GLy-Ser-Asp-Ser-NH₂ | C | 22 | NME1 H118 |
| Peptide-3C | H₂N-Arg-Asn-Ile-Ile-3-pTza-Gly-Ser-Asp-Ser-NH₂ | C | 23 | NME1 H118 |
| Peptide-4A | H₂N-Gly-Ala-Lys-Arg-His-Arg-Lys-Val-Leu-NH₂ | A | 24 | Histone H4 H18 |
| Peptide-4B | H₂N-Gly-Ala-Lys-Arg-pTza(1)-Arg-Lys-Val-Leu-NH₂ | B | 25 | Histone H4 H18 |
| Peptide-4C | H₂N-Gly-Ala-Lys-Arg-3-pTza-Arg-Lys-Val-Leu-NH₂ | D | 26 | Histone H4 H18 |
| Peptide-5A | H₂N-Val-Arg-Leu-Lys-His-Arg-Lys-Leu-Arg-NH₂ | A | 27 | KCa3.1 H358 |
| Peptide-5B | H₂N-Val-Arg-Leu-Lys-1-pTza-Arg-Lys-Leu-Arg-NH₂ | B | 28 | KCa3.1 H358 |
| Peptide-5C | H₂N-Val-Arg-Leu-Lys-3-pTza-Arg-Lys-Leu-Arg-NH₂ | D | 29 | KCa3.1 H358 |
| Peptide-6A | H₂N-Thr-Tyr-Ser-His-Asp-Asn-Ile-Ile-NH₂ | A | 30 | GNB1 H266 |
| Peptide-6B | H₂N-Thr-Tyr-Ser-1-pTza-Asp-Asn-Ile-Ile-NH₂ | C | 31 | GNB1 H266 |
| Peptide-6C | H₂N-Thr-Tyr-Ser-3-pTza-Asp-Asn-Ile-Ile-NH₂ | D | 32 | GNB1 H266 |

Peptide Dot Blot Screening of Rabbit Antisera:

Peptide dot blots were used initially to screen rabbit antisera titer. The 1-pTza and 3-pTza peptide libraries, His control library and a pTyr peptide (Nck pY105) were dissolved in water at a stock concentration of 1 mg/ml. 1:5 serial dilutions (500, 100, 20, 5, 1 and 0.2 ng/ul) were prepared for each peptide and 1 ul of each dilution was spotted on nitrocellulose membrane and allowed to dry for 1-2 hr at RT. Membranes were blocked for 1 hr at RT in Casein Blocking Buffer (0.1% casein, 0.2×PBS −/−) and incubated with rabbit antisera or pre-immune serum (diluted 1:1,000 in Blocking Buffer with 0.1% Tween-20) for 1 hr at RT or overnight at 4° C. All subsequent steps were as described for "immunoblotting with anti-pHis antibodies".

Protein Expression and Purification:

NME1, NME2 and PGAM were subcloned into the pGEX-6P-1 GST-fusion vector. The following primers were used for PCR amplification and insertion of BamH1 and EcoRI restriction sites;

NME1-Fw,
(SEQ ID NO: 33)
5'-GATCGGATCCATGGCCAACTGTGAGCGTAC-3',

NME1-Rev,
(SEQ ID NO: 34)
5'-GATCGAATTCTCATTCATAGATCCAGTTCTC-3',

NME2-Fw,
(SEQ ID NO: 35)
5'-GATCGGATC-CATGGCCAACCTGGAGCGCAC-3',

NME2-Rev,
(SEQ ID NO: 36)
5'-GATCGAATTCTTATTCATAGAC-CCAGTCATG -3'
and

PGAM-Fw,
(SEQ ID NO: 37)
5'-GATCGGATCCATGGCCGCCTACAAACTGGTG-3',

PGAM-Rev-
(SEQ ID NO: 38)
5'-GATCGAATTCTCACTTCTTGGCCTTGCCCTG-3'.

ROSETTA™ 2 (DE3) competent cells were transformed with pGEX-NME1, pGEX-NME2 or pGEX-PGAM and starter cultures from single colonies were grown at 37° C. for 16 hr in LB broth supplemented with 100 ug/ml ampicillin and 34 ug/ml chloramphenicol with shaking at 225 RPM. Expression cultures were diluted from starter cultures with the same medium to an A600 of 0.2. Protein expression was induced with 1 mM IPTG at an A600 of 0.6 for 3 hr at 30° C. Bacteria were pelleted (5,000×g for 10 min at 4° C.) and resuspended in 1 ml GST Lysis/Wash Buffer (PBS, pH 8.0, 1% Triton X-100, 5% glycerol, 1 mM DTT)/50 ml culture. Lysates were sonicated on ice and clarified by centrifugation (14,000×g for 30 min at 4° C.). Glutathione resin was equilibrated with GST lysis/wash buffer and 1 ml washed resin/200 ml culture was incubated with clarified bacterial lysates for 2 hr at 4° C. Resin was then pelleted and the supernatant was removed before washing at least 3 times with 10 ml wash buffer. Washed resin was resuspended in 2 ml PreScission Protease Buffer (20 mM Tris pH=7.0, 150 mM NaCl, 1 mM DTT, 0.5 mM EDTA) and cleavage of GST-tag was performed overnight at 4° C. using 2 ul PreScission Protease (5 U/200 ml culture). Cleaved resin was pelleted (1000×g for 5 min at 4° C.) and supernatants were transferred to fresh tubes. Buffer exchange into Storage Buffer B (50 mM Tris-HCl, pH 8.0, 100 mM NaCl, 1 mM DTT) was performed using centrifugal filters and proteins were concentrated to ~1 ug/ul. Purified proteins were supplemented with 10% glycerol and stored at −80° C. Quantification of purified proteins was performed by densitometry of Coomassie stained gels using a BSA standard curve.

NME and PGAM In Vitro Phosphorylation Assays:

In vitro autophosphorylation of purified NME1 and NME2 (10-30 ng/ul) was performed in TMD buffer (20 mM Tris-HCl, pH 8.0, 5 mM $MgCl_2$, 1 mM DTT) at RT. Fresh ATP was added to initiate reactions which were allowed to proceed at RT for 10 min. Reactions were stopped by addition of 5× pH 8.8 sample buffer and analyzed immediately by SDS-PAGE (see immunoblotting with anti-pHis antibodies). Reactions lacking ATP or treated briefly with heat or acid served as negative controls. In vitro autophosphorylation of PGAM was performed as described for NME1 except 2,3-diphosphoglycerate (2,3-DPG) was used as the phosphate donor instead of ATP and incubations were carried out at 30° C. Reactions lacking 2,3-DPG or treated briefly with heat served as negative controls. Heat treatment was performed after addition of 5× pH 8.8 sample buffer for 10-15 min at 95° C. Acid treatment was performed by adding 25 ul 1N HCl to a 100 ul reaction and incubating at 37° C. for 15 min. Reactions were neutralized with 25 ul 1N NaOH before addition of 5× pH 8.8 sample buffer.

Immunoblotting with Anti-pHis Antibodies:

In general, immunoblotting with anti-pHis antibodies was performed with modifications to standard procedures to help preserve pHis for detection. Buffers were adjusted to pH 8-9 to stabilize pHis and methods were modified to avoid heating samples. Protein samples were prepared in pH 8.8 sample buffer (5×=10% SDS, 250 mM Tris-HCl, pH 8.8, 0.02% Bromophenol blue, 50% glycerol, 50 mM EDTA, 500 mM DTT) for electrophoresis. Mammalian whole cell lysates were prepared by rinsing 70-100% confluent 10 $cm^2$ dishes twice with 5 ml cold TD buffer (TBS −/−, pH 8). Cells were scraped directly into 2× pH 8.8 sample buffer, incubated on ice and a cup horn sonicator was used (3-5×5 sec bursts) to disrupt cells and shear DNA. Lysates were clarified by centrifugation (14,000×g for 5-15 min at 4° C.) and analyzed immediately using freshly prepared Bis-Tris polyacrylamide minigels with a modified, pH 8.8 stacking gel and either 10% or 12.5% resolving gels. Electrophoresis buffer recipes were as follows: Running Buffer: (1×20 L, pH 8.5) 20 g SDS, 60 g Trizma Base, 288 g glycine, $dH_2O$ to 20 L, Transfer Buffer: (1×4 L, pH 8.5) 56.7 g glycine, 4 g SDS, 12 g Trizma Base, 800 ml MeOH, $dH_2O$ to 4 L. All electrophoresis steps were performed at 4° C. and samples were resolved at 90-100V for 2-3 hr. Proteins were transferred to Immunoblon-FL PVDF membranes at 30V for 12-18 hr at 4° C. and immediately incubated for 45-60 min at RT or >2 hr at 4° C. in Casein Blocking Buffer (0.1% casein, 0.2× PBS −/−). Primary antibodies were diluted in blocking buffer with 0.1% Tween-20, incubated with membranes for 1 hr at RT, or 3-18 hr at 4° C. Membranes were washed at least three times for 10 min each with 0.1% TBST before incubation with secondary antibodies for 45-50 min at room temperature. Rabbit anti-pHis antisera was stored at −20° C. was used at 1:1,000 for dot blots and western blots. Affinity purified, polyclonal anti-pHis antibodies were stored at 4° C. and used at 1:200. After incubation with secondary antibodies, membranes were washed least four times for 10 min each with 0.1% TBST. Immunoblots and Coomassie stained gels were imaged on a LI-COR Odyssey Infrared Imaging System. Duplexing of primary antibodies was performed using both channels of the Odyssey by co-incubating membranes with rabbit primary antibodies with mouse; anti-FLAG-M2, anti-GST or anti-NME1. For rabbit antibodies, Alexa Fluor® 680 Goat Anti-Rabbit IgG secondary antibodies were diluted 1:20,000 in blocking buffer supplemented with 0.1% tween-20 and 0.01% SDS. For mouse primary antibodies, Goat Anti-Mouse IgG secondary antibody (DyLight 800 conjugate) were diluted 1:20,000 in blocking buffer supplemented with 0.1% tween-20 and 0.01% SDS and incubated alone or co-incubated with Alexa Fluor® 680 Goat Anti-Rabbit secondary antibodies for duplexed primary antibodies.

Slot Blot Screening of Hybridoma Cell Supernatants:

A slot blotting apparatus was used to screen up to 40 anti-pHis hybridoma cell supernatants simultaneously. Preparative slab gels were cast using custom Teflon combs to create stacking gels that contained one large sample well and a single lane for loading protein molecular weight standards. SDS-PAGE was performed as described above for immunoblotting with anti-pHis antibodies. Briefly, PVDF membranes were clamped into the BioRad Miniprotean II Multiscreen Apparatus and blotting was performed as instructed by the manufacturer. IgG concentrations of hybridoma cell-supernatants (obtained from IgG ELISA assays performed by Epitomics) were normalized to 0.5 ug/ml for screening of anti-pHis mAbs (dilution factors ranged from 1:5 to 1:500) by dilution with casein blocking buffer supplemented with 0.1% Tween-20. 600 ul of each diluted mAb was pipetted into each chamber and incubated on top of the membrane for at 4° C. for 3 hr. After three 10 min washes of the membranes in the apparatus with 0.1% TBST, the membranes were transferred to blotting containers and washed again using larger volumes of 0.1% TBST. Incubation with secondary antibodies imaging was performed as described above.

Affinity Purification of Polyclonal pHis Antibodies:

Affinity columns for purification of polyclonal antibodies from rabbit antisera were prepared by covalently coupling 2 mg of either PEG-1-pTza or PEG-3-pTza peptide libraries to 2 ml SulfoLink agarose resin according to manufacturer's instructions. 5 ml of the corresponding anti-1-pTza or anti-3-pTza antisera was thawed on ice and diluted 1:2 with PBS (pH 7.4). Diluted antiserum was clarified by centrifugation (8,000×g for 20 min at 4° C.) and a sample was taken for analysis ("Input"). The columns were equilibrated with 15 ml PBS and the clarified antiserum was passed over columns three times. The flow through (FT) was collected and the column was then washed twice with PBS (15 ml="Wash 1", 1 ml="Wash 2"). The antibodies were eluted by addition of 0.1 M glycine (pH 2.5) buffer and 15×1 ml and 4×2 ml elution fractions were collected and immediately neutralized to pH 7 with sodium phosphate. A final wash step was performed with PBS (15 ml="Wash 3", 1 ml="Wash 4"). Samples from each elution and wash fraction and a 10 ul sample of column material ("col") were saved for SDS-PAGE analysis followed by Coomassie staining (FIG. 3D) to monitor binding and elution of IgG. Elution fractions were also tested for anti-3-pHis antibodies by immunoblotting in vitro phosphorylated PGAM (FIG. 3E).

pTza Peptide Dot Blot Arrays:

1-pTza, 3-pTza or His was incorporated into synthetic peptides of defined sequences from mammalian proteins with mapped pHis sites. The peptides used were as follows: ACLY-like H760 (AGAG-X-AGAG, SEQ ID NO: 62), PGAM H11 (VLIR-X-GESA, SEQ ID NO: 63), NME1 H118 (RNII-X-GSDS, SEQ ID NO: 64), Histone H4 H18 (GAKR-X-RKVL, SEQ ID NO: 65), KCa3.1 H358 (VRLK-X-RKLR, SEQ ID NO: 66) and GNB1 H266 (MTYS-X-DNII, SEQ ID NO: 67) where X=His, 1-pTza or 3-pTza. Peptides were dissolved in water at a stock concentration of 1 mg/ml. 1:5 serial dilutions (500, 100, 20, 5, 1 and 0.2 ng/ul) were prepared for each peptide and 1 ul of each dilution was spotted on nitrocellulose membrane and allowed to dry for 1-2 hr at RT. The pTza peptide stock solutions had a pH of 4-5 so these were neutralized by addition of 25 ul of 1M Tris buffer pH 8.0. Immunoblotting was performed as described above.

Cell Culture and Stable Cell Line Generation:

Human embryonic kidney cells (HEK 293), HeLa, Psrc11 and pancreatic stellate cells (PaSCs) were cultured in a 37° C., 5.0% $CO_2$ incubator. HEK 293 and HeLa cells were grown in DMEM (4.5 g/liter glucose, L-glutamine, and sodium pyruvate) supplemented with 10% FBS without antibiotics. Prsc11 were grown in DMEM supplemented with 4% FCS and Pen/Strep.

For generation of stably transfected FLAG-NME1 cell lines, HEK 293 cells were transiently transfected with 15 ug FLAG-NME1 mammalian expression vector in a 10 $cm^2$ dish using the calcium phosphate method. 48 hr post-transfection cells were split and plated in 96-well plates and stable transfectants were selected with G418. After 10 days in selection medium, surviving clones were trypsinized and expended in 6-well plates. Single colonies were selected, expanded and cell lysates were analyzed by immunoblotting with anti-NME1 and anti-FLAG antibodies to confirm stable integration.

Rabbit Hybridoma Cell Culture:

pHis hybridoma cell lines were maintained with Growth Medium (1×HAT 240E medium; 500 ml RPMI 1640, 40 ml Rabbit Hybridoma Supplement A (Epitomics), 55 µM 2-Mercaptoethanol and 10% FBS) in a 37° C., 5% $CO_2$ incubator. Briefly, cultures were seeded at $1\times10^5$ cells/ml and split at 70-80% confluency by aspirating media and replacing with fresh medium. Cell lines were stored in liquid N2 in freezing media (90% FBS, 10% DMSO).

Sequencing pHis Antibody IgG VH and VL Regions:

Anti-1-pHis and Anti-3-pHis hybridomas were cultured as described above and ~750,000 cells were collected by centrifugation at 1,100 RPM for 5 min. 20-30 ug RNA was isolated from each hybridoma using the Qiagen RNA Easy Mini Kit according to the manufacturer's instructions. RT-PCR was performed to using the Superscript III First-Strand Synthesis System (Life Technologies Cat. 18080-051) to synthesize cDNA from RNA primed with oligo(dT) primers. PCR primers used to amplify and sequence IgG $V_H$ and $V_L$ regions are listed (SEQ ID NOs: 39-61).

TABLE

Rabbit $V_H$ $V_L$ primers

| Light Chain | |
|---|---|
| Vk1_AA | 5' GTGATGACCCAGACTCCA 3' |
| Vk1_C | 5' GTGCTGACCCAGACTCCA 3' |
| Vk2_A | 5' GATATGACCCAGACTCCA 3' |
| Vk2_C | 5' GATCTGACCCAGACTCCA 3' |
| vk3 | 5' TTTGATTTCCACATTGGTGCC 3' |
| vk4 | 5' TAGGATCTCCAGCTCGGTCCC 3' |
| vk5_C | 5' TTTGACCACCACCTCGGTCCC 3' |
| vk5_G | 5' TTTGACGACCACCTCGGTCCC 3' |
| Vλ1 | 5' GTGCTGACTCAGTCGCCCTC 3' |
| vλ2 | 5' GCCTGTGACGGTCAGCTGGGTCCC 3' |
| Heavy Chain | |
| VH1_A | 5' AGTCGGTGGAGGAGTCCAGG 3' |
| VH1_G | 5' AGTCGGTGGAGGAGTCCGGG 3' |
| VH2 | 5' AGTCGGTGAAGGAGTCCGAG 3' |
| VH3_C | 5' AGTCGCTGGAGGAGTCCGGG 3' |
| VH3_T | 5' AGTCGTTGGAGGAGTCCGGG 3' |
| VH4_CA | 5' AGCAGCAGCTGATGGAGTCCGG 3' |
| VH4_GA | 5' AGGAGCAGCTGATGGAGTCCGG 3' |
| VH4_CG | 5' AGCAGCAGCTGGTGGAGTCCGG 3' |
| VH4_GG | 5' AGGAGCAGCTGGTGGAGTCCGG 3' |
| vh5_AC | 5' AGAGACGGTGACCAGGGTGCC 3' |
| vh5_GC | 5' GGAGACGGTGACCAGGGTGCC 3' |
| vh5_AT | 5' AGAGATGGTGACCAGGGTGCC 3' |
| vh5_GT | 5' GGAGATGGTGACCAGGGTGCC 3' | cDNA from RT-PCR reactions was analyzed by gel electrophoresis and reactions yielding products of the correct size (300-350 bp) were sequenced with both forward and reverse primers.

pHis mAb Production and Purification:

pHis hybridomas were expanded from 10 cm2 dishes to T175 flasks in 60 ml Growth Medium. Once confluent, cells were collected by centrifugation at 1,100 RPM for 5 min in 2×50 mL tubes. 22.5 ml supernatant was removed from each tube and cells were resuspended in the remaining 2×7.5 ml medium. Cells were transferred back into the same T175 flask and 45 ml fresh Serum-Free Medium (SFM; IS-MAB CD chemically defined medium (Irvine Scientific), 1% antibiotic/antimycotic supplement and 1% Glutamax) was added. Cells were acclimated to this low-serum (2.5%) condition for 3 days. Cells were spun, as before, into 2×50 ml tubes and all media was aspirated from pellets. Cells were resuspended in 2×7.5 ml SFM and transferred back into their respective T175 flasks with 45 ml (60 ml total) SFM. Cells were grown in SFM until cell viability was approximately 50% (~7-10 days). To harvest antibodies, cells were collected by centrifugation. Cell supernatants were spun again in fresh tubes at 3,000 RPM for an additional 15 min. For antibody purification, 1 ml Protein-A-agarose beads were incubated overnight at 4° C. with 50 ml SFM hybridoma cell supernatant. The Protein-A-agarose beads were pelleted at 4,000×g for 5 min at 4° C. and washed with 3× with 10 ml PBS (pH 7.4). Anti-pHis IgG was eluted with two sequential additions of 1 ml Elution Buffer (200 mM Glycine, pH 2.8), which were immediately neutralized with 1.0 M Tris-HCl (pH 8.3). Anti-pHis mAb concentrations were measured by IgG A280 and stored at 4° C. Purified mAbs were used at a concentration of 0.5 ug/ml (~1:2000) and validated by immunoblotting cell lysates and dot blotting in vitro phosphorylated NME1 (1-pHis) or PGAM (3-pHis).

Mass Spectrometry:

In vitro phosphorylated NME1 and PGAM samples were first denatured in 8 M urea and then reduced and alkylated with 10 mM TCEP and 55 mM iodoacetamide respectively.

The samples were diluted to 2 M urea with 100 mM Tris pH 8.5 and then digested with trypsin [Promega] at room temperature for 4 hours.

Each protein digest was pressure-loaded onto 250 micron i.d. fused silica capillary [Polymicro Technologies] columns with a Kasil frit packed with 3 cm of 5 micron C18 resin [Phenomenex]. After desalting, each column was connected to a 100 micron i.d. fused silica capillary [Polymicro Technologies] analytical column with a 5 micron pulled-tip, packed with 10 cm of 5 micron C18 resin [Phenomenex].

Each column was placed inline with an Easy NanoLC II pump [Thermo Scientific] and the eluted peptides were electrosprayed directly into a Q Exactive mass spectrometer [Thermo Scientific]. The buffer solutions used were 10 mM ammonium bicarbonate pH 5 (buffer A) and 100% methanol (buffer B). The 90 minute elution gradient had the following profile: 10% buffer B at 5 minutes, to 55% buffer B at 50 minutes, to 99% buffer B at 65 minutes and continuing to 75 minutes. A cycle consisted of one full scan mass spectrum (400-1600 m/z) at 70 K resolution followed by up to 10 data-dependent MS/MS (fixed first mass, 100 m/z) at 17.5 K resolution using a normalized collision energy (NCE) of 25 with 20% stepped NCE. Charge state exclusion was selected such that only +2 and +3 ions were selected for fragmentation. Dynamic exclusion was set at 10 seconds. Application of mass spectrometer scan functions and HPLC solvent gradients were controlled by the Xcalibur data system [Thermo Scientific].

MS/MS spectra were extracted using RawXtract (version 1.9.9) (McDonald et al., *Rapid Commun Mass Spectrom.* 18:2162-21682004 (2004)). MS/MS spectra were searched with the ProLuCID algorithm (Eng et al., *J Am Soc Mass Spectrom.* 5: 976-989, (1994)) against a *Saccharomyces cerevisiae* and *Escherichia coli* database concatenated to a decoy database in which the sequence for each entry in the original database was reversed (Peng et al., *J Proteome Res.* 2: 43-50 (2003)) supplemented with UniProt sequences for either human NM23 or human PGAM1. The ProLuCID search was performed using full enzyme specificity, static modification of cysteine due to carboxyamidomethylation (57.02146) and differential modification of histidine, serine, threonine and tyrosine due to phosphorylation (79.9663). The data was searched using a precursor mass tolerance of 50 ppm and a fragment ion mass tolerance of 10 ppm. ProLuCID search results were assembled and filtered using the DTASelect (version 2.0) algorithm (Tabb et al., *J Proteomics Res.* 1:21-26, (2002)). All peptide-spectra matches had less than 10 ppm mass error. Phosphorylation site assignment was confirmed by manual annotation of spectra.

Immunofluorescence:

Primary murine macrophages were differentiated from bone marrow progenitors (Zhang et al., 2008) plated on cover slips and incubated O/N in fresh medium. Cells were incubated with 10 μg/ml Oregon Green-Dextran®488 and/or LysoTracker (50 nM) for 1-2 hr prior to fixation with 4% PFA for 10 min. Negative controls were performed by boiling slides for 5-10 min in 0.01 M citrate buffer or by pre-incubation of pHis mAbs with pTza blocking peptides [5 g/ml]. Cells were permeabilized in blocking buffer (PBS, 5% serum ($2^{nd}$ Ab species), 2% BSA, 0.1% Tween) with 0.1% Triton-X100 for 1 hr at 4° C. Primary antibodies were diluted to 1 μg/ml in blocking buffer and incubated with slides for 2 hr at 4° C. Slides were washed 5× with cold PBS+0.1% Tween and incubated with $2^{nd}$ Ab diluted 1:400 in blocking buffer for 1 hr at 4° C. Slides were mounted on cover slips after washing 5× with cold PBS+0.1% Tween. See also Extended Experimental Procedures for immunostaining of HeLa cells.

1-pHis and 3-pHis Immunofluorescence Staining of HeLa Cells:

HeLa cells were plated on cover slips in 6-well plates and grown until 30-50% confluent. Cells were washed with sterile filtered PBS (pH 7.4) and fixed for 20 min at RT in 4% PFA (16% PFA diluted 1:4 in PBS). After fixation, cells were washed 2× with PBS and then permeabilized with PBS (pH 9.0)+0.1% Triton X-100 at RT for 15 min. Cells were then washed 3× with PBS (pH 9.0) before blocking in sterile filtered, 0.1% TBST with 4% BSA at RT for 30 min. Cover slips were transferred to parafilm, incubated with primary antibodies (1-pHis mAb SC1-1, diluted 1:100) at RT for 90 min and washed 3× with 0.1% TBST for 5 min. Secondary antibodies (anti-rabbit 488 nm and anti-mouse 568 nm) were diluted 1:2,000 in TBST plus 1% BSA and incubated with coverslips at RT for 60 min in the dark. Cells were then washed 3 times with TBST at RT for 5 min. To stain nuclei, coverslips were incubated with PBS plus DAPI at 1:4,000 for 2 min and washed 3 times with PBS. Alternative methods for fixation were used for co-staining experiments. Methanol fixation (Aurora A and -tubulin) was performed by incubating cells at −20° C. for 15 min in methanol. Pre-permeabilization (γ-tubulin and α-tubulin) was performed by incubation of cells 45 sec in 0.5% Triton X-100 followed by 4% PFA for 15 min at pH 9.0. Coverslips were mounted and stored in the dark prior to scanning on a confocal microscope under 60× magnification.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. An isolated monoclonal antibody or antigen binding fragment thereof, comprising a heavy chain variable region and a light chain variable region, wherein the heavy chain variable region comprises a heavy chain complementarity determining region (H-CDR)I, a H-CDR2, and a H-CDR3, and wherein the light chain variable region comprises a light chain complementarity determining region (L-CDR) 1, a L-CDR2, and a L-CDR3, wherein the isolated monoclonal antibody or antigen binding fragment comprises:
   a) the H-CDR1, H-CDR2, and H-CDR3 of the amino acid sequence set forth as SEQ ID NO: 1, and the L-CDR1, L-CDR2, and L-CDR3 of the amino acid sequence set forth as SEQ ID NO: 5;
   b) the H-CDR1, H-CDR2, and H-CDR3 of the amino acid sequence set forth as SEQ ID NO: 2 and the L-CDR1, L-CDR2, and L-CDR3 of the amino acid sequence set forth as SEQ ID NO: 6;
   c) the H-CDR1, H-CDR2, and H-CDR3 of the amino acid sequence set forth as SEQ ID NO: 3 and the L-CDR1, L-CDR2, and L-CDR2 of the amino acid sequence set forth as SEQ ID NO: 7; or
   d) the H-CDR1, H-CDR2, and H-CDR3 of the amino acid sequence set forth as SEQ ID NO: 4, and the L-CDR1, L-CDR2, and L-CDR3 of the amino acid sequence set forth as SEQ ID NO: 8
wherein the monoclonal antibody specifically binds a polypeptide comprising a histidine phosphorylated at N3 (3-pHis).

2. The isolated monoclonal antibody or antigen binding fragment of claim 1, wherein:
   a) the H-CDR1, H-CDR2, and H-CDR3 comprise amino acids 21-28, 45-52, and 88-97 of the amino acid sequence set forth as SEQ ID NO: 1, respectively, and the L-CDR1, L-CDR2, and L-CDR3 comprise amino acids 28-33, 51-53, and 90-102 of the amino acid sequence set forth as SEQ ID NO: 5 respectively;
   b) the H-CDR1, H-CDR2, and H-CDR3 comprise amino acids 21-28, 46-52, and 91-101 of the amino acid sequence set forth as SEQ ID NO: 2, respectively, and the L-CDR1, L-CDR2, and L-CDR3 comprise amino acids 27-34, 52-54, 91-103 of the amino acid sequence set forth as SEQ ID NO: 6, respectively;
   c) the H-CDR1, H-CDR2, and H-CDR3 including amino acids 24-31, 49-55, 94-104 of the amino acid sequence set forth as SEQ ID NO: 3, respectively, and the L-CDR1, L-CDR2, and L-CDR3 comprise amino acids 27-34, 52-54, and 91-109 of the amino acid sequence set forth as SEQ ID NO: 7, respectively; or
   d) the H-CDR1, H-CDR2, and H-CDR3 comprise amino acids 24-31, 49-55, 94-104 of the amino acid sequence set forth as SEQ ID NO: 4, respectively, and the L-CDR1, L-CDR2, and L-CDR3 comprise amino acids amino acids 27-33, 51-53 and 90-102 of the amino acid sequence set forth as SEQ ID NO: 8, respectively.

3. The isolated monoclonal antibody or antigen binding fragment of claim 1, wherein the heavy chain variable region comprises:
   a) amino acids 1-108 of the amino acid sequence set forth as SEQ ID NO: 1;
   b) amino acids 1-112 of the amino acid sequence set forth as SEQ ID NO: 2;
   c) amino acid 1-115 of the amino acid sequence set forth as SEQ ID NO: 3, or
   d) amino acids 1-115 of the amino acid sequence set forth as SEQ ID NO: 4, respectively.

4. The isolated monoclonal antibody or antigen binding fragment of claim 1, wherein the light chain variable region comprises:
   a) amino acids 1-113 of the amino acid sequence set forth as SEQ ID NO: 5;
   b) amino acids 1-114 of the amino acid sequence set forth as SEQ ID NO: 6;
   c) amino acid 1-120 of the amino acid sequence set forth as SEQ ID NO: 7; or
   d) amino acids 1-113 of the amino acid sequence set forth as SEQ ID NO: 8, respectively.

5. The isolated monoclonal antibody or antigen binding fragment of claim 1, wherein:
   a) the heavy chain variable region comprises amino acids 1-108 of the amino acid sequence set forth as SEQ ID NO: 1 and the light chain variable region comprises amino acids 1-113 of the amino acid sequence set forth as SEQ ID NO: 5;
   b) the heavy chain variable region comprises amino acids 1-112 of the amino acid sequence set forth as SEQ ID NO: 2 and the light chain variable region comprises amino acids 1-114 of the amino acid sequence set forth as SEQ ID NO: 6;
   c) the heavy chain variable region comprises amino acid 1-115 of the amino acid sequence set forth as SEQ ID NO: 3 and the light chain variable region comprises amino acids 1-120 of the amino acid sequence set forth as SEQ ID NO: 7, or
   d) the heavy chain variable region comprises amino acids 1-115 of the amino acid sequence set forth as SEQ ID NO: 4 and the light chain variable region comprises amino acids 1-113 of the amino acid sequence set forth as SEQ ID NO: 8.

6. The isolated monoclonal antibody or antigen biding fragment of claim 1, wherein the monoclonal antibody, or antigen binding fragment, comprises a human framework region.

7. The isolated monoclonal antibody of claim 1, wherein the antibody is an IgG.

8. The antigen binding fragment of claim 1.

9. The antigen binding fragment of claim 8, wherein the antigen binding fragment is a Fv, Fab, F(ab')$_2$, scFV or a scFV$_2$ fragment.

10. The isolated monoclonal antibody or antigen binding fragment of claim 1, conjugated to an effector molecule or a detectable label.

11. The isolated monoclonal antibody or antigen binding fragment of claim 10, wherein the detectable marker is a fluorescent, enzymatic, heavy metal or radioactive marker.

12. An isolated nucleic acid molecule encoding the monoclonal antibody or antigen binding fragment of claim 1.

13. The isolated nucleic acid molecule of claim 12 operably linked to a promoter.

14. A vector comprising the nucleic acid molecule of claim 13.

15. The vector of claim 14, wherein the vector is a plasmid vector or a viral vector.

16. An isolated host cell, comprising the vector of claim 14.

17. A composition, comprising an effective amount of the isolated monoclonal antibody or antigen binding fragment of claim 1, a nucleic acid molecule encoding the monoclonal antibody or the antigen binding fragment, a vector comprising the nucleic acid molecule, or a host cell expressing the vector, and a pharmaceutically acceptable carrier.

18. A method for detecting the presence of a polypeptide comprising a histidine phosphorylated at N3, comprising:
   contacting a sample comprising polypeptides with an effective amount of the monoclonal antibody or antigen binding fragment of claim 1 under conditions sufficient to form an immune complex; and
   detecting the presence of the immune complex,
wherein the presence of the immune complex indicates the presence of the polypeptide comprising the histidine phosphorylated at N3.

19. The method of claim 18, wherein the monoclonal antibody or antigen binding fragment is conjugated to a detectable label.

20. The method of claim 18, wherein the polypeptide is present in or obtained from a biological sample from a subject.

21. The method of claim 18, wherein the polypeptide comprising the histidine phosphorylated at N3 is a component of a signal transduction pathway.

22. The method of claim 18, comprising quantitating the amount of the immune complex.

* * * * *

SEQUENCE LISTING

<160> NUMBER OF SEQ ID NOS: 70

<210> SEQ ID NO 1
<211> LENGTH: 203
<212> TYPE: PRT
<213> ORGANISM: Artificial Sequence
<220> FEATURE:
<223> OTHER INFORMATION: Synthetic polypeptide

<400> SEQUENCE: 1

Glu Ser Gly Gly Arg Leu Val Thr Pro Gly Gly Ser Leu Thr Leu Thr
1               5                   10                  15

Cys Thr Val Ser Gly Phe Ser Leu Ser Arg Tyr Asn Met Gly Trp Val
            20                  25                  30

Arg Gln Ala Pro Gly Lys Gly Leu Glu Trp Ile Gly Trp Ile Pro Phe
        35                  40                  45

Arg Gly Ser Leu Lys Tyr Ala Thr Trp Ala Thr Gly Arg Phe Thr Ile
    50                  55                  60

Ser Arg Thr Ser Thr Thr Val Asp Leu Arg Met Thr Gly Leu Thr Ala
65                  70                  75                  80

Ala Asp Thr Ala Thr Tyr Phe Cys Val Arg Ser Ser Asp Gly Phe Asp
                85                  90                  95

Leu Trp Gly Pro Gly Thr Leu Val Thr Val Ser Ser Gly Gln Pro Lys
            100                 105                 110

Ala Pro Ser Val Phe Pro Leu Ala Pro Cys Cys Gly Asp Thr Pro Ser
        115                 120                 125

Ser Thr Val Thr Leu Gly Cys Leu Val Lys Gly Tyr Leu Pro Glu Pro
    130                 135                 140

Val Thr Val Thr Trp Asn Ser Gly Thr Leu Thr Asn Gly Val Arg Thr
145                 150                 155                 160

Phe Pro Ser Val Arg Gln Ser Ser Gly Leu Tyr Ser Leu Ser Ser Val
                165                 170                 175

Val Ser Val Thr Ser Ser Ser Gln Pro Val Thr Cys Asn Val Ala His
            180                 185                 190

Pro Ala Thr Asn Thr Lys Val Asp Lys Thr Val
        195                 200

<210> SEQ ID NO 2
<211> LENGTH: 207
<212> TYPE: PRT
<213> ORGANISM: Artificial Sequence
<220> FEATURE:
<223> OTHER INFORMATION: Synthetic polypeptide

<400> SEQUENCE: 2

Glu Ser Gly Arg Gly Leu Val Gln Pro Gly Gly Ser Leu Thr Leu Thr
1               5                   10                  15

Cys Thr Ala Ser Gly Phe Ser Ile Asp Ser Tyr Gly Phe Ser Trp Val
            20                  25                  30

Arg Gln Ala Pro Gly Lys Gly Leu Glu His Ile Gly Tyr Leu Thr Ala
        35                  40                  45

Gly Gly Arg Ala Phe Tyr Ala Ser Trp Ala Lys Ser Arg Ser Thr Ile
    50                  55                  60

Thr Arg Asn Thr Asn Glu Asn Thr Val Thr Leu Lys Met Thr Ser Leu
65                  70                  75                  80

Thr Ala Ala Asp Thr Ala Thr Tyr Phe Cys Ala Lys Leu Gly Ser Gly
                85                  90                  95

Asn Pro Val Ala Ile Trp Gly Pro Gly Thr Leu Val Thr Val Ser Ser
            100                 105                 110

Gly Gln Pro Lys Ala Pro Ser Val Phe Pro Leu Ala Pro Cys Cys Gly
        115                 120                 125

Asp Thr Pro Ser Ser Thr Val Thr Leu Gly Cys Leu Val Lys Gly Tyr
    130                 135                 140

Leu Pro Glu Pro Val Thr Val Thr Trp Asn Ser Gly Thr Leu Thr Asn
145                 150                 155                 160

Gly Val Arg Thr Phe Pro Ala Val Arg Glu Ser Ser Gly Leu Tyr Ser
                165                 170                 175

```
Leu Asn Ser Val Gly Lys Val Thr Ser Ser Gln Pro Val Thr Cys
                180                 185                 190

Asn Val Ala His Pro Ala Thr Asn Thr Lys Val Asp Lys Thr Val
            195                 200                 205

<210> SEQ ID NO 3
<211> LENGTH: 210
<212> TYPE: PRT
<213> ORGANISM: Artificial Sequence
<220> FEATURE:
<223> OTHER INFORMATION: Synthetic polypeptide

<400> SEQUENCE: 3

Ser Val Lys Glu Ser Glu Gly Gly Leu Ile Lys Pro Gly Gly Ile Leu
1               5                   10                  15

Thr Leu Thr Cys Thr Ala Ser Gly Phe Ser Leu Ser Ser Tyr Gly Phe
                20                  25                  30

Ser Trp Val Arg Gln Ala Pro Gly Lys Gly Leu Glu His Ile Gly Tyr
            35                  40                  45

Leu His Ala Asn Gly Arg Ala Tyr Tyr Ala Thr Trp Ala Lys Ser Arg
    50                  55                  60

Ser Thr Ile Thr Arg Asn Thr Asn Leu Asn Thr Val Thr Leu Gln Leu
65                  70                  75                  80

Thr Ser Leu Thr Ala Ala Asp Thr Ala Thr Tyr Phe Cys Ala Lys Ile
                85                  90                  95

Gly Ser Val Ser Asp Val Ala Ile Trp Gly Pro Gly Thr Leu Val Thr
            100                 105                 110

Val Ser Ser Gly Gln Pro Lys Ala Pro Ser Val Phe Pro Leu Ala Pro
        115                 120                 125

Cys Cys Gly Asp Thr Pro Ser Ser Thr Val Thr Leu Gly Cys Leu Val
    130                 135                 140

Lys Gly Tyr Leu Pro Glu Pro Val Thr Val Thr Trp Asn Ser Gly Thr
145                 150                 155                 160

Leu Thr Asn Gly Val Arg Thr Phe Pro Ser Val Arg Gln Ser Ser Gly
                165                 170                 175

Leu Tyr Ser Leu Ser Ser Val Val Ser Val Thr Ser Ser Ser Gln Pro
            180                 185                 190

Val Thr Cys Asn Val Ala His Pro Ala Thr Asn Thr Lys Val Asp Lys
        195                 200                 205

Thr Val
    210

<210> SEQ ID NO 4
<211> LENGTH: 210
<212> TYPE: PRT
<213> ORGANISM: Artificial Sequence
<220> FEATURE:
<223> OTHER INFORMATION: Synthetic polypeptide

<400> SEQUENCE: 4

Ser Val Lys Glu Ser Glu Gly Gly Leu Phe Lys Pro Thr Asp Thr Leu
1               5                   10                  15

Thr Leu Thr Cys Thr Val Ser Gly Phe Ser Leu Thr Thr Tyr Gly Phe
                20                  25                  30

Ser Trp Val Arg Gln Ala Pro Gly Lys Gly Leu Glu Trp Ile Gly Tyr
            35                  40                  45

Val Arg Ser Asp Gly Arg Ile Tyr Tyr Thr Ser Trp Ala Lys Ser Arg
```

```
                50                  55                  60
Ser Thr Leu Thr Arg Asn Thr Asn Leu Asn Thr Val Thr Leu Ile Met
 65                  70                  75                  80

Thr Ser Leu Thr Val Ala Asp Thr Ala Thr Tyr Phe Cys Ala Lys Ile
                 85                  90                  95

Gly Ser Gly Thr Gly Val Ala Ile Trp Gly Pro Gly Thr Leu Val Thr
                100                 105                 110

Val Ser Ser Gly Gln Pro Lys Ala Pro Ser Val Phe Pro Leu Ala Pro
                115                 120                 125

Cys Cys Gly Asp Thr Pro Ser Ser Thr Val Thr Leu Gly Cys Leu Val
                130                 135                 140

Lys Gly Tyr Leu Pro Glu Pro Val Thr Val Thr Trp Asn Ser Gly Thr
145                 150                 155                 160

Leu Thr Asn Gly Val Arg Thr Phe Pro Ser Val Arg Gln Ser Ser Gly
                165                 170                 175

Leu Tyr Ser Leu Ser Ser Val Val Ser Val Thr Ser Ser Gln Pro
                180                 185                 190

Val Thr Cys Asn Val Ala His Pro Ala Thr Asn Thr Lys Val Asp Lys
                195                 200                 205

Thr Val
    210

<210> SEQ ID NO 5
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 5

Ala Gln Phe Val Met Thr Gln Thr Pro Ala Ser Val Glu Ala Val Val
  1               5                  10                  15

Gly Gly Thr Val Thr Ile Lys Cys Gln Ala Ser Arg Asp Thr Gly Asp
                 20                  25                  30

Gly Leu Ile Trp Tyr Gln Gln Lys Pro Gly Gln Pro Pro Lys Arg Leu
             35                  40                  45

Ile Tyr Lys Ala Ser Thr Val Ala Ser Gly Val Pro Ser Arg Phe Lys
 50                  55                  60

Gly Arg Gly Ser Gly Thr Asp Phe Thr Leu Thr Ile Ser Asp Leu Glu
 65                  70                  75                  80

Cys Ala Asp Ala Ala Thr Tyr Tyr Cys His Ser Asn Phe Tyr Asn Arg
                 85                  90                  95

Trp Thr Tyr Gly Asn Ala Phe Gly Gly Gly Thr Glu Val Val Val Lys
                100                 105                 110

Gly Asp Pro Val Ala Pro Thr Val Leu Ile Phe Pro Pro Ala Ala Asp
                115                 120                 125

Gln Val Ala Thr Gly Thr Val Thr Ile Val Cys Val Ala Asn Lys Tyr
                130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
                180                 185                 190

His Lys Glu Tyr Thr Cys Lys Val Thr Gln Gly Thr Thr Ser Val Val
```

Gln Ser Phe Asn Arg Gly Asp Cys
    210                 215

<210> SEQ ID NO 6
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 6

Asp Pro Val Met Thr Pro Thr Pro Ser Phe Thr Ser Ala Ala Val Gly
1               5                   10                  15

Gly Thr Val Thr Ile Asn Cys Gln Ser Ser Gln Ser Val Trp Arg Asn
            20                  25                  30

Lys Asn Leu Ala Trp Tyr Gln Gln Lys Pro Gly Gln Pro Pro Lys Arg
        35                  40                  45

Leu Ile Tyr Ala Ile Ala Thr Leu Asp Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Val Gly His Tyr Gly Ser
                85                  90                  95

Glu Asn Asp Ala Tyr Tyr Ala Phe Gly Gly Thr Glu Val Val Val
            100                 105                 110

Lys Gly Asp Pro Val Ala Pro Thr Val Leu Ile Phe Pro Pro Ser Ala
        115                 120                 125

Asp Leu Val Ala Thr Gly Thr Val Thr Ile Val Cys Val Ala Asn Lys
    130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Thr Pro Gln Asn Ser Ala Asp Cys
                165                 170                 175

Thr Tyr Asn Leu Ser Ser Thr Leu Thr Leu Thr Ser Thr Gln Tyr Asn
            180                 185                 190

Ser His Lys Glu Tyr Thr Cys Lys Val Thr Gln Gly Thr Thr Ser Val
        195                 200                 205

Val Gln Ser Phe Asn Arg Gly Asp Cys
    210                 215

<210> SEQ ID NO 7
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 7

Asp Pro Val Met Thr Gln Thr Pro Ser Ser Thr Ser Ala Ala Val Gly
1               5                   10                  15

Gly Thr Val Thr Ile Asn Cys Gln Ser Ser Glu Ser Ile Tyr Asn Asn
            20                  25                  30

Lys Asn Leu Ala Trp Tyr Gln Gln Lys Pro Gly Gln Ser Pro Arg Arg
        35                  40                  45

Leu Ile Tyr Ser Ile Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Val Gly Tyr Tyr Tyr Ser
                85                  90                  95

Gly Gly Tyr Tyr Tyr Ser Gly Ser Ala Ala Tyr Tyr Ala Phe Gly Gly
            100                 105                 110

Gly Thr Glu Val Val Val Lys Gly Asp Pro Val Ala Pro Thr Val Leu
        115                 120                 125

Ile Phe Pro Pro Ser Ala Asp Leu Val Ala Thr Gly Thr Val Thr Ile
    130                 135                 140

Val Cys Val Ala Asn Lys Tyr Phe Pro Asp Val Thr Val Thr Trp Glu
145                 150                 155                 160

Val Asp Gly Thr Thr Gln Thr Thr Gly Ile Glu Asn Ser Lys Thr Pro
                165                 170                 175

Gln Asn Ser Ala Asp Cys Thr Tyr Asn Leu Ser Ser Thr Leu Thr Leu
            180                 185                 190

Thr Ser Thr Gln Tyr Asn Ser His Lys Glu Tyr Thr Cys Lys Val Thr
        195                 200                 205

Gln Gly Thr Thr Ser Val Val Gln Ser Phe Asn Arg Gly Asp Cys
    210                 215                 220

<210> SEQ ID NO 8
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 8

Asp Gly Val Met Thr Pro Thr Pro Ala Ser Ala Ser Ala Gly Val Gly
1               5                   10                  15

Gly Thr Val Thr Ile Asn Cys Gln Ser Ser Gln Ser Ile Tyr Lys Lys
            20                  25                  30

Tyr Ile Ala Trp Tyr Gln Gln Lys Pro Gly Gln Pro Pro Lys Arg Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Val Ala Thr Tyr Tyr Cys Val Gly Tyr Tyr Ile Ile Thr
                85                  90                  95

Asn Asp Ala Tyr Tyr Ser Phe Gly Gly Thr Glu Val Val Val Lys
            100                 105                 110

Gly Asp Pro Val Ala Pro Thr Val Leu Ile Phe Pro Pro Ser Ala Asp
        115                 120                 125

Leu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(5)
<223> OTHER INFORMATION: Xaa = Gly or Ala
<220> FEATURE:
<221> NAME/KEY: MISC_FEATURE
<222> LOCATION: (6)..(6)
<223> OTHER INFORMATION: Xaa = His, 1-pTza or 3-pTza
<220> FEATURE:
<221> NAME/KEY: MISC_FEATURE
<222> LOCATION: (7)..(10)
<223> OTHER INFORMATION: Xaa = Gly or Ala
<220> FEATURE:
<221> NAME/KEY: MOD_RES
<222> LOCATION: (10)..(10)
<223> OTHER INFORMATION: AMIDATION

<400> SEQUENCE: 9

Cys Xaa Xaa Xaa Xaa Xaa Xaa Xaa Xaa Xaa
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: PHOSPHORYLATION

<400> SEQUENCE: 10

Cys Gly Glu Arg Leu Tyr Asp Leu Asn Met Pro Ala Tyr Val Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Cys Gly Glu Arg Leu Tyr Asp Leu Asn Met Pro Ala Tyr Val Lys
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: PHOSPHORYLATION

<400> SEQUENCE: 12

Cys Leu Lys Pro Leu Lys Thr Tyr Val Asp
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Cys Leu Lys Pro Leu Lys Thr Tyr Val Asp
1               5                   10

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: PHOSPHORYLATION

<400> SEQUENCE: 14

Ala Val Ser Val Ser Glu Thr Asp Asp Tyr Ala Glu Ile Ile Asp Glu
1               5                   10                  15

Glu Asp Thr Tyr Thr
            20

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ala Gly Ala Gly His Ala Gly Ala Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 1-pTza

<400> SEQUENCE: 16

Ala Gly Ala Gly Xaa Ala Gly Ala Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 3-pTza

```
<400> SEQUENCE: 17

Ala Gly Ala Gly Xaa Ala Gly Ala Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Val Leu Ile Arg His Gly Glu Ser Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 1-pTza

<400> SEQUENCE: 19

Val Leu Ile Arg Xaa Gly Glu Ser Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 3-pTza

<400> SEQUENCE: 20

Val Leu Ile Arg Xaa Gly Glu Ser Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Arg Asn Ile Ile His Gly Ser Asp Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 1-pTza

<400> SEQUENCE: 22
```

Arg Asn Ile Ile Xaa Gly Ser Asp Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 3-pTza

<400> SEQUENCE: 23

Arg Asn Ile Ile Xaa Gly Ser Asp Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Gly Ala Lys Arg His Arg Lys Val Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 1-pTza

<400> SEQUENCE: 25

Gly Ala Lys Arg Xaa Arg Lys Val Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 3-pTza

<400> SEQUENCE: 26

Gly Ala Lys Arg Xaa Arg Lys Val Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Val Arg Leu Lys His Arg Lys Leu Arg
1               5

```
<210> SEQ ID NO 28
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 1-pTza

<400> SEQUENCE: 28

Val Arg Leu Lys Xaa Arg Lys Leu Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = 3-pTza

<400> SEQUENCE: 29

Val Arg Leu Lys Xaa Arg Lys Leu Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Thr Tyr Ser His Asp Asn Ile Ile
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = 1-pTza

<400> SEQUENCE: 31

Thr Tyr Ser Xaa Asp Asn Ile Ile
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = 3-pTza

<400> SEQUENCE: 32
```

Thr Tyr Ser Xaa Asp Asn Ile Ile
1               5

<210> SEQ ID NO 33
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 33
gatcggatcc atggccaact gtgagcgtac               30

<210> SEQ ID NO 34
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 34
gatcgaattc tcattcatag atccagttct c              31

<210> SEQ ID NO 35
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 35
gatcggatcc atggccaacc tggagcgcac               30

<210> SEQ ID NO 36
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 36
gatcgaattc ttattcatag acccagtcat g              31

<210> SEQ ID NO 37
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 37
gatcggatcc atggccgcct acaaactggt g              31

<210> SEQ ID NO 38
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 38
gatcgaattc tcacttcttg gccttgccct g              31

<210> SEQ ID NO 39
<211> LENGTH: 18
<212> TYPE: DNA

```
<213> ORGANISM: Artificial Sequence
<220> FEATURE:
<223> OTHER INFORMATION: Synthetic polynucleotide

<400> SEQUENCE: 39
gtgatgaccc agactcca                                                    18

<210> SEQ ID NO 40
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 40
gtgctgaccc agactcca                                                    18

<210> SEQ ID NO 41
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 41
gatatgaccc agactcca                                                    18

<210> SEQ ID NO 42
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 42
gatctgaccc agactcca                                                    18

<210> SEQ ID NO 43
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 43
tttgatttcc acattggtgc c                                                21

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44
taggatctcc agctcggtcc c                                                21

<210> SEQ ID NO 45
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 45
tttgaccacc acctcggtcc c                                                21
```

<210> SEQ ID NO 46
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 46
tttgacgacc acctcggtcc c                                    21

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
gtgctgactc agtcgccctc                                       20

<210> SEQ ID NO 48
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 48
gcctgtgacg gtcagctggg tccc                                  24

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
agtcggtgga ggagtccagg                                       20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
agtcggtgga ggagtccggg                                       20

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
agtcggtgaa ggagtccgag                                       20

<210> SEQ ID NO 52
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 52
agtcgctgga ggagtccggg                                       20

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53
agtcgttgga ggagtccggg                                       20

<210> SEQ ID NO 54
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 54
agcagcagct gatggagtcc gg                                    22

<210> SEQ ID NO 55
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 55
aggagcagct gatggagtcc gg                                    22

<210> SEQ ID NO 56
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 56
agcagcagct ggtggagtcc gg                                    22

<210> SEQ ID NO 57
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 57
aggagcagct ggtggagtcc gg                                    22

<210> SEQ ID NO 58
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 58
agagacggtg accagggtgc c                                     21

```
<210> SEQ ID NO 59
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 59
ggagacggtg accagggtgc c                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 60
agagatggtg accagggtgc c                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 61
ggagatggtg accagggtgc c                                              21

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = His, 1-pTza or 3-pTza

<400> SEQUENCE: 62

Ala Gly Ala Gly Xaa Ala Gly Ala Gly
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = His, 1-pTza or 3-pTza

<400> SEQUENCE: 63

Val Leu Ile Arg Xaa Gly Glu Ser Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
```

```
<223> OTHER INFORMATION: Xaa = His, 1-pTza or 3-pTza

<400> SEQUENCE: 64

Arg Asn Ile Ile Xaa Gly Ser Asp Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = His, 1-pTza or 3-pTza

<400> SEQUENCE: 65

Gly Ala Lys Arg Xaa Arg Lys Val Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = His, 1-pTza or 3-pTza

<400> SEQUENCE: 66

Val Arg Leu Lys Xaa Arg Lys Leu Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = His, 1-pTza or 3-pTza

<400> SEQUENCE: 67

Met Thr Tyr Ser Xaa Asp Asn Ile Ile
1               5

<210> SEQ ID NO 68
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 68

Glu Val Gln Phe Gly His Ala Gly Ala Cys Ala Asn
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic polypeptide
```

```
<400> SEQUENCE: 69

Gly Arg Arg Met Gly His Ala Gly Ala Ile Ile Ala
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 70

Leu Val Leu Ile Arg His Gly Glu Ser Ala Trp Asn
1               5                   10
```